United States Patent
Okuno et al.

(10) Patent No.: US 9,657,323 B2
(45) Date of Patent: May 23, 2017

(54) POLYPEPTIDE CLEAVAGE METHOD USING OMPT PROTEASE VARIANT

(75) Inventors: Kazuaki Okuno, Okegawa (JP); Masayuki Yabuta, Tatebayashi (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 2013 days.

(21) Appl. No.: 10/573,821

(22) PCT Filed: Sep. 29, 2004

(86) PCT No.: PCT/JP2004/014704
§ 371 (c)(1),
(2), (4) Date: Mar. 28, 2006

(87) PCT Pub. No.: WO2005/030956
PCT Pub. Date: Apr. 7, 2005

(65) Prior Publication Data
US 2007/0077617 A1    Apr. 5, 2007

(30) Foreign Application Priority Data
Sep. 30, 2003    (JP) ................ 2003-342183

(51) Int. Cl.
| | |
|---|---|
| *C12N 9/52* | (2006.01) |
| *C12P 21/06* | (2006.01) |
| *C07K 14/585* | (2006.01) |
| *C07K 14/63* | (2006.01) |
| *C07K 14/695* | (2006.01) |

(52) U.S. Cl.
CPC ............ *C12P 21/06* (2013.01); *C07K 14/585* (2013.01); *C07K 14/63* (2013.01); *C07K 14/695* (2013.01); *C12N 9/52* (2013.01)

(58) Field of Classification Search
None
See application file for complete search history.

(56) References Cited

U.S. PATENT DOCUMENTS

| | | | |
|---|---|---|---|
| 5,013,653 A | 5/1991 | Huston et al. | |
| 5,077,204 A | 12/1991 | Brake et al. | |
| 5,116,750 A | 5/1992 | Gelfand et al. | |
| 5,506,120 A * | 4/1996 | Yamamoto et al. | 435/69.7 |
| 5,700,676 A * | 12/1997 | Bott et al. | 435/221 |
| 7,344,856 B1 | 3/2008 | Okuno et al. | |

FOREIGN PATENT DOCUMENTS

| | | |
|---|---|---|
| EP | 0 114 506 A1 | 8/1984 |
| EP | 0 528 686 A2 | 2/1993 |
| EP | 1 076 097 A1 | 2/2001 |
| WO | 00/52193 | 9/2000 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Sugimura et al, Purification, characterization, and primary structure of *Escherichia coli* protease VII with specificity for paired basic residues: identity of protease VII and OmpT. J Bacteriol. Dec. 1988a;170(12):5625-32.*
GenBank Acc. No. AAA24430 Apr. 26, 1993 from Sugimura et al, J Bacteriol. Dec. 1988;170(12):5625-32.*
GenBank Acc. No. AAA24430 Apr. 26, 1993 from Sugimura et al, J Bacteriol. Dec. 1988;170(12):5625-32. Alignment with GenBank Acc. No. YP_444072.*
Yabuta et al, Hyperproduction of a recombinant fusion protein of *Staphylococcus aureus* V8 protease in *Escherichia coli* and its processing by OmpT protease to release an active V8 protease derivative. Appl Microbiol Biotechnol. Dec. 1995;44(1-2):118-25.*
Grodberg et al, ompT encodes the *Escherichia coli* outer membrane protease that cleaves T7 RNA polymerase during purification. J Bacteriol. Mar. 1988;170(3):1245-53.*
Okuno et al, 2002b (Biotechnol Appl Biochem. Oct. 2002;36(Pt 2):77-84); Public Availability Communication from James Jenkins (ASRC) Dec. 22, 2009.*
Stumpe et al, Identification of OmpT as the protease that hydrolyzes the antimicrobial peptide protamine before it enters growing cells of *Escherichia coli*. J Bacteriol. Aug. 1998;180(15):4002-6.*
Suzuki et al, Studies on protamines. XVI. The complete amino acid sequence of clupeine YII. J Biochem. Dec. 1972;72(6):1419-32.*
Metzler, Table 2 Structure and chemical properties of side chain groups (R) of amino acids. In: Biochemistry Harcourt/Academic Press 2001.*
Hritonenko et al, Omptin proteins: an expanding family of outer membrane proteases in Gram-negative Enterobacteriaceae. Mol Membr Biol. Sep.-Dec. 2007;24(5-6):395-406.*
Hwang et al, Substrate specificity of the *Escherichia coli* outer membrane protease OmpP. J Bacteriol. Jan. 2007;189(2):522-30. Epub Nov. 3, 2006.*
"Histidine", definition. Mosby's Medical Dictionary, 2009, 8th Ed.*
Sugimura et al, A novel outer-membrane-associated protease in *Escherichia coli*. J Bacteriol. Aug. 1988(b);170(8):3650-4.*
Barker et al, Protein Information Resource: a community resource for expert annotation of protein data. Nucleic Acids Res. Jan. 1, 2001;29(1):29-32.*
Sonnhammer et al, Pfam: multiple sequence alignments and HMM-profiles of protein domains. Nucleic Acids Res. Jan. 1, 1998;26(1):320-2.*

(Continued)

*Primary Examiner* — Sheridan Swope
(74) *Attorney, Agent, or Firm* — Drinker Biddle & Reath LLP

(57) ABSTRACT

A polypeptide cleavage method characterized in that arginine or lysine is at the P1 position of a desired cleavage site in a polypeptide, an amino acid other than aspartic acid, glutamic acid or proline is at the P1' position, a single basic amino acid or two or three consecutive basic amino acids are situated at any site in the amino acid sequence from the P10 position to the P3 position or from the P3' position to the P5' position (with the proviso that a single basic amino acid is not situated at the P6 or P4 position), and OmpT protease or its variant enzyme having a substitution at the 97th amino acid from the N-terminus is used to cleave the desired cleavage site in the polypeptide.

13 Claims, 17 Drawing Sheets

(56) References Cited

OTHER PUBLICATIONS

Bateman et al, The Pfam protein families database. Nucleic Acids Res. Jan. 1, 2004 ;32(Database issue):D138-41.*
Finn et al, Pfam: clans, web tools and services. Nucleic Acids Res. Jan. 1, 2006;34(Database issue):D247-51.*
SwissProt/UniProt database Acc. No. P58603 last updated Jun. 15, 2010.*
Lejal et al, Role of Ser-652 and Lys-692 in the protease activity of infectious bursal disease virus VP4 and identification of its substrate cleavage sites. J Gen Virol. Apr. 2000;81(Pt 4):983-92.*
Scheer et al, The activation process of the α1B-adrenergic receptor: Potential role of protonation and hydrophobicity of a highly conserved aspartate. Proc Natl Acad Sci U S A. Feb. 4, 1997; 94(3): 808-813.*
Wolf et al, Structure/function analysis of the periplasmic histidine-binding protein. Mutations decreasing ligand binding alter the properties of the conformational change and of the closed form. J Biol Chem. Jul. 7, 1995;270(27)16097-106.*
Patrick et al, User-friendly algorithms for estimating completeness and diversity in randomized protein-encoding libraries. Protein Eng. Jun. 2003;16(6):451-7.*
Pace et al, Forces contributing to the conformational stability of proteins FASEB J. Jan. 1996;10(1):75-83.*
Darnell et al, Amino Acids-the building blocks of proteins differ only in their side chains. from: Molecular Cell Biology $2^{nd}$ edition, 1990. Pub: Scientific American Books.*
R.A. Kramer et al., "Identification of Essential Acidic Residues of Outer Membrane Protease OmpT Supports a Novel Active Site", FEBS Letters, 2001, pp. 426-430, vol. 505, Published by Elsevier Science B.V.
Kazuaki Okuno et al., "Substrate Specificity at the P1' Site of *Escherichia coli* OmpT Under Denaturing Conditions", Biosci. Biotechnol. Biochem., 2002, pp. 127-134, vol. 66, No. 1.
Niek Dekker et al., "Substrate Specificity of the Integral Membrane Protease OmpT Determined by Spatially Addressed Peptide Libraries", Biochemistry, 2001, pp. 1694-1701, vol. 40, No. 6., Published by American Chemistry Society.
Kazuaki Okuno et al., "An Analysis of Target Preferences of *Escherichia coli* Outer-Membrane Endoprotease OmpT for Use in Therapeutic Peptide Production: Efficient Cleavage of Substrates With Basic Amino Acids at the P4 and P6 Positions", Biotechnol. Appl. Biochem., 2002, pp. 77-84, vol. 36 (Pt. 2), Published by Portland Press Ltd., Printed in Great Britain.
Kazuaki Okuno et al., "Utilization of *Escherichia coli* Outer-Membrane Endoprotease OmpT Variants as Processing Enzymes for Production of Peptides From Designer Fusion Proteins", Applied and Environmental Microbiology, Jan. 2004, pp. 76-86, vol. 70, No. 1, Published by American Society for Microbiology.
Russian Office Action dated May 19, 2009, issued in Russian application No. 2006114756(016028) (with English-language translation).
Vandeputte-Rutten et al., "Crystal structure of the outer membrane protease OmpT from *Escherichia coli* suggest a novel catalytic site," The EMBO Journal, 2001, vol. 20, No. 18, pp. 5033-5039.
Schechter et al., "On the Size of the Active Site in Proteases," Biochem. and Biophys. Research Communications, (1967) vol. 27, No. 2, pp. 157-162.
Hanke et al., "Processing by OmpT of fusion proteins carrying the HlyA transport signal during secretion by the *Escherichia coli* hemolysin transport system," Mol. Gen. Genet, (1992) vol. 233, pp. 42-48.

Clements et al., "Secretion of human epidermal growth factor from *Saccharomyces cerevisiae* using synthetic leader sequences," Gene, (1991) vol. 106, pp. 267-272.
Broekhuijsen et al., "Secretion of heterologous proteins by *Aspergillus niger*: Production of active human interleukin-6 in a protease-deficient mutant by KEX2-like processing of a glucoamylase-hIL6 fusion protein," J. Biotechnol. (1993), vol. 31, pp. 135-145.
Carmona et al., "Nucleotide sequence of the serine protease gene of *Staphylococcus aureus*, strain V8," Nucleic Acids Research, (1987) vol. 15, No. 16, p. 6757.
Houmard et al., "Staphylococcal Protease: A Proteolytic Enzyme Specific for Glutamoyl Bonds," Proc. Nat. Acad. Sci. USA (1972), vol. 69, No. 12, pp. 3506-3509.
Jayaswal et al., "Cloning and Expression of a *Staphylococcus aureus* Gene Encoding a Peptidoglycan Hydrolas Activity," Journal of Bacteriology, Oct. 1990, vol. 172, No. 10, pp. 5783-5788.
Sugimura, K., "Mutant Isolation and Cloning of the Gene Encoding Protease VII from *Escherichia coli*," Biochem and Biophys. Research Comm., (1988), vol. 153, No. 2, pp. 753-759.
Vieira et al., "The pUC plasmids, an M13mp7-derived system for insertion mutagenesis and sequencing with synthetic universal primers," Gene (1982) vol. 19, pp. 259-268.
Taylor et al., "A correction in the nucleotide sequence of the Tn903 kanamycin resistance determinant in pUC4K," Nucleic Acids Research, (1988), vol. 16, No. 1, p. 358.
Yoshikawa et al., "Recombinant Human Glucagon: Large-Scale Purification and Biochemical Characterization," Journal of Protein Chemistry (1992), vol. 11, No. 5, pp. 517-525.
Seeboth et al., "In-vitro cleavage of a fusion protein bound to cellulose using the soluble $yscF_s$ (Kex2) variant," Appl. Microbiol Biotechnol. (1992), vol. 37, pp. 621-625.
Suominen et al., "Enhanced recovery and purification of *Aspergillus* glucoamylase from *Saccharomyces cerevisiae* by the addition of poly(aspartic acid) tails," Enzyme Microb. Technol. (1993), vol. 15, pp. 593-600.
Van Den Bergh et al., "Secretion of biologically active porcine prophospholipase $A_2$ by *Saccharomyces cerevisiae*: Use of the prepro sequence of the α-mating factor," Eur. J. Biochem, (1987), vol. 170, pp. 241-246.
Contreras et al., "Efficient KEX2-Like Processing of a Glucoamylase-Interleukin-6 Fusion Protein by *Aspergillus Nidulans* and Secretion of Mature Interleukin-6," Bio/Technology, (1991) vol. 9, pp. 378-381.
Lennick et al., "High-level expression of α-human atrial natriuretic peptide from multiple joined genes in *Escherichia coli*," Gene 61 (1987), pp. 103-112.
White et al., "A Novel Activity of OmpT: Proteolysis under Extreme Denaturing Conditions," J. Biol. Chem., (1995) vol. 270, No. 22, pp. 12990-12994.
McCarter, John D. et al., "Substrate Specificity of the *Escherichia coli* Outer Membrane Protease OmpT", Journal of Bacteriology, Sep. 2004, pp. 5919-5925, vol. 186, No. 17, XP002452676.
Stathopoulos, C., "Structural Features, Physiological Roles, and Biotechnological Applications of the Membrane Proteases of the OmpT Bacterial Endopeptidase Family: A Micro-Review", Membrane and Cell Biology, Harwood Academic Publishers, vol. 12, No. 1, 1998, pp. 1-8, XP009002096.
European Search Report mailed on Oct. 10, 2007 in EP 04773628.5.
Search Report dated Dec. 13, 2004 from International PCT Appln. PCT/JP2004/014704 filed Sep. 9, 2004.

* cited by examiner

Fig. 15
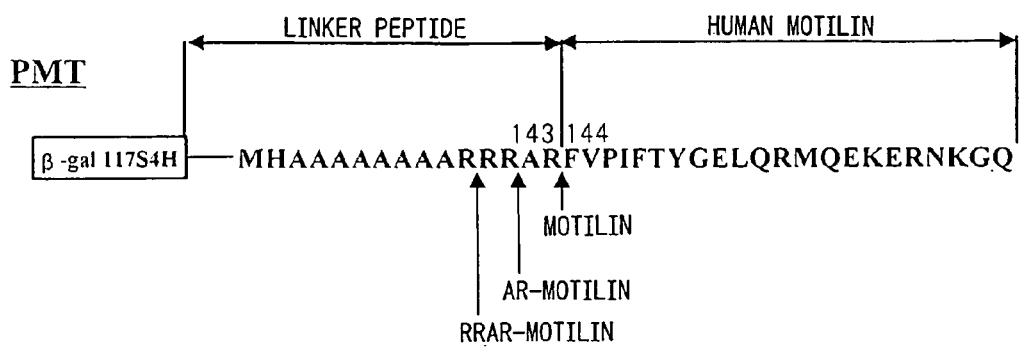
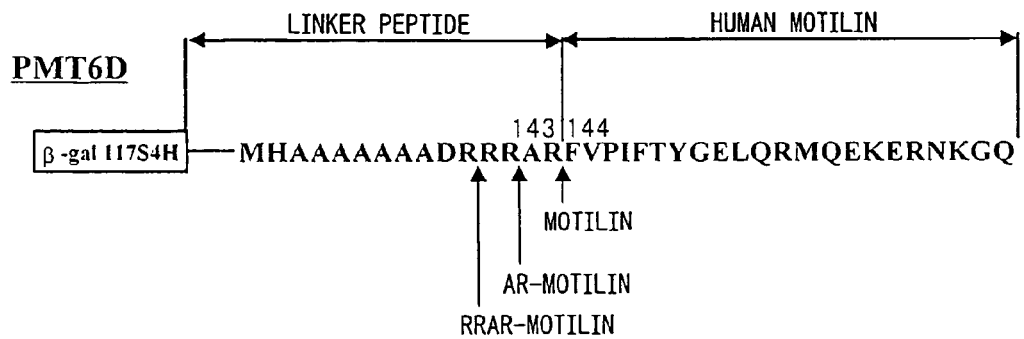
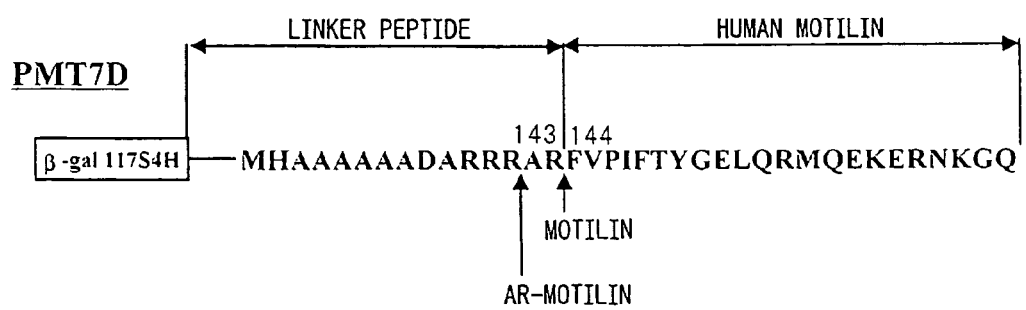

POLYPEPTIDE CLEAVAGE METHOD USING OMPT PROTEASE VARIANT

REFERENCE TO A SEQUENCE LISTING

The instant application contains a Sequence Listing which has been submitted in ASCII format via EFS-Web and is hereby incorporated by reference in its entirety. Said ASCII copy, created on Oct. 7, 2011, is named 47259500.txt and is 29,297 bytes in size.

TECHNICAL FIELD

The present invention relates to a method for directly cleaving a physiologically active peptide, protein or its derivative from a fusion protein utilizing E. coli OmpT protease or a variant thereof. More specifically, it relates to a method for cleavage of a fusion protein using E. coli mature OmpT protease, wherein a basic amino acid is situated at the P3 position, P4 position and P5 position of the cleavage site in order to increase the cleavage efficiency at the peptide bond between the P1 and P1' positions of the cleavage site, and further to a method of using a variant OmpT protease having its substrate specificity for the P1' position modified by substitution of the 97th amino acid from the N terminal, for efficient release and production of physiologically active peptides, proteins and their derivatives from fusion proteins even when the amino acid at the P1' site is an amino acid other than arginine or lysine.

BACKGROUND ART

E. coli OmpT protease (SEQ ID NO: 41) is present in E. coli outer membrane fractions, and this protease selectively cleaves primarily peptide bonds between basic amino acid pairs. Proteins having homologous amino acid sequences with E. coli OmpT protease and having or believed to have protease activity are also found in intestinal bacteria such as Salmonella, Yersinia and Shigella, and this group of proteins is known as the omptin family.

E. coli OmpT protease (SEQ ID NO: 41) has a molecular weight of approximately 33,500. Sugimura et al. have examined the substrate specificity of OmpT protease (SEQ ID NO: 41) and have reported that the enzyme specifically cleaves the central peptide bonds between the basic amino acid pairs of arginine-arginine, lysine-lysine, arginine-lysine and lysine-arginine (Sugimura, K. and Nishihara, T. J. Bacteriol. 170: 5625-5632, 1988).

However, the enzyme does not cleave all basic amino acid pairs, as it is highly specific. For example, human γ-interferon contains 10 basic amino acid pairs, but only two of them are cleaved (Sugimura, K. and Higashi, N.J. Bacteriol. 170: 3650-3654, 1988). This is attributed to the influence of the three-dimensional structure of the human γ-interferon substrate and to the amino acid sequences of sites thought to be recognized by the enzyme which are adjacent to basic amino acid pairs.

The amino acid positions of substrates referred to throughout the present specification are assigned according to the notation method of Schechter and Berger (Schechter, I. and Berger, A. Biochem. Biophys. Research. Commun. 27: 157-162, 1967). That is, the peptide bond between the P1 position and P1' position of Pn . . . P2-P1-P1'-P2' . . . Pn' is the cleavage site, and the amino acids are represented by their standard single letter or three-letter abbreviations, with ↓ indicating the cleavage site.

For example, if cleavage is between lysine and arginine of the amino acid sequence -leucine-tyrosine-lysine-arginine-histidine- (-Leu-Tyr-Lys↓Arg-His-) (SEQ ID NO: 9), leucine is at the P3 position, tyrosine is at the P2 position, lysine is at the P1 position, arginine is at the P1' position, and histidine is at the P2' position.

Also, unless otherwise specified, these designations will be used as the amino acid positions corresponding to the original sequence even when an amino acid substitution has been introduced at the cleavage site or its surrounding amino acid sequence such that it is no longer cleavable, or a new cleavage site has resulted.

OmpT protease cleavage sites have been discovered with amino acid sequences other than basic amino acid pairs, and Dekker et al., using substrates with amino acid substitutions introduced into an OmpT protease substrate comprising the amino acid sequence Ala-Arg-Arg-Ala (SEQ ID NO: 10) (P2-P1↓,P1'-P2'), have reported that OmpT protease exhibits high specificity for the basic amino acids arginine and lysine as the amino acid at the P1 position of the cleavage site, but is less stringent in regard to the amino acid at the P1' position (Dekker, N. et al. Biochemistry 40: 1694-1701, 2001).

Moreover, the present inventors, using as the substrate a fusion protein capable of being cleaved by the enzyme under polypeptide-denaturing conditions in the presence of urea wherein an amino acid substitution is introduced at the P1' position of the fusion protein, have discovered that cleavage occurs when the P1' position amino acid is an amino acid other than aspartic acid, glutamic acid or proline (Okuno, K. et al. Biosci, Biotechnol. Biochem. 66: 127-134, 2002, Japanese Patent Application No. 2000-602803). Yet the cleavage efficiency in these cases is still lower than when the amino acid residue at the P1' position is arginine or lysine.

As for the specificity with respect to the sequences adjacent to the cleavage site, it has been demonstrated that cleavage fails to occur when an acidic amino acid is present at the P2 or P2' position (Dekker, N. et al. Biochemistry 40: 1694-1701, 2001).

The present inventors have also reported that cleavage efficiency is increased when arginine or lysine is present as a basic amino acid at the P4 position or P6 position, while conversely it is decreased in the case of an acidic amino acid such as aspartic acid or glutamic acid (Okuno, K. et al. Biotechnol. Appl. Biochem. 36: 77-84, 2002, Japanese Patent Application No. 2000-602803).

While the specificity for other sequences adjacent to the cleavage site has not been established, the fact that OmpT protease cleaves protamines, which are highly basic antimicrobial peptides (Stumpe, S. et al. J. Bacteriol. 180: 4002-4006, 1998), and that many acidic amino acids are found in the OmpT protease extracellular domain involved in protease activity (Vandeputte-Rutten, L. et al. EMBO J. 20: 5033-5039, 2001), suggests that charge effects are important for the interaction between OmpT protease and its substrate.

As regards applications of OmpT protease, the high cleavage site specificity and the fact that the protease is present on the outer membrane of E. coli means that the protease can be used as a processing enzyme for releasing target polypeptides from fusion proteins created by gene recombination techniques.

Hanke et al., in carrying out secretion of cholesterol esterase using E. coli, fused it with E. coli hemolysin A protein, secreted the fusion protein extracellularly and allowed OmpT protease on the outer membrane to act thereon, thereby successfully obtaining active cholesterol esterase from the fusion protein. Here, a linker with an arginine-lysine sequence was added for cleavage of the sequence with OmpT protease (Hanke, C. et al. Mol. General. Genet. 233: 42-48, 1992).

The present inventors have discovered that OmpT protease is resistant to denaturing agents, and have utilized this property to show that fusion proteins expressed as inclusion bodies can be cleaved in the presence of denaturing agents. Specifically, a *Staphylococcus aureus* V8 protease derivative fusion protein was expressed as an inclusion body in an *E. coli* expression system, solubilized with urea and then acted upon by OmpT protease in the presence of urea, which resulted in release of the V8 protease derivative portion from the fusion protein, and subsequent refolding allowed successful production of the V8 protease derivative with enzyme activity (Yabuta, M. et al. Appl. Microbiol. Biotechnol. 44: 118-125, 1995).

Normally, release of a target polypeptide or protein from a fusion protein is accomplished using an enzyme with high amino acid sequence specificity as the processing enzyme. The known proteases used in such cases include factor Xa, thrombin and enterokinase, but because these enzymes are mammalian derived enzymes and therefore in short supply and costly, they are not suitable for industrial mass processing of peptides and proteins by fusion protein methods. In addition, when the target polypeptide or protein is to be used as a pharmaceutical, it is also necessary to consider viral contamination originating from the enzyme source, as well as contamination by altered prion proteins which are causative factors of bovine spongiform encephalopathy.

Since OmpT protease is derived from *E. coli*, its use as a processing enzyme is clearly preferred over the aforementioned enzymes in terms of supply volume, cost and safety. Moreover, because OmpT protease is also present in inclusion bodies, it can act simply upon lysing the fusion protein with a denaturing agent such as urea even when the fusion protein is expressed as an inclusion body. Furthermore, OmpT protease is also present on the *E. coli* outer membrane and therefore OmpT protease reaction can be carried out by addition of the cells themselves to the reaction system (Grodberg, J. and Dunn, J. J. J. Bacteriol. 170: 1245-1253, 1988).

Most proteases used for processing of *E. coli*-produced fusion proteins to obtain target polypeptides, in industrial peptide production such as production of pharmaceuticals, are not derived from *E. coli* and must therefore be purified for use. A major improvement in polypeptide production cost could thus be afforded if OmpT protease could be used as the processing protease by mere addition of the outer membrane fraction or inclusion body lysis from *E. coli* cells themselves, without requiring purification. However, processing of fusion proteins using conventional *E. coli* OmpT protease, with the exception of a few cases, has been restrictive in that only polypeptides whose N-terminal amino acids are lysine or arginine are released.

Despite the usefulness of OmpT protease, knowledge has been limited, prior to the present invention, for the use of OmpT protease as a cleavage enzyme for fusion proteins, as regards how the sequence of the cleavage site and its adjacent amino acids should be designed in order to achieve specific and efficient cleavage at the intended site. Consequently, the types of N-terminal amino acids for efficiently cleavable target polypeptides have been limited. This has been a cause of problems including restrictions on the types of target polypeptides that can be obtained and resulting in, for example, the inability to accomplish efficient cleavage even when cleavage is possible.

Patent document 1: Japanese Patent Application No. 2000-602803
Non-patent document 1: Sugimura, K. and Nishihara, T. J. Bacteriol. 170: 5625-5632, 1988
Non-patent document 2: Sugimura, K. and Higashi, N.J. Bacteriol. 170: 3650-3654, 1988
Non-patent document 3: Schechter, I. and Berger, A. Biochem. Biophys. Research. Commun. 27: 157-162, 1967
Non-patent document 4: Dekker, N. et al. Biochemistry 40: 1694-1701, 2001
Non-patent document 5: Okuno, K. et al. Biosci, Biotechnol. Biochem. 66: 127-134, 2002
Non-patent document 6: Okuno, K. et al. Biotechnol. Appl. Biochem. 36: 77-84, 2002
Non-patent document 7: Stumpe, S. et al. J. Bacteriol. 180: 4002-4006, 1998
Non-patent document 8: Vandeputte-Rutten, L. et al. EMBO J. 20: 5033-5039, 2001
Non-patent document 9: Hanke, C. et al. Mol. General. Genet. 233: 42-48, 1992
Non-patent document 10: Yabuta, M. et al. Appl. Microbiol. Biotechnol. 44: 118-125, 1995
Non-patent document 11: Grodberg, J. and Dunn, J. J. J. Bacteriol. 170: 1245-1253, 1988

DISCLOSURE OF THE INVENTION

It is an object of the present invention to overcome the problems mentioned above, by providing a method for efficiently and specifically releasing any type of target polypeptide from a fusion protein, by utilizing OmpT protease or its variant as the processing enzyme, and specifically, to efficiently cleave only the single bond of P1-P1' of a fusion protein wherein the N-terminal amino acid of the target polypeptide is the P1' position amino acid residue.

The present inventors further examined the OmpT protease cleavage site and its adjacent amino acid sequence, and considered that if a novel cleavage method or recognition/cleavage sequence could be devised, the restrictions described above could be overcome and the enzyme would be even more useful as a processing enzyme for fusion proteins. Moreover, it was speculated that introducing a site-directed mutation into the OmpT protease itself to produce an OmpT protease variant having a different substrate specificity than the wild type could be of great utility.

Thus, given that the amino acid sequence adjacent to the cleavage site is important for substrate recognition and cleavage by OmpT protease, the present inventors utilized the known cleavage site and investigated the cleavage site and its adjacent amino acid sequence in order to create new substrate specificities, and then diligently carried out research on their application to cleavage of fusion proteins.

According to the invention, "OmpT protease" refers to mature OmpT protease from *E. coli* (SEQ ID NO: 41) after removal of the signal peptide, or a protein other than OmpT protease having OmpT protease activity (OmpT-like protease). As OmpT-like proteases there may be mentioned (1) *Yersinia pestis* plasminogen activator, (2) *Salmonella typhimurium* E protein, (3) *Escherichia coli* and (4) *Shigella flexneri* SopA.

According to the invention, "OmpT protease 97th amino acid variant" refers to an OmpT protease variant having the aspartic acid at position 97 ($Asp^{97}$) of the OmpT protease replaced with a different amino acid, or a variant of the aforementioned OmpT-like protease having an amino acid equivalent to the 97th amino acid from the N-terminus of the OmpT protease replaced (OmpT-like protease 97th-equivalent amino acid variant).

As examples of other amino acids to substitute for the OmpT protease 97th aspartic acid there may be mentioned alanine, leucine, phenylalanine, methionine, serine, threonine, cysteine, asparagine, glutamine, glutamic acid and histidine. As OmpT-like protease 97th-corresponding amino acid variants there may be mentioned variants of the aforementioned OmpT-like proteases wherein the aspartic acid at position 117 for (1) *Yersinia pestis* plasminogen activator (counted as the amino acid residue from the N-terminus of the full amino acid sequence including the signal peptide; for OmpT as well, the 97th amino acid counted as the number of amino acid residues including the signal peptide is at position 117), the aspartic acid at position 134 for (2) *Salmonella typhimurium* E protein, the aspartic acid at position 117 for (3) *Escherichia coli* OmpP and the aspartic acid at position 117 for (4) *Shigella flexneri* SopA is replaced with, for example, alanine, leucine, phenylalanine, methionine, serine, threonine, cysteine, asparagine, glutamine, glutamic acid or histidine.

The term "target peptide" according to the invention is used not only in regard to the peptide which is to be finally obtained, but also including any production intermediate ("precursor peptide") which, after cleavage from the fusion protein by OmpT protease or the like, is subjected to subsequent modification reaction or cleavage reaction.

The term "protecting peptide" according to the invention is used to refer to a peptide which forms a fusion protein with the target peptide via a linker peptide, and it includes the linker peptide.

The term "desired cleavage site" according to the invention refers to any site in the polypeptide, a site between the C-terminus of the linker peptide of the fusion protein composed of the target protein fused with the protected peptide via the linker peptide, and the N-terminus of the target peptide, or any site in the linker-peptide.

The main gist of the present invention relates to the following aspects (1) to (4):

(1) A polypeptide cleavage method characterized in that arginine or lysine is at the P1 position of a desired cleavage site in a polypeptide, an amino acid other than aspartic acid, glutamic acid or proline is at the P1' position, a single basic amino acid or two or three consecutive basic amino acids are situated at any site in the amino acid sequence from the P10 position to the P3 position or from the P3' position to the P5' position (with the proviso that a single basic amino acid is not situated at the P6 or P4 position), and OmpT protease is used to cleave the desired cleavage site in the polypeptide, and a method for producing a target peptide characterized by obtaining the target peptide from a fusion protein using the cleavage method.

(2)A polypeptide cleavage method characterized in that an OmpT protease 97th amino acid variant is used to cleave a desired cleavage site in a polypeptide, and a method for producing a target peptide characterized by obtaining the target peptide from a fusion protein using the cleavage method.

(3) A method according to (2) above, wherein arginine or lysine is at the P1 position of a desired cleavage site in a polypeptide, an amino acid other than arginine or lysine is at the P1' position, and a single basic amino acid or two or three consecutive basic amino acids are situated at any site in the amino acid sequence from the P10 position to the P3 position or from the P3' position to the P5' position.

(4) A polypeptide cleavage method wherein an OmpT protease or an OmpT protease 97th amino acid variant is used to cleave a desired cleavage site in a polypeptide, the polypeptide cleavage method being characterized in that when a site which is not desired to be cleaved by the protease is present in the polypeptide, cleavage at that site is inhibited by situating an acidic amino acid at the P3 position of the site, and a method for producing a target peptide characterized by obtaining the target peptide from a fusion protein using the cleavage method.

Aspect (1) above is based on the new knowledge that the cleavage efficiency is increased by substituting basic amino acids for amino acids from the P10 position to the P3 position (excluding cases where only the P6 or P4 position is replaced by a basic amino acid), and most preferably from the P5 position to the P3 position of the OmpT protease cleavage site. However, because of the nature of OmpT to easily cleave peptide bonds between consecutive basic amino acids, situating basic amino acids consecutively at the P5 to P3 positions results in cleavage of the peptide bonds at those sites by OmpT.

Nevertheless, by utilizing the known property whereby the cleavage efficiency of OmpT for three consecutive arginine residues is lower than for two consecutive arginine residues, it was possible to inhibit cleavage between arginine residues from the P5 to P3 positions by situating three consecutive arginine residues from the P5 to P3 positions. That is, it was thereby possible to promote cleavage at the desired site (cleavage between the amino acids at the P1 position and P1' position) while inhibiting cleavage at undesirable sites (cleavage between amino acids from the P5 to P3 positions).

Thus, it was discovered that exceedingly efficient cleavage can be achieved with OmpT protease not only when the P1' position of the desired cleavage site of the polypeptide is arginine or lysine as known in the prior art but also when it is another amino acid other than aspartic acid, glutamic acid or proline, by designing the desired polypeptide to contain an amino acid sequence having basic amino acids (preferably arginine) situated at the P3, P4 and P5 positions of the desired cleavage site.

This method is particularly convenient when a fusion protein containing a target polypeptide is produced in an *E. coli* host and OmpT protease that is either natural to *E. coli* or introduced by genetic engineering is used to cut off from the fusion protein the target polypeptide wherein the N-terminal amino acids situated at the C-terminal end from the P1' position of the desired cleavage site are amino acids other than aspartic acid, glutamic acid or proline.

The discovery that substitution of specific amino acids for the 97th amino acid from the N-terminus of OmpT protease permits actual cleavage of cleavage sites that cannot be cleaved with OmpT protease, as according to aspects (2) and (3) above, is extremely useful as it allows production of target peptides with variety of selection in the types of N-terminal amino acids of the peptides. In particular, by designing the linker sequence of a fusion protein to be: -Arg-Arg-Arg-Ala-Arg- (SEQ ID NO: 11) target peptide, for production of a target peptide using the fusion protein, and utilizing as the processing protease a protease variant having most preferably leucine, methionine or histidine substituting for the 97th aspartic acid from the N-terminus of OmpT protease, it is possible to efficiently and specifically release even polypeptides wherein the N-terminal amino acid is other than lysine or arginine.

Although cleavage of fusion proteins is carried out using an *E. coli* OmpT protease variant throughout the examples of the present application, it is also fully possible to cleave a fusion protein using an enzyme with OmpT protease activity other than OmpT protease or a variant of the enzyme wherein the amino acid corresponding to the 97th amino acid from the N-terminus of OmpT protease in its amino acid sequence is replaced.

In regard to (4) above, it was discovered that when a polypeptide or fusion protein contains a site which is not desired to be cleaved by OmpT protease or its variant, cleavage at that site is inhibited by situating an acidic amino acid at the P3 position of the site. This discovery is useful for designing fusion proteins particularly when target peptides are to be obtained from the fusion proteins, and it allows highly efficient production of such target peptides.

More specifically, the present invention relates to the following:

(1) A polypeptide cleavage method characterized in that arginine or lysine is at the P1 position of a desired cleavage site in a polypeptide, an amino acid other than aspartic acid, glutamic acid or proline is at the P1' position, a single basic amino acid or two or three consecutive basic amino acids are situated at any site in the amino acid sequence from the P10 position to the P3 position or from the P3' position to the P5' position (with the proviso that a single basic amino acid is not situated at the P6 or P4 position), and OmpT protease is used to cleave the desired cleavage site in the polypeptide.

(2) A method for producing a target peptide characterized by obtaining a target peptide from a fusion protein, the cleavage site of the fusion protein being a desired cleavage site comprising a protecting peptide whose C-terminus is arginine or lysine, fused via the desired cleavage site with a target peptide whose N-terminus is an amino acid other than aspartic acid, glutamic acid or proline, wherein a single basic amino acid or two or three consecutive basic amino acids are situated at any site in the amino acid sequence from the P10 position to the P3 position or from the P3' position to the P5' position (with the proviso that in the case of a single basic amino acid, it is not situated at the P6 or P4 position), host cells are transformed with an expression plasmid having a gene coding for the fusion protein wherein said cleavage site is a cleavage site which is cleavable by OmpT protease, and the gene is expressed in the cells and is cleaved by the protease at the cleavage site.

(3) The method of (1) or (2) above wherein, if a site which is not desired to be cleaved by OmpT protease is present in the polypeptide or the fusion protein, cleavage at that site is inhibited by situating an acidic amino acid at the P3 position of the site.

(4) The method of any one of (1) to (3) above, which comprises situating two or three consecutive basic amino acids between the P10 and P3 positions of the desired cleavage site in the polypeptide or fusion protein.

(5) The method of (4) above, which comprises situating three consecutive basic amino acids between the P5 and P3 positions of the desired cleavage site in the polypeptide or fusion protein.

(6) The method of any one of (1) to (5) above, wherein the basic amino acids are arginine and/or lysine.

(7) The method of (6) above, wherein the basic amino acids are arginine.

(8) A polypeptide cleavage method wherein OmpT protease is used for cleavage at a desired cleavage site in the polypeptide, or a method for producing a target peptide which comprises cleavage at a desired cleavage site in a fusion protein, the method being characterized in that, if a site which is not desired to be cleaved by OmpT protease is present in the polypeptide or the fusion protein, cleavage at that site is inhibited by situating an acidic amino acid at the P3 position of the site.

(9) The method of any one of (3) to (8) above, wherein the acidic amino acid is aspartic acid.

(10) The method of any one of (1) to (9) above, wherein the amino acid sequence from the P5 to P1 positions of the desired cleavage site in the polypeptide or fusion protein is Arg-Arg-Arg-Ala-Arg (SEO ID NO: 11).

(11) The method of any one of (1) to (9) above, wherein the amino acid sequence from the P7 to P1 positions of the desired cleavage site in the polypeptide or fusion protein is Asp-Ala-Arg-Arg-Arg-Ala-Arg (SEQ ID NO: 12).

(12) A polypeptide cleavage method characterized by cleaving a desired cleavage site of a polypeptide using an OmpT protease 97th amino acid variant wherein the 97th amino acid from the N-terminus of the OmpT protease is alanine, leucine, phenylalanine, methionine, serine, threonine, cysteine, asparagine, glutamine, glutamic acid or histidine.

(13) A polypeptide cleavage method characterized in that, when the P1 position of the desired cleavage site in the polypeptide is arginine or lysine and the P1' position is an amino acid other than arginine or lysine, the desired cleavage site of the polypeptide is cleaved using an OmpT protease 97th amino acid variant wherein the 97th amino acid from the N-terminus of the OmpT protease is alanine, leucine, phenylalanine, methionine, serine, threonine, cysteine, asparagine, glutamine, glutamic acid or histidine.

(14) A polypeptide cleavage method characterized in that the P1 position of the desired cleavage site in the polypeptide is arginine or lysine, the P1' position is an amino acid other than arginine or lysine, a single basic amino acid or two or three consecutive basic amino acids are situated at any site in the amino acid sequence from the P10 position to the P3 position or from the P3' position to the P5' position, and the desired cleavage site of the polypeptide is cleaved using an OmpT protease 97th amino acid variant wherein the 97th amino acid from the N-terminus of the OmpT protease is alanine, leucine, phenylalanine, methionine, serine, threonine, cysteine, asparagine, glutamine, glutamic acid or histidine.

(15) A method for producing a target peptide, characterized by transforming host cells with an expression plasmid having a gene coding for a fusion protein comprising a target peptide fused with a protecting peptide via a desired cleavage site that can be cleaved by an OmpT protease 97th amino acid variant wherein the 97th amino acid from the N-terminus of the OmpT protease is alanine, leucine, phenylalanine, methionine, serine, threonine, cysteine, asparagine, glutamine, glutamic acid or histidine, expressing the gene in the cells, and obtaining the target peptide from the fusion protein by cleavage with the protease at the cleavage site.

(16) A method for producing a target peptide, characterized by transforming host cells with an expression plasmid having a gene coding for a fusion protein comprising a protecting peptide whose-C-terminus is arginine or lysine fused with a target peptide whose N-terminus is an amino acid other than arginine or lysine, via a desired cleavage site that can be cleaved by an OmpT protease 97th amino acid variant wherein the 97th amino acid from the N-terminus of the OmpT protease is alanine, leucine, phenylalanine, methionine, serine, threonine, cysteine, asparagine, glutamine, glutamic acid or histidine, expressing the gene in the cells, and obtaining the target peptide from the fusion protein by cleavage with the protease at the cleavage site.

(17) A method for producing a target peptide, characterized by transforming host cells with an expression plasmid having a gene coding for a fusion protein wherein a single basic amino acid or two or three consecutive basic amino acids are situated at any site in the amino acid sequence from the P10 position to the P3 position or from the P3' position to the P5' position at a desired cleavage site of a fusion protein comprising a protecting peptide whose C-terminus is arginine or lysine fused with a target peptide whose N-terminus is an amino acid other than arginine or lysine, via the cleavage site, and the desired cleavage site is a cleavage site that can be cleaved by an OmpT protease 97th amino acid variant wherein the 97th amino acid from the N-terminus of the OmpT protease is alanine, leucine, phenylalanine, methionine, serine, threonine, cysteine, asparagine, glutamine, glutamic acid or histidine, expressing the gene in the cells, and obtaining the target peptide from the fusion protein by cleavage with the protease at the cleavage site.

(18) The method of any one of (12) to (17) above wherein, if a site which is not desired to be cleaved by the OmpT protease 97th amino acid variant is present in the polypeptide or fusion protein, cleavage at that site is inhibited by situating an acidic amino acid at the P3 position of the site.

(19) The method of any one of (12) to (18) above, which comprises situating two or three consecutive basic amino acids between the P10 and P3 positions of the desired cleavage site in the polypeptide or fusion protein.

(20) The method of (19) above, which comprises situating three consecutive basic amino acids between the P5 and P3 positions of the desired cleavage site in the polypeptide or fusion protein.

(21) The method of any one of (14) or (17) to (20) above, wherein the basic amino acids are arginine and/or lysine.

(22) The method of (21) above, wherein the basic amino acids are arginine.

(23) A polypeptide cleavage method wherein an OmpT protease 97th amino acid variant is used for cleavage at a desired cleavage site in the polypeptide, or a method for producing a target peptide which comprises cleavage at a desired cleavage site in a fusion protein, the method being characterized in that, if a site which is not desired to be cleaved by the OmpT protease 97th amino acid variant is present in the polypeptide or the fusion protein, cleavage at that site is inhibited by situating an acidic amino acid at the P3 position of the site.

(24) The method of any one of (18) to (23) above, wherein the acidic amino acid is aspartic acid.

(25) The method of any one of (12) to (24) above, wherein the amino acid sequence from the P5 to P1 positions of the desired cleavage site in the polypeptide or fusion protein is Arg-Arg-Arg-Ala-Arg (SEQ ID NO: 11).

(26) The method of any one of (12) to (24) above, wherein the amino acid sequence from the P7 to P1 positions of the desired cleavage site in the polypeptide or fusion protein is Asp-Ala-Arg-Arg-Arg-Ala-Arg (SEQ ID NO: 12).

(27) The method of any one of (12) to (26) above, wherein the 97th amino acid from the N-terminus of the OmpT protease is leucine, methionine or histidine.

(28) The method of any one of (12) to (26) above, wherein the P1' position of the desired cleavage site of the polypeptide or fusion protein or the N-terminus of the target peptide is serine or alanine, and the 97th amino acid of the OmpT protease 97th amino acid variant used is leucine.

(29) The method of any one of (12) to (26) above, wherein the P1' position of the desired cleavage site of the polypeptide or fusion protein or the N-terminus of the target peptide is phenylalanine, alanine, serine, cysteine or tyrosine, and the 97th amino acid of the OmpT protease 97th amino acid variant used is methionine.

(30) The method of any one of (12) to (26) above, wherein the P1' position of the desired cleavage site of the polypeptide or fusion protein or the N-terminus of the target peptide is alanine, valine, isoleucine, methionine, serine, threonine, cysteine or asparagine, and the 97th amino acid of the OmpT protease 97th amino acid variant used is histidine.

(31) The method of any one of (2) to (11) and (15) to (30) above, wherein the target peptide is a peptide composed of between 22 and 45 amino acid residues.

(32) The method of (31) above, wherein the target peptide is adrenocorticotropic hormone (1-24), motilin or calcitonin precursor.

(33) The method of any one of (2) to (11) and (15) to (32) above, wherein the host cells are *E. coli*.

(34) The method of any one of (1) to (33) above, which comprises using as the cleaving protease bacterial cells expressing a gene coding for OmpT protease or an OmpT protease 97th amino acid variant wherein the 97th amino acid from the N-terminus of OmpT protease is alanine, leucine, phenylalanine, methionine, serine, threonine, cysteine, asparagine, glutamine, glutamic acid or histidine.

(35) The method of any one of (1) to (33) above, which comprises co-expressing a gene coding for OmpT protease or an OmpT protease 97th amino acid variant wherein the 97th amino acid from the N-terminus of OmpT protease is alanine, leucine, phenylalanine, methionine, serine, threonine, cysteine, asparagine, glutamine, glutamic acid or histidine, and a gene coding for a polypeptide or fusion protein whose cleavage by the protease is desired.

BRIEF DESCRIPTION OF THE DRAWINGS

FIG. 15 shows the structures of the fusion proteins PMT (Residues 129-165 of SEQ ID NO: 6), PMT6D (SEQ ID NO: 37) and PMT7D (SEQ ID NO: 38). The numbers over the amino acid sequences of the fusion proteins represent the amino acid sequence numbers from the respective N-terminus. β-gal117S4H represents the protecting protein deriving from 117 amino acids from the N-terminus of *E. coli* β-galactosidase, and the linker peptide is the portion from amino acid sequence No. 128 (glutamine) to No. 143 (arginine). The amino acid sequence up to arginine at position 143 in the fusion proteins matches the amino acid sequence up to arginine at position 143 from the N-terminus of the fusion proteins PA23', PA3D23' and PA4D23' (FIG. 4). The cleavage sites of the fusion proteins by the OmpT protease variant D97M are indicated by arrows. AR-motilin is a polypeptide comprising Ala-Arg-motilin released by cleavage at $Arg^{141}$-$Ala^{142}$, and RRAR-motilin (SEQ ID NO: 13) is a polypeptide comprising Arg-Arg-Ala-Arg-motilin (SEQ ID NO: 13) released by cleavage at $Arg^{139}$-$Arg^{140}$.

BEST MODE FOR CARRYING OUT THE INVENTION

Figure 1:
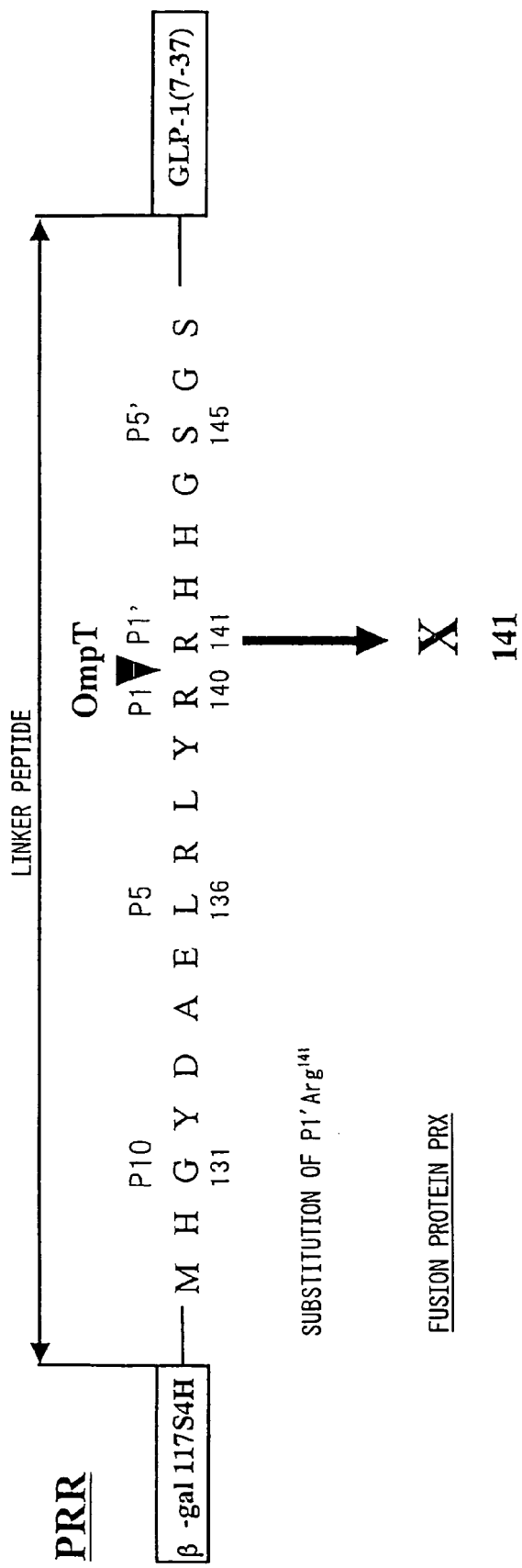
FIG. 1 is a diagram showing the structures of the fusion proteins PRR (Residues 129-147 of SEQ ID NO: 1) and PRX. The position of each amino acid is shown on the amino acid sequence of the fusion protein PRR, and the numbers below represent the amino acid sequence numbers from the N-terminus of PRR. β-gal117S4H represents the protecting protein deriving from 117 amino acids from the N-terminus of *E. coli* β-galactosidase, GLP-1(7-37) represents human glucagon-like peptide-1(7-37), and the linker peptide is the portion from amino acid sequence No. 128 (glutamine) to No. 153 (arginine). The OmpT protease cleavage site on the fusion protein PRR is indicated by a black wedge. The fusion protein PRX is a fusion protein wherein arginine at position 141 of PRR is replaced with any of 19 other different amino acids.

The present invention will now be explained in greater detail.

Plasmid pG117S4HompPRR is an expression plasmid which expresses a fusion protein (PRR) comprising glucagon-like peptide-1 (7-37) (GLP-1(7-37)).

The protected protein of this fusion protein is composed of β-gal117S4H containing the 117 N-terminal amino acids of *E. coli* β-galactosidase as the protecting protein, a linker sequence comprising 26 amino acids containing an arginine-arginine sequence, and GLP-1(7-37). The present inventors had already discovered that *E. coli* OmpT protease (SEQ ID NO: 41) cleaves the central peptide bond of the arginine-arginine sequence in the PRR linker sequence, releasing a target polypeptide of 44 amino acids containing GLP-1(7-37) (Okuno, K. et al. Biosci., Biotechnol. Biochem. 66:127-134, 2002).

The present inventors constructed PA based on the fusion protein (PRR), as a fusion protein having arginine at the P1 and P1' positions and having all of the other amino acids from the P10 to P5' positions replaced with alanine.

Also, a fusion protein (PAn) was constructed starting from the fusion protein PA and replacing the alanine at each position with arginine, and the effect on OmpT protease cleavage by situating the basic amino acid arginine adjacent to the OmpT protease cleavage site was examined.

As a result, it was newly discovered that the cleavage efficiency can be increased if a basic amino acid (for example, arginine or lysine) is present at positions between P10 and P3 or positions P3' and P5' of the amino acid sequence adjacent to the cleavage site (except for cases where only position P6 or P4 is replaced with a basic amino acid).

On the other hand, when P2 or P2' is arginine, the sequence contains three consecutive arginines instead of only the two arginines at positions P1 and P1' situated at the cleavage site, and this case was found instead to have a reduced cleavage efficiency. That is, although the cleavage efficiency is increased if arginine is present around the cleavage site, the cleavage efficiency is reduced in the case of three consecutive arginines, and therefore the cleavage efficiency can be controlled by substituting arginine in the cleavage site adjacent amino acid sequence.

For fusion protein PA3' wherein arginine is present at position P3' (cleavage site adjacent amino acid sequence=-Ala-Ala-Arg[P1]-Arg[P1']-Ala-Arg[P3']-Ala[P4]-Ala-) (SEQ ID NO: 14), it was found that cleavage also occurs between arginine at position P3' and alanine at position P4', and a sequence was discovered that allowed efficient cleavage at the arginine-alanine site. Since the fact that the substrate was efficiently cleaved with a sequence other than one having consecutive basic amino acids is extremely important for using OmpT protease as a processing enzyme, the present inventors carried out further investigation.

Upon investigating various amino acid sequences based on the knowledge that cleavage efficiency is increased by situating arginine at the cleavage site adjacency and the knowledge that three consecutive arginines render cleavage between arginine-arginine more difficult, it was found that in the amino acid sequence -Arg-Arg-Arg-Ala-Arg-Ala- (SEQ ID NO: 15), the major cleavage occurs at -Arg-Arg-Arg-Ala-Arg↓Ala-(SEQ ID NO: 15). In other words, this demonstrated a property whereby situating three consecutive basic amino acids promotes cleavage at basic amino acid sites thereafter.

However, cleavage did occur in the aforementioned amino acid sequence (-Arg-Arg-Arg-Ala-Arg-Ala-) (SEQ ID NO: 15) even in the three consecutive arginine residue sequence. In order to inhibit this, the amino acid sequence -Asp-Ala-Arg-Arg-Arg-Ala-Arg↓Ala- (SEQ ID NO: 16) was constructed having aspartic acid situated as an acidic amino acid in the amino acid sequence upstream from the N-terminal end. The arginine-alanine cleavage efficiency was reduced by half using this sequence, but cleavage in the three consecutive arginine sequence was successfully inhibited. That is, cleavage by OmpT protease may be optimized for easier cleavage between arginine-alanine in -Arg-Arg-Arg-Ala-Arg↓Ala- (SEQ ID NO: 15) and Asp-Ala-Arg-Arg- Arg-Ala-Arg↓Ala- (SEQ ID NO: 16). It was thought that using these sequences (-Arg-Arg-Arg-Ala-Arg-Ala- (SEQ ID NO: 15) and Asp-Ala-Arg-Arg-Arg-Ala-Arg-Ala- (SEQ ID NO: 16)), and most preferably Asp-Ala-Arg-Arg-Arg-Ala-Arg-Ala- (SEQ ID NO: 16), would allow efficient cleavage even when the P1' position is an amino acid other than alanine.

Based on these results, motilin (with phenylalanine as the N-terminal amino acid) was examined as a target polypeptide to determine whether or not situating a physiologically active peptide in the amino acid sequence at the C-terminal end of the cleavage site -Arg-Arg-Arg-Ala-Arg↓Ala- (SEQ ID NO: 15) permits direct cleavage of the physiologically active peptide from a fusion protein with OmpT protease. Fusion protein PMT was constructed with motilin as the target polypeptide, and was reacted with OmpT protease in an attempt to cut off motilin.

However, it was shown that motilin is not efficiently cut off from the fusion protein PMT. This result suggested that, while the substrate specificity of OmpT protease is known to be tolerant with regard to the amino acid at position P1', more efficient cleavage requires introduction of a mutation into the protease itself to increase the specificity for the amino acid at position P1'.

Literature analyzing the crystal structure of OmpT has already been published (Vandeputte-Rutten, L. et al. EMBO J. 20: 5033-5039, 2001), and a related report (Kramer, R A. et al. FEBS Lett. 505: 426-430, 2001) suggests possible interaction between the P1' position amino acid of the substrate and the $Asp^{97}$ (97th position aspartic acid from the N-terminus) of OmpT protease. In order to investigate the change in substrate specificity that results by substitution of an amino acid at position 97, a plasmid was created for a mutant having $Asp^{97}$ of OmpT replaced with the 20 different amino acids (including synonymous substitution to aspartic acid), and these were introduced into OmpT-deficient *E. coli* BL21 to prepare 20 *E. coli* strains expressing the OmpT protease variants OmpT D97X (where X corresponds to the 20 amino acids).

In order to examine the P1' position substrate specificity of OmpT protease, these were reacted with the fusion protein PRX (where X corresponds to the 20 amino acids, see Japanese Patent Application No. 2000-602803) having the structure shown in FIG. 1, and cleavage of each fusion protein was investigated. As a result, the enzymes wherein the aspartic acid at position 97 of OmpT protease was replaced by alanine, leucine, phenylalanine, methionine, serine, threonine, cysteine, asparagine, glutamine, glutamic acid and histidine exhibited cleavage activity for the fusion proteins PRX, though with variation in cleavage efficiencies. In particular, the variant OmpT D97L exhibited high specificity for serine and alanine, OmpT D97M for phenylalanine, alanine, serine, cysteine and tyrosine, and OmpT D97H for alanine, valine, isoleucine, methionine, threonine, cysteine and asparagine.

Based on these findings, and considering that the N-terminal amino acid of motilin is phenylalanine, the aforementioned fusion protein PMT was reacted with OmpT D97M which exhibited good cleavage for phenylalanine at the P1' position, whereby it was possible to efficiently cut off motilin. That is, by optimizing the sequence adjacent to the cleavage site of OmpT protease and utilizing an OmpT protease variant, the present inventors succeeded in achieving cleavage with OmpT protease with which cleavage at desired sites has been difficult.

Also, in order to verify that the method is industrially applicable, fusion protein PMT-expressing *E. coli* and OmpT D97M protease variant-expressing *E. coli* were cultured at high density and the OmpT D97M protease variant-expressing *E. coli* itself was directly added to a reaction solution containing inclusion bodies prepared from the fusion protein PMT-expressing *E. coli*, and allowed to react at 25° C. for 1 hour. After adding 20 mM acetic acid (pH 4.0) to the reaction solution and removing the precipitate, the supernatant was supplied for cation-exchange and reverse-phase chromatography. This procedure allowed production of 160 mg per liter of fusion protein PMT-expressing *E. coli* culture solution, at a yield of 52% motilin with a purity of 99.0% or greater, which is an industrially acceptable level.

In order to confirm the general utility of this polypeptide production system, a fusion protein was prepared comprising human adrenocorticotropic hormone(1-24) (N-terminal amino acid: serine) as the target polypeptide and human calcitonin precursor (N-terminal amino acid: cysteine), and was treated with the OmpT protease variant. As a result, it was possible to obtain the desired target polypeptide in all cases, thus demonstrating the general utility of the system.

*E. coli* co-expressing the fusion protein PMT and OmpT D97M protease variant was prepared, and it was confirmed that human motilin can be released from the fusion protein PMT by simple dissolution in urea of inclusion bodies obtained by culturing the *E. coli*.

The specific experimental procedures not described in the examples provided below were as follows, unless otherwise specified.

(1) Construction of Expression Plasmids

Figure 10:
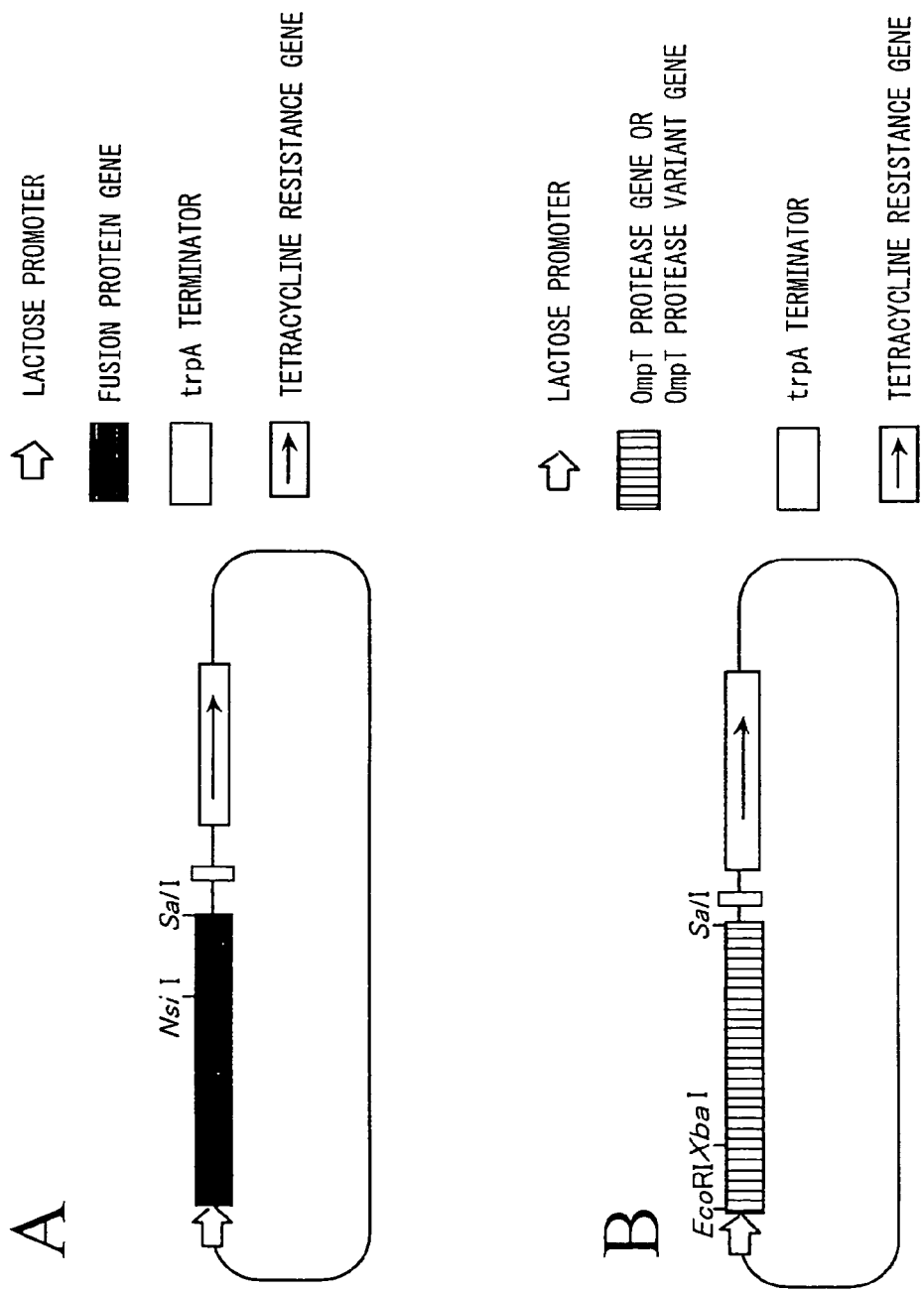
FIG. 10 shows (A) the structure of a fusion protein-expressing plasmid constructed for Examples 1, 3, 5, 7, 9, 16 and 18; and (B) the structure of an OmpT protease-or OmpT protease variant-expressing plasmid constructed for Example 11.
Figure 13:
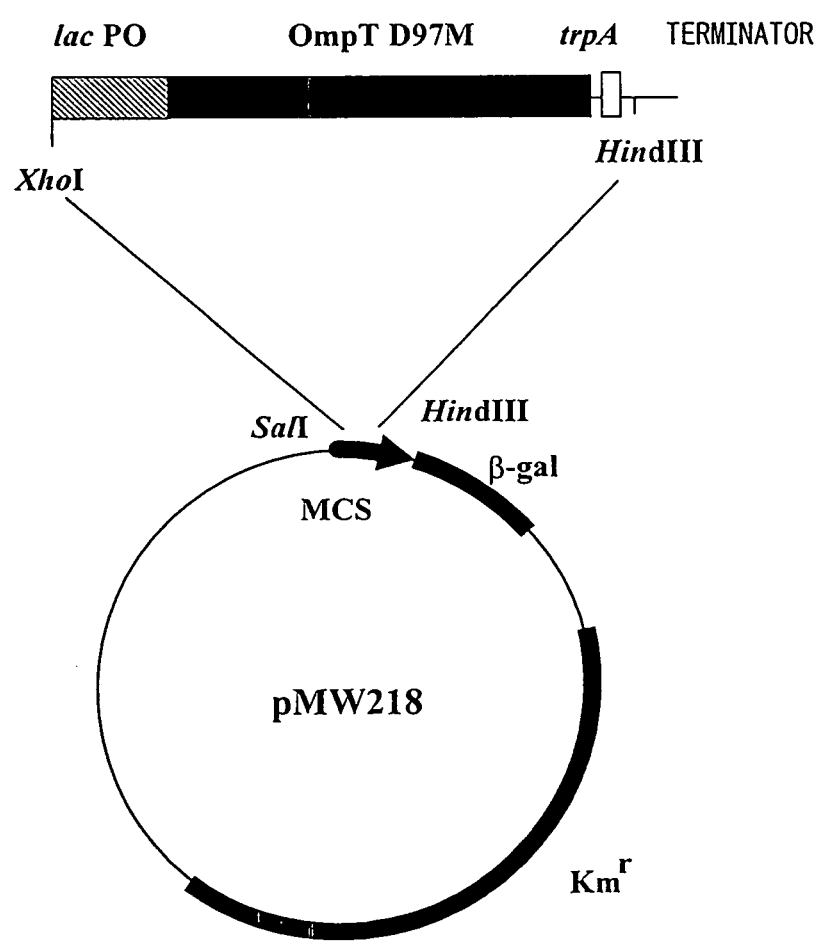
FIG. 13 shows the structure of the Ompt protease variant D97M-expressing plasmid constructed for Example 17. MCS is the multicloning site.

The expression plasmids were constructed by an ordinary protocol using *E. coli* JM109. Identity of the constructed expression plasmid as the target plasmid was confirmed by DNA sequence determination of the DNA region obtained by PCR for mutation introduction and the DNA region obtained by substitution with synthetic DNA. The structures of the plasmids constructed for Examples 1, 3, 5, 7, 9, 16 and 18 are shown in FIG. 10A, and the structure of the plasmid constructed for Example 11 is shown in FIG. 10B. The plasmid constructed for Example 17 is shown in FIG. 13.

(2) Assay of OmpT Protease Enzyme Activity

The OmpT protease activity was assayed using dynorphin A (Peptide Research Laboratory) as the substrate.

After adding 5 µL of 1 mg/mL dynorphin A to 40 µL of 50 mM sodium phosphate (pH 6.0) containing 0.1% Triton X-100, a 5 µL OmpT protease activity assay sample was added thereto and reaction was initiated. The reaction was performed at 25° C. for 10 minutes and terminated by addition of 5 µL of 1N HCl. The reaction solution was centrifuged at 10,000×g for 3 minutes, the supernatant was recovered, and 20 µL thereof was supplied for HPLC analysis.

The HPLC analysis was carried out using a YMC PROTEIN RP column, with a column temperature of 40° C. and a flow rate of 1 mL/min. After rinsing with 10% acetonitrile containing 0.1% trifluoroacetic acid for 3 minutes, elution was performed with a linear gradient of 10-15% acetonitrile containing 0.1% trifluoroacetic acid for 10 minutes. Absorption at 220 nm was monitored, and the decomposition product peptide Tyr-Gly-Gly-Phe-Leu-Arg (SEQ ID NO: 17) was detected. The OmpT protease activity upon cleavage of 1 µmol dynorphin A at 25° C. for 1 minute was defined as 1 unit.

(3) SDS-polyacrylamide Electrophoresis

The SDS-polyacrylamide electrophoresis used to investigate cleavage of the fusion protein employed 16% Peptide-PAGEmini by Tefco as the gel, Tricine electrophoresis buffer by Biorad as the electrophoresis buffer, and a protein molecular weight marker by Tefco or Biorad as the molecular weight marker. An equivalent of 2×SDS-PAGE sample buffer containing 4 M urea was added to the sample prior to heating at 100° C. for 5 minutes. A 10 μL portion was supplied for electrophoresis, and electrophoresis was carried out under the electrophoresis conditions indicated by Tefco. After electrophoresis, dyeing was performed with a dyeing solution containing Coumassie Brilliant Blue R-250.

(4) Preparation of Inclusion Bodies

In the examples, the fusion proteins were expressed as inclusion bodies in E. coli, and cleavage by OmpT protease occurs simply by dissolution of the obtained inclusion bodies in urea if the E. coli also express OmpT protease. In order to avoid cleavage, therefore, the OmpT protease-deficient E. coli strain W3110 M25 was transformed with the fusion protein-expressing plasmid, and each fusion protein was expressed as inclusion bodies. The W3110 M25 recombinant E. coli expressing each fusion protein was subjected to gyratory culture at 150 rpm, 37° C. overnight using 400 mL of LB liquid medium (0.5% (w/v) yeast extract, 1% (w/v) tryptone, 0.5% sodium chloride) containing 10 mg/L tetracycline in a 2 L Erlenmeyer flask.

On the following day, the cells were recovered by centrifugation at 4° C., 6000×g for 10 minutes, and then subjected to ultrasonication for cell disruption. Deionized water was added to the disrupted cells to 30 mL, and after centrifugation at 4° C., 25,000×g for 15 minutes the supernatant was discarded and the precipitated fraction (of inclusion bodies) was recovered. This was suspended in 30 mL of 50 mM Tris-HCl (pH 8.0), 5 mM EDTA, 1% Triton X-100 and centrifuged at 4° C., 25,000×g for 15 minutes to obtain a precipitate. The precipitate was suspended in 30 mL of deionized water and centrifuged at 4° C., 25,000×g for 15 minutes, and the precipitate was recovered. Deionized water was added thereto to 1.5 mL and the obtained suspension was centrifuged at 4° C., 10,000×g for 30 minutes to obtain a precipitate, and after repeating this procedure, the precipitate was suspended in deionized water to $OD_{660}$=100; the inclusion bodies prepared in this manner were used as substrate for OmpT protease reaction.

(5) OmpT Protease Reaction

OmpT protease reaction using the fusion protein as substrate was performed in the following manner. After adding 2.5 μL of 1 M sodium phosphate (pH 7.0) and 2 μL of 50 ml EDTA to 20 μL of 20 M urea, 10 μL of fusion protein inclusion bodies ($OD_{660}$=100) was added for lysis of the inclusion bodies. There was then added 10.5 μL of water, followed by 5 μL of 1.4 units/mL OmpT protease, and reaction was initiated with a reaction mixture volume of 50 μL. The reaction temperature was 25° C. and reaction was performed for 30 minutes.

Quantitation of the polypeptide obtained by reaction with OmpT protease was accomplished by HPLC under the following conditions, unless otherwise specified. The reaction was terminated by addition of 150 μL of 6% acetic acid, 2 M urea to the OmpT protease reaction mixture, and upon centrifugation at 10,000×g for 3 minutes, 20 μl of the supernatant was supplied to a YMC PROTEIN RP column. HPLC was carried out at a column temperature of 40° C. and a flow rate of 1 mL/min. Elution was performed with a linear gradient of 30-50% acetonitrile containing 0.1% trifluoroacetic acid for 20 minutes. Absorption at 214 nm was monitored for quantitation of the polypeptide.

(6) Mass Analysis of Polypeptide

In order to presume the cleavage site location, mass analysis of the polypeptide isolated by HPLC was carried out using SSQ710 by Thermo Finnigan.

(7) Preparation of E. coli Outer Membrane Fraction

An outer membrane fraction was prepared in the following manner for E. coli expressing OmpT protease or OmpT protease variant with W3110 M25 as the host cells, and the fraction was used as OmpT protease or OmpT protease variant for fusion protein cleavage reaction in Examples 10, 14, 16 and 18. The culturing method was performed as in (4) above, and upon completion of culturing, cells were obtained by centrifugation at 4° C., 6000×g for 10 minutes. The cells were suspended in 10 mM Tris-HCl (pH 8.0), 1 mM EDTA (TE), and disrupted by ultrasonication. The disrupted cells were centrifuged at 4° C., 1000×g for 10 minutes, the precipitate was discarded and the supernatant was recovered. It was then centrifuged at 4° C., 36,000×g for 40 minutes, and the precipitate was recovered, suspended in TE, and again centrifuged at 4° C., 36,000×g for 40 minutes. The obtained precipitate was suspended in TE to $OD_{660}$=10. It was stored at −20° C. until use.

EXAMPLES

The present invention will now be explained in greater detail through the following examples.

Example 1

Preparation of Fusion Proteins PAn

OmpT protease is an endoprotease found in E. coli outer membrane. Since the basic amino acids in the amino acid sequence adjacent to the cleavage site have a major effect on cleavage by this enzyme, the present inventors utilized the known cleavage site of the enzyme for the experiment described below to investigate the relationship between the basic amino acid position and the cleavage efficiency.

Figure 2:
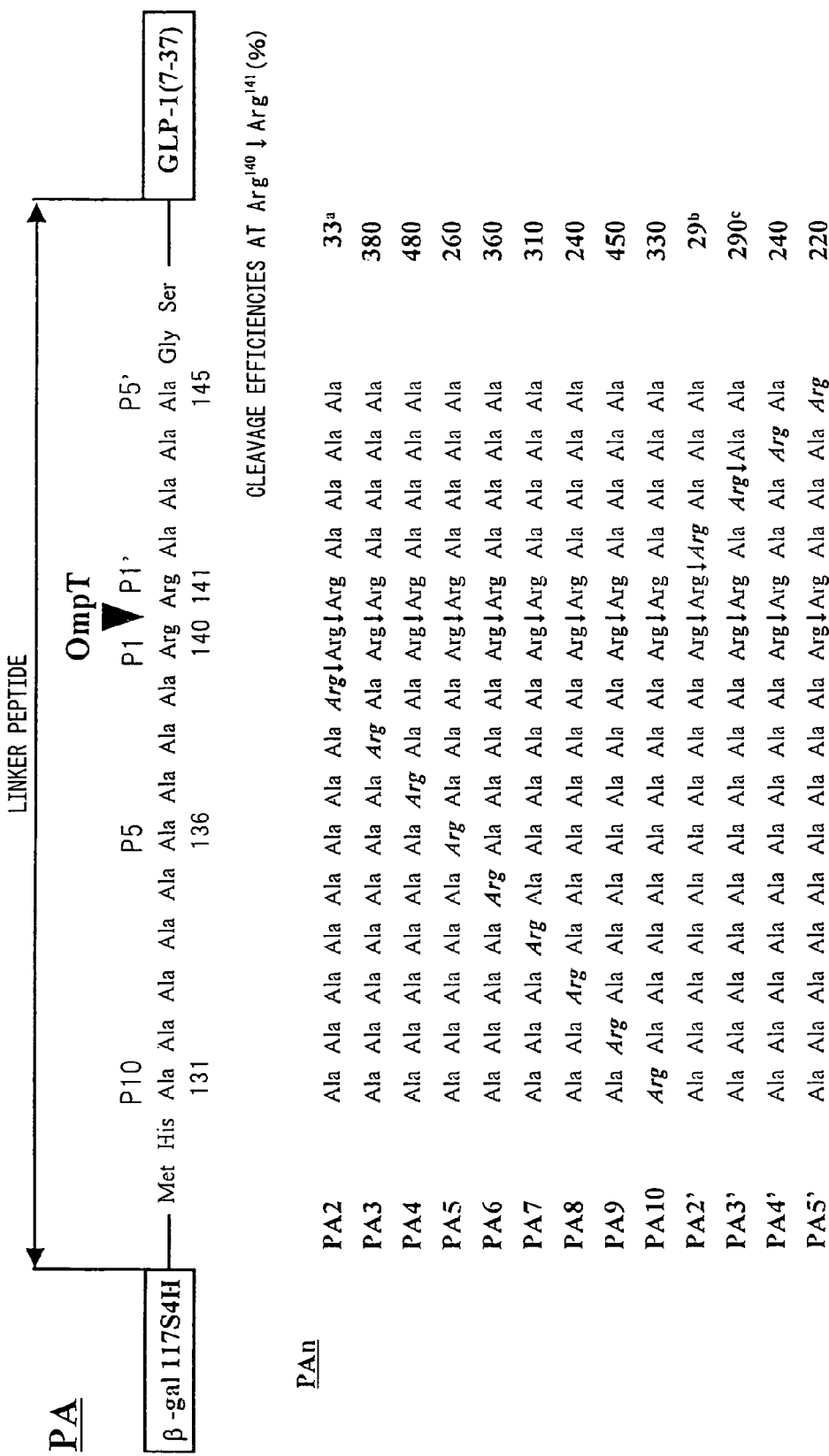
FIG. 2 is a diagram showing the structure of the fusion protein PAn. The position of each amino acid is shown on the amino acid sequence of the fusion protein PA, and the numbers below represent the amino acid sequence numbers from the N-terminus of PA. β-gal117S4H represents the protecting protein deriving from 117 amino acids from the N-terminus of *E. coli* β-galactosidase, GLP-1(7-37) represents human glucagon-like peptide-1(7-37), and the linker peptide is the portion from amino acid sequence No. 128 (glutamine) to No. 153 (arginine). The OmpT protease cleavage site on the fusion protein PA is indicated by a black wedge. The arginine residues introduced by amino acid substitution in the fusion protein PAn are indicated in bold italics. The OmpT protease cleavage site of PAn is indicated by ↓. At right are shown the cleavage efficiencies for each fusion protein, where the cleavage efficiency of the fusion protein PA is 100%. The letter "*a*" includes the cleavage efficiency at Arg$^{139}$-Arg$^{140}$. The letter "b" includes the cleavage efficiency at Arg$^{141}$-Arg$^{142}$. The letter "c" includes the cleavage efficiency at Arg$^{143}$-Ala$^{144}$. Figure discloses residues 129-147 of SEQ ID NO: 2, SEQ ID NOS: 18-27, residues 131-145 of SEQ ID NO: 3 and SEQ ID NOS: 28-29, respectively, in order of appearance.

Arginine was substituted for alanine at positions P10 to P2 and positions P2' to P5' of the cleavage site of the fusion protein PA (a fusion protein comprising the protecting protein deriving from 117 amino acids from the N-terminus of E. coli β-galactosidase (β-gal117S4H) and human glucagon-like peptide-1(7-37) (GLP-1(7-37) via a linker peptide) shown in FIG. 2 having a structure which is cleaved by OmpT protease, to create the fusion proteins PAn (FIG. 2: where n corresponds to the amino acid position [Pn] in the cleavage site, from P10 to P2 and from P2' to P5') having an altered OmpT protease cleavage site in the linker peptide, in order to examine cleavage by OmpT protease.

Plasmid pG117S4HompPRR (see Japanese Patent Application No. 2000-602803) having the structure shown in FIG. 10A, which is an expression plasmid for the fusion protein PRR (FIG. 1) having an arginine-arginine sequence inserted at the linker portion of the fusion protein as an E. coli OmpT protease recognition/cleavage site, was used as the basis for construction of plasmid pG117S4HompPA having the structure shown in FIG. 10A, which is a plasmid expressing the fusion protein PA, by site-directed mutagenesis and substitution with synthetic DNA. Also, the fusion protein PAn expression plasmid pG117S4HompPAn was constructed by introducing base substitutions by PCR into the fusion protein PA expression plasmid pG117S4HompPA having the structure shown in FIG. 2. The structure of the constructed plasmid is shown in FIG. 10A. The OmpT protease-deficient E. coli strain W3110 M25 was transformed with these fusion protein expression plasmids, and the fusion proteins were expressed as inclusion bodies.

Example 2

Cleavage of Fusion Proteins PAn by OmpT Protease

The cleavage efficiency by OmpT protease was examined using each fusion protein PAn (FIG. 2) wherein arginine was substituted for different alanines adjacent to the OmpT protease cleavage site of the fusion protein PA shown in FIG. 2, which has a structure that is cleaved by OmpT protease. Each PAn was reacted with an OmpT protease sample purified using Benzamidine Sepharose 6B at pH 7.0 according to Japanese Patent Application No. 2000-602803. FIG. 2 also shows the cleavage efficiencies obtained from the results of HPLC analysis after the enzyme reaction. FIG. 2 further shows the cleavage sites obtained from the results of mass analysis.

All of the PAn proteins underwent cleavage by OmpT protease at the same site as PA, while PA2, PA2' and PA3' also underwent cleavage at other sites (FIG. 2). In particular, PA3' was cleaved at the two sites $Arg^{140}$-$Arg^{141}$ and $Arg^{143}$-$Ala^{144}$ (cleavage efficiencies: 220%, 73%), thus indicating cleavage at a site other than consecutive basic amino acids ($Arg^{143}$-$Ala^{144}$).

Increase in cleavage efficiency was seen for all of the PAn proteins except for PA2 and PA2', suggesting that the cleavage efficiency can be improved by situating arginine at positions P10 to P3 and positions P3' to P5' of the amino acid sequence adjacent to the cleavage site. Among these, PA4 had the highest cleavage efficiency of about 5 times that of PA, and therefore substitution of arginine at position P4 was shown to be most effective. On the other hand, the cleavage efficiencies of PA2 and PA2' were reduced to about ⅓, indicating that the cleavage efficiency is reduced with a sequence of three consecutive arginines.

Example 3

Preparation of Fusion Proteins PA1A3' PA1'A3'

OmpT protease is known to be an enzyme which cleaves primarily between consecutive basic amino acids. However, the results of Example 2 demonstrated that the fusion protein PA3' is cleaved at two sites: $Arg^{140}$-$Arg^{141}$ and $Arg^{143}$-$Ala^{144}$, and that one of them is -Arg↓Ala-cleavage. The cleavage efficiency at -Arg↓Ala- is low compared to the cleavage efficiency between basic amino acids, but it was speculated that this could be improved to an industrially useful cleavage efficiency.

Therefore, in order to inhibit cleavage at $Arg^{140}$-$Arg^{141}$ among the two cleavage sites $Arg^{140}$-$Arg^{141}$ and $Arg^{143}$-$Ala^{144}$ of the fusion protein PA3', there were prepared fusion proteins PA1A3' and PA1'A3' (FIG. 3) having an amino acid sequence with alanine substituting for $Arg^{140}$ or $Arg^{141}$, and their cleavage with OmpT protease was examined. It was also investigated whether $Arg^{140}$ (position P4, where $Arg^{143}$ and $Ala^{144}$ are positions P1 and P1', respectively) and $Arg^{141}$ (position P3, where $Arg^{143}$ and $Ala^{144}$ are positions P1 and P1', respectively) are necessary for cleavage at $Arg^{143}$-$Ala^{144}$ using these fusion proteins.

Figure 3:
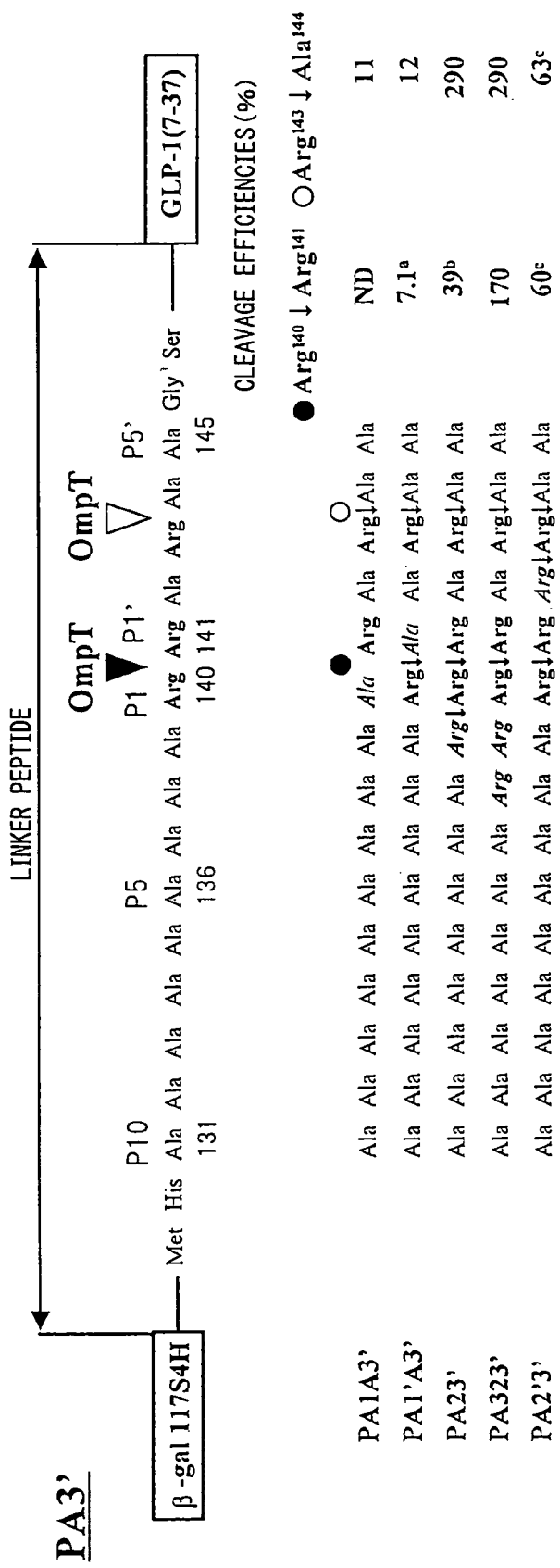
FIG. 3 shows the structures of the fusion proteins PA1A3' (SEQ ID NO:30), PA1'A3' (SEQ ID NO: 31), PA23' (Residues 131-145 of SEQ ID NO:4), PA323'(SEQ ID NO: 32) and PA2'3' (SEQ ID NO: 33). The position of each amino acid is shown on the amino acid sequence of the fusion protein PA3' (Residues 129-147 of SEQ ID NO:3), and the numbers below represent the amino acid sequence numbers from the N-terminus of PA3'. β-gal117S4H represents the protecting protein deriving from 117 amino acids from the N-terminus of E. coli β-galactosidase, GLP-1(7-37) represents human glucagon-like peptide-1(7-37), and the linker peptide is the portion from amino acid sequence No. 128 (glutamine) to No. 153 (arginine). Arginine residues are shown in bold. The OmpT protease cleavage sites of the fusion protein PA3' are represented by open triangle (cleavage efficiency: 73%) and solid triangle (cleavage efficiency: 220%). The residues introduced by amino acid substitution in PA3' for the fusion proteins PA1A3', PA1'A3', PA23', PA323' and PA2'3' are shown in italics, and the OmpT protease cleavage site is indicated by ↓. At right are shown the cleavage efficiencies for the Arg$^{140}$-Arg$^{141}$ site (filled circles) and the Arg$^{143}$-Ala$^{144}$ site (open circles) in each fusion protein, where the cleavage efficiency of the fusion protein PA is 100%. ND stands for "not detected". The letter "a" represents the cleavage efficiency at Arg$^{140}$-Arg$^{141}$. The letter "b" the cleavage efficiency at Arg$^{139}$-Arg$^{140}$. The letter "c" includes the cleavage efficiency at Arg$^{142}$-Ala$^{143}$.

The fusion protein PA1A3' and PA1'A3' expression plasmids pG117S4HompPA1A3' and pG117S4HompPA1'A3' were constructed by introducing base substitutions by PCR into the fusion protein PA3' expression plasmid pG117S4HompPA3', having the structure shown in FIG. 3. The structures of the constructed plasmids are shown in FIG. 10A. The OmpT protease-deficient E. coli strain W3110 M25 was transformed with the fusion protein-expressing plasmids, and each fusion protein was expressed as inclusion bodies.

Example 4

Cleavage of Fusion Proteins PA1A3' and PA1'A3' with OmpT Protease

The cleavage sites and cleavage efficiencies with OmpT protease were investigated for the fusion proteins PA1A3' and PA1'A3' shown in FIG. 3. PA1A3' and PA1'A3' were reacted with an OmpT protease sample purified using Benzamidine Sepharose 6B at pH 7.0 according to Japanese Patent Application No. 2000-602803. FIG. 3 also shows the cleavage efficiencies obtained from the results of HPLC analysis after the enzyme reaction, as well as the cleavage sites obtained from the results of mass analysis. PA1A3' and PA1'A3' were both cleaved at $Arg^{143}$-$Ala^{144}$.

However, all of the cleavage efficiencies were lower than the cleavage efficiency at $Arg^{140}$-$Arg^{141}$ of PA. Cleavage was also confirmed at $Arg^{140}$-$Ala^{141}$ in PA1'A3'. If $Arg^{143}$-$Ala^{144}$ is considered as the cleavage site P1-P1', this suggests that cleavage at $Arg^{143}$-$Ala^{144}$ occurs so long as arginine is present at position P3 ($Arg^{141}$ in PA1A3') or arginine is present at position P4 ($Arg^{140}$ in PA1'A3'), but that PA3' with arginine situated at both positions P4 and P3 has a higher cleavage efficiency than PA1A3' and PA1'A3'.

Example 5

Preparation of Fusion Proteins PA23' PA323' and PA2'3'

The results of Example 4 demonstrated that the fusion proteins PA1A3' and PA1'A3' are cleaved at $Arg^{143}$-$Ala^{144}$, and notably only at $Arg^{143}$-$Ala^{144}$ in PA1A3', but the cleavage efficiencies were low. Thus, amino acid substitutions were introduced into the fusion protein PA3' in order to design an amino acid sequence with an increased cleavage efficiency at -Arg↓Ala- ($Arg^{143}$-$Ala^{144}$). Based on the results of Example 2, the fusion proteins PA23', PA323' and PA2'3' (FIG. 3) were prepared in the following manner, having an amino acid sequence (with 3 or 4 consecutive arginines instead of 2 consecutive arginines) which was expected to increase the cleavage efficiency at -Arg↓Ala- ($Arg^{143}$-$Ala^{144}$) and decrease the cleavage efficiency between consecutive basic amino acids ($Arg^{140}$-$Arg^{141}$), and their cleavage with OmpT protease was investigated.

The fusion protein PA23' and PA2'3' expression plasmids pG117S4HompPA23' and pG117S4HompPA2'3' were constructed by introducing base substitutions by PCR into the fusion protein PA3' expression plasmid pG117S4HompPA3' having the structure shown in FIG. 3. Also, the fusion protein PA3231 expression plasmid pG117S4HompPA323' was constructed by introducing a base substitution by PCR into the fusion protein PA23' expression plasmid pG117S4HompPA23' having the structure shown in FIG. 3. The structures of the constructed plasmids are shown in FIG. 10A. The OmpT protease-deficient E. coli strain W3110 M25 was transformed with the fusion protein-expressing plasmids, and each fusion protein was expressed as inclusion bodies.

Example 6

Cleavage of Fusion Proteins PA23', PA323' and PA2'3' with OmpT Protease

The cleavage sites and cleavage efficiencies with OmpT protease were investigated for the fusion proteins PA23', PA323' and PA2'3' shown in FIG. 3. PA23', PA323' and PA2'3' were reacted with an OmpT protease sample purified using Benzamidine Sepharose 6B at pH 7.0 according to Japanese Patent Application No. 2000-602803, at 25° C. for 30 minutes. FIG. 3 also shows the cleavage efficiencies obtained from the results of HPLC analysis after the enzyme reaction, as well as the cleavage sites obtained from the results of mass analysis. It was confirmed that PA23', PA323' and PA2'3' are cleaved at $Arg^{143}$-$Ala^{144}$. The cleavage efficiency at $Arg^{143}$-$Ala^{144}$ of PA23' was 2.9 times the cleavage efficiency at $Arg^{140}$-$Arg^{141}$ of PA.

Cleavage was also observed at $Arg^{139}$-$Arg^{140}$ and $Arg^{140}$-$Arg^{141}$, but was 13% of the cleavage efficiency at $Arg^{143}$-$Ala^{144}$. The cleavage efficiency at $Arg^{143}$-$Ala^{144}$ of PA323' was also 2.9 times the cleavage efficiency at $Arg^{140}$-$Arg^{141}$ of PA, but cleavage was also observed at $Arg^{140}$-$Arg^{141}$, at 59% the cleavage efficiency at $Arg^{143}$-$Ala^{144}$. In PA2'3', the cleavage efficiency at $Arg^{143}$-$Ala^{144}$ was low at 63% of the cleavage efficiency at $Arg^{140}$-$Arg^{141}$ of PA, and cleavage at $Arg^{140}$-Arg and $Arg^{142}$-$Arg^{143}$ was also confirmed. This indicated that among these three fusion proteins, PA23' has the optimum sequence for increasing the cleavage efficiency at -Arg↓Ala- ($Arg^{143}$-$Ala^{144}$) and decreasing the cleavage efficiency between consecutive basic amino acids.

Example 7

Preparation of Fusion Proteins PA5D23' PA4D23' and PA3D23'

The results of Example 6 demonstrated that the cleavage efficiency at $Arg^{143}$-$Ala^{144}$ in the fusion protein PA23' is very high. However, cleavage was also confirmed at $Arg^{139}$-$Arg^{140}$ and $Arg^{140}$-$Arg^{141}$. Thus, since cleavage is presumably inhibited when acidic amino acids are present near the cleavage site, there were prepared in the following manner fusion proteins PA5D23', PA4D23' and PA3D23' (FIG. 4) having aspartic acid substituted at Ala 13, Ala 13 and $Ala^{138}$ in order to inhibit cleavage at $Arg^{139}$-$Arg^{140}$ and $Arg^{140}$-$Arg^{141}$, and their cleavage by OmpT protease was investigated.

Figure 4:
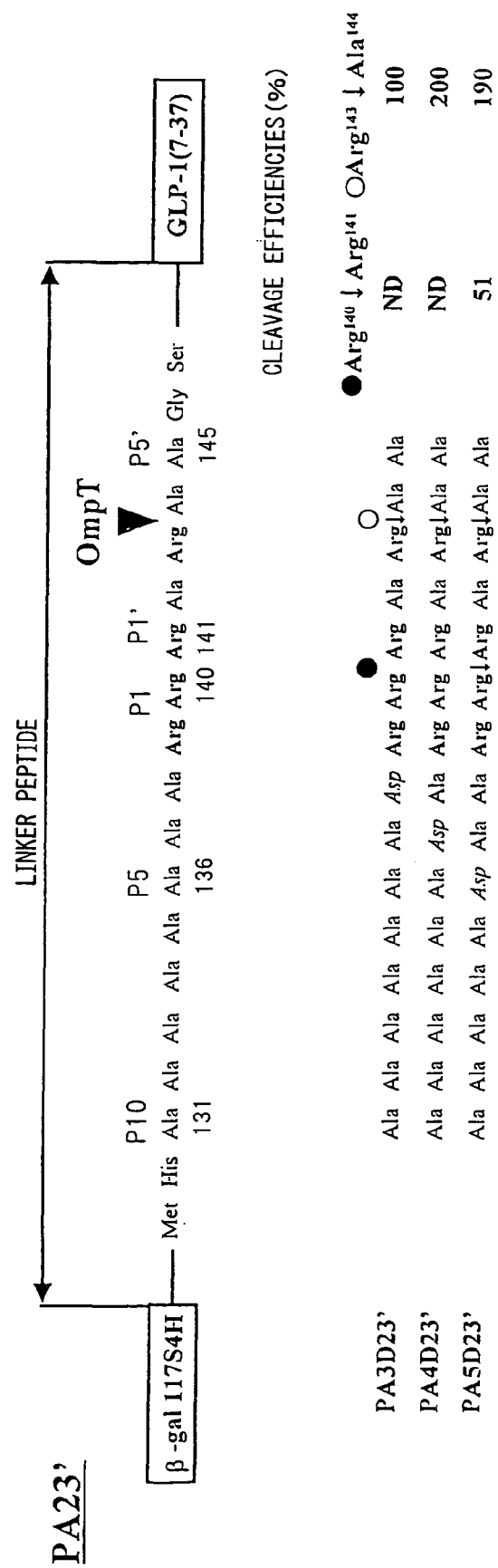
FIG. 4 shows the structures of the fusion proteins PA3D23' (SEQ ID NO: 34), PA4D23' (SEQ ID NO:35) and PA5D23' (SEQ ID NO: 36). The position of each amino acid is shown on the amino acid sequence of the fusion protein PA23' (Residues 129-147 of SEQ ID NO:4), and the numbers below represent the amino acid sequence numbers from the N-terminus of PA23'. β-gal117S4H represents the protecting protein deriving from 117 amino acids from the N-terminus of E. coli β-galactosidase, GLP-1(7-37) represents human glucagon-like peptide-1(7-37), and the linker peptide is the portion from amino acid sequence No. 128 (glutamine) to No. 153 (arginine). Arginine residues are shown in bold. The main OmpT protease cleavage site of the fusion protein PA23' is represented by a black wedge. The residues introduced by amino acid substitution in PA23' for the fusion proteins PA3D23', PA4D23', PA5D23' and PA23' are shown in italics, and the OmpT protease cleavage site is indicated by ↓. At right are shown the cleavage efficiencies for the Arg$^{140}$-Arg$^{141}$ site (filled circles) and the Arg$^{143}$-Ala$^{144}$ site (open circles) in each fusion protein, where the cleavage efficiency of the fusion protein PA is 100%. ND stands for "not detected".

The fusion protein PA5D23', PA4D23' and PA3D23' expression plasmids pG117S4HompPA5D23', pG117S4HompPA4D23' and PG117S4HompPA3D23' were constructed by introducing base substitutions by PCR into the fusion protein PA23' expression plasmid pG117S4HompPA23', having the structure shown in FIG. 4. The structures of the constructed plasmids are shown in FIG. 10A. The OmpT protease-deficient *E. coli* strain W3110 M25 was transformed with the fusion protein-expressing plasmids, and each fusion protein was expressed as inclusion bodies.

Example 8

Cleavage of Fusion Proteins PA5D23' PA4D23' and PA3D23' with OmpT Protease

The cleavage sites and cleavage efficiencies with OmpT protease were investigated for the fusion proteins PA5D23', PA4D23' and PA3D23' shown in FIG. 4. PA5D23', PA4D23' and PA3D23' were reacted with an OmpT protease sample purified using Benzamidine Sepharose 6B at pH 7.0 according to Japanese Patent Application No. 2000-602803, at 25° C. for 30 minutes. FIG. 4 also shows the cleavage efficiencies obtained from the results of HPLC analysis after the enzyme reaction, as well as the cleavage sites obtained from the results of mass analysis. It was confirmed that the major cleavage site of PA5D23', PA4D23' and PA3D23' is $Arg^{143}$-$Ala^{144}$.

In particular, the cleavage efficiency at $Arg^{143}$-$Ala^{144}$ of PA4D23' was low compared to PA23', but twice the cleavage efficiency at $Arg^{140}$-$Arg^{141}$ of PA. On the other hand, no cleavage was detected at $Arg^{139}$-$Arg^{140}$ and $Arg^{140}$-$Arg^{141}$ as was detected with PA23'. That is, if $Arg^{140}$-$Arg^{141}$ is considered as P1-P1', its cleavage was likely inhibited by the aspartic acid at position P3. Similarly, if $Arg^{139}$-$Arg^{140}$ is considered as P1-P1', its cleavage was likely inhibited by the aspartic acid at position P2. The cleavage efficiency at $Arg^{143}$-$Ala^{144}$ of PA5D23' was also 1.9 times the cleavage efficiency at $Arg^{140}$-$Arg^{141}$ of PA, but cleavage was also observed at $Arg^{140}$-$Arg^{141}$.

For PA3D23', no cleavage was detected at $Arg^{139}$-$Arg^{140}$ and $Arg^{140}$-$Arg^{141}$, similar to PA4D23'. That is, if $Arg^{140}$-$Arg^{141}$ is considered as P1-P1', its cleavage was likely inhibited by the aspartic acid at position P4. Similarly, if $Arg^{139}$-$Arg^{140}$ is considered as P1-P1', its cleavage was likely inhibited by the aspartic acid at position P3. However, the cleavage efficiency at $Arg^{143}$-$Ala^{144}$ was about the same as the cleavage efficiency at $Arg^{140}$-$Arg^{141}$ of PA, and lower than PA4D23'. This indicated that among these three fusion proteins, PA4D23' has the optimum sequence for increasing the cleavage efficiency at -Arg↓Ala- ($Arg^{143}$-$Ala^{144}$) and decreasing the cleavage efficiency between consecutive basic amino acids.

This suggests the possibility that when OmpT protease is used to cut off a target polypeptide, wherein the N-terminal amino acid is any of the 17 amino acids other than aspartic acid, glutamine and proline, from a fusion protein having the structure: protecting protein-linker peptide-target polypeptide, specific cleavage is possible by situating the target polypeptide after the C-terminal of the amino acid sequence -Asp-Ala-Arg-Arg-Arg-Ala-Arg- (SEQ ID NO: 12).

Example 9

Preparation of Fusion Proteins PRMT and PMT

The results in Example 6 indicated that OmpT protease can efficiently cleave -Arg↓Ala- in the amino acid sequence adjacent to the cleavage site of this enzyme in the fusion protein PA23' shown in FIG. 3. Based on these results, it was predicted that efficient cleavage should be possible even with a cleavage site -ArgXaa-(where Xaa is any of the 17 amino acids other than the acidic amino acids aspartic acid and glutamine, or proline). The present inventors therefore examined how cleavage by this enzyme is affected when the N-terminus following the arginine at position 143 of the fusion protein PA23' used in Example 6 is an amino acid other than an acidic amino acid or proline, and is replaced with an amino acid other than a basic amino acid.

First, fusion protein PRMT (FIG. 5) was constructed as a control, having human motilin situated following arginine at position 140 from the N-terminus of the fusion protein PRR (see Japanese Patent Application No. 2000-602803) having the structure shown in FIG. 1, which is cleaved at $Arg^{140}$-$Arg^{141}$ by OmpT protease. Next, fusion protein PMT (FIG. 5) was constructed having human motilin situated following arginine at position 143 from the N-terminus of the fusion protein PA23' (FIGS. 3 and 4).

The structures of the fusion protein PRMT expression plasmid pG117S4HompPRMT and the PMT expression plasmid pG117S4HompPMT are shown in FIG. 10A. The OmpT protease-deficient *E. coli* strain W3110 M25 was transformed with the two fusion protein-expressing plasmids, to create fusion protein-producing strains. The obtained bacterial strains were cultured and the fusion proteins PRMT and PMT were prepared as inclusion bodies.

Example 10

Cleavage of Fusion Proteins PRMT and PMT by OmpT Protease

Figure 5:
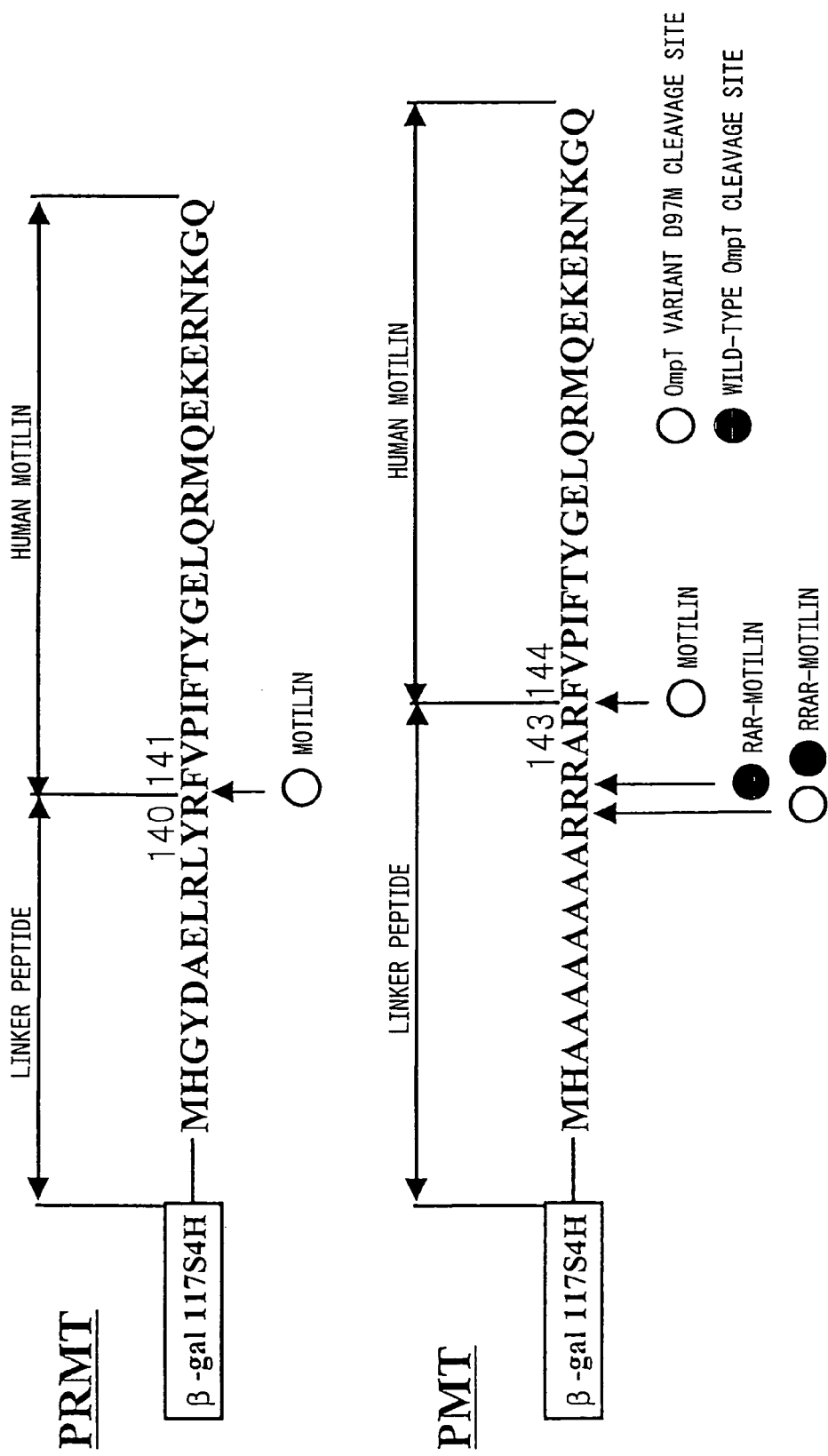
FIG. 5 shows the structures of the fusion proteins PRMT (Residues 129-162 of SEQ ID NO: 5) and PMT (Residues 129-165 of SEQ ID NO: 6). The numbers over the amino acid sequences of the fusion proteins represent the amino acid sequence numbers from the respective N-terminus. β-gal117S4H represents the protecting protein deriving from 117 amino acids from the N-terminus of E. coli β-galactosidase, and the linker peptide is the portion from amino acid sequence No. 128 (glutamine) to No. 143 (arginine) in PRMT or from amino acid sequence No. 128 (glutamine to No. 143 (arginine) in PMT. The amino acid sequence up to arginine at position 140 of the fusion protein PRMT matches the amino acid sequence up to arginine at position 140 from the N-terminus of the fusion protein PRR (see Japanese Patent Application No. 2000-602803) whose structure is shown in FIG. 1. Also, the amino acid sequence up to the arginine at position 143 of the fusion protein PMT matches the amino acid sequence up to arginine at position 143 from the N-terminus of the fusion protein PA23' (FIG. 4). The OmpT protease cleavage site of the fusion protein PMT is indicated by filled circles, and the OmpT protease variant D97M cleavage site is indicated by open circles. RAR-motilin is a polypeptide comprising Arg-Ala-Arg-motilin released from PMT by cleavage at Arg$^{140}$-Arg$^{141}$, and RRAR-motilin (SEQ ID NO: 13) is a polypeptide comprising Arg-Arg-Ala-Arg-motilin (SEQ ID NO: 13) released from PMT by cleavage at Arg$^{139}$-Arg$^{140}$.

Cleavage of the fusion proteins PRMT and PMT shown in FIG. 5 by OmpT protease was examined by SDS-PAGE and HPLC using the membrane fraction of OmpT protease-expressing *E. Coli*, with W3110 M25 as the host cells. In SDS-PAGE, cleavage of the fusion protein PMT by OmpT protease was confirmed but no cleavage of PRMT was detected. HPLC also confirmed cleavage of the fusion protein PMT, but it was cleavage primarily between the basic amino acids $Arg^{139}$-$Arg^{140}$ or $Arg^{140}$-$Arg^4$, whereas only a very slight amount of peptide cleavage fragment of $Arg^{143}$-$Phe^{144}$, i.e. human motilin, was detected by mass analysis.

This demonstrated that human motilin cannot be cut off at the primary peptide cleavage site by OmpT protease, simply by using -Arg-Arg-Arg-Ala-Arg-motilin (SEQ ID NO: 11) as the amino acid sequence adjacent to the cleavage site. It was thus suggested that, while the substrate specificity of this protease is tolerant with regard to the amino acid at position P1', more efficient cleavage requires introduction of a mutation into the protease itself, to increase the specificity for the amino acid at position P1'. Thus, an OmpT protease variant was created and it was examined whether or not primarily human motilin can be cut off from the fusion protein using it.

Example 11

Preparation of OmpT protease variant-expressing *E. coli*

It being noted that literature analyzing the crystal structure of OmpT protease (Vandeputte-Rutten, L. et al. EMBO J. 20: 5033-5039, 2001) and a related report (Kramer, R A. et al. FEBS Lett. 505: 426-430, 2001) suggest possible interaction between the P1' position amino acid of the substrate and $Asp^{97}$ of OmpT protease, a plasmid was created having $Asp^{97}$ of OmpT protease replaced with the 20 different amino acids (including synonymous substitution to aspartic acid) using PCR in the manner described below, and these were introduced into OmpT-deficient *E. coli* BL21 to prepare 20 *E. coli* strains expressing OmpT protease variants.

In order to facilitate introduction of mutations at $Asp^{97}$ of OmpT protease and minimize the DNA region amplified by PCR, first there was constructed an OmpT protease-expressing plasmid pOmpTXbaI, having an XbaI restriction endonuclease site introduced by using PCR for substitution of TCT for the AGT coding for $Ser^{99}$ of OmpT protease in the OmpT protease-expressing plasmid pOmpTTcE (see Japanese Patent Application No. 2000-602803) which has the structure shown in FIG. 10B. Next, plasmids pOmpTD97X expressing the variants OmpT D97X (where X represents one of the substituted 20 amino acids) having the 20 amino acids substituting for $Asp^{97}$ of OmpT protease (including synonymous substitution to aspartic acid) were constructed by introducing mutations into the OmpT protease-expressing plasmid pOmpTXbaI using PCR. The structures of the expression plasmids pOmpTXbaI and pOmpTD97X are shown in FIG. 10B.

The resulting twenty expression plasmids pOmpTD97X were each transferred into OmpT protease-deficient *E. coli* BL21 to prepare 20 *E. coli* strains expressing the OmpT protease variants OmpT D97X. The *E. coli* strains were shake cultured to about $OD_{660}$=1 in a test tube at 37° C. using 2 mL of LB broth containing 10 µg/mL tetracycline, and then the cells were recovered by centrifugation. Next, 1 mL of TE (10 mM Tris-HCl, 1 mM EDTA, pH 8.0) was added thereto for suspension, and the cells were recovered by centrifugation. Also, the same procedure was repeated to obtain cells to which TE was added to $OD_{660}$=2 to form suspensions for use as cell suspensions for reaction of the OmpT protease variants OmpT D97X. The cell suspensions were stored at −20° C. until use.

Example 12

Confirmation of OmpT Protease Variant Expression Levels in OmpT Protease Variant-Expressing *E. coli* Cell Suspensions In order to confirm that the expression levels of OmpT protease variants in the OmpT protease variant-expressing *E. coli* cell suspensions were all equivalent in the cell suspensions, anti-OmpT protease antibody was used for Western blotting and immunostaining. The anti-OmpT protease antibody was prepared by immunosensitizing rabbits with purified OmpT protease, purifying the IgG fraction from the antiserum, and recovering from it the fraction with affinity for purified OmpT protease.

The cell suspension corresponding to $OD_{660}$=0.01 per lane was supplied for 12% SDS-PAGE, and after completion of electrophoresis, a PVDF membrane was used for Western blotting. The purified transfer membrane was immersed in blocking solution (5% (w/v) skim milk/1×TBST*) and shaken for 30 minutes at room temperature. Next, the membrane was immersed in a 1000-fold dilution of anti-OmpT protease antibody in blocking solution, and shaken for 100 minutes at room temperature. The solution was discarded, and washing was performed three times with 1×TBST* for 5 minutes. The membrane was then immersed in peroxidase-bound anti-rabbit IgG antibody solution diluted 1000-fold with blocking solution, and shaken for 45 minutes at room temperature.

After washing 4 times with 1×TBST* for 10 minutes, detection was performed with an ECL kit (Amersham Pharmacia). No band was detected for the OmpT protease-deficient *E. coli* BL21 host cells while a band was detected for the other cell suspensions at approximately the same intensity, thus indicating that the expression level of OmpT protease variant in the OmpT protease variant-expressing *E. coli* cell suspension was probably approximately equal in all of the cell suspensions. (*1×TBST=10 mM Tris-HCl (pH 7.0), 150 mM NaCl, 0.05% Tween 20).

Example 13

Investigation of P1' Position Substrate Specificity of OmpT Protease Variants OmpT D97X Because OmpT protease is present on the *E. coli* outer membrane, it can be reacted with substrate by simple addition of the cells to the reaction solution. Thus, in order to determine the P1' position substrate specificity of the OmpT protease variants OmpT D97X, the fusion proteins PRX (see Japanese Patent Application No. 2000-602803) having the structures shown in FIG. 1 were used as substrates, and the reactivities with the OmpT protease variants OmpT D97X were examined, in the following manner. After adding 2.5 µL of 1 M sodium phosphate (pH 7.0) and 2 µL of 50 mM EDTA to 20 µL of 10 M urea, 5 µL of fusion protein inclusion bodies ($OD_{660}$=100) were added for lysis of the inclusion bodies.

Next, 10.5 µL of water was added thereto, 10 µL of the OmpT protease variant-expressing *E. coli* cell suspension prepared in Example 11 was further added, and reaction was initiated at a reaction solution volume of 50 µL. The reaction was performed at 25° C. for 60 minutes. Quantitation of the peptide fragments obtained by the reaction was accomplished by HPLC under the same conditions as for the OmpT protease reaction. The results are shown in Table 1.

proteins PRR and PRK, by D97L for PRS, by D97M for PRF and PRY, and by D97H for PRA, PRV, PRI, PRM, PRT, PRC and PRN. Among these, the D97M variant which had high specificity for PRF was used for reaction with the fusion proteins PRMT and PMT prepared in Example 9, to examine its ability to cut off human motilin.

Example 14

Liberation Human Motilin from Fusion Protein PMT by OmpT Protease D97M Variant Liberation of human motilin from the human motilin fusion proteins PRMT and PMT (FIG. 5) by the OmpT protease D97M variant was investigated using outer membrane fractions of *E. coli* expressing wild-type OmpT protease (D97D) and the OmpT protease variant D97M, with W3110 M25 as the host cells. After adding 2.5 µL of 1 M sodium phosphate (pH 7.0) and 2 µL of 50 mM EDTA to 20 µL of 10 M urea, 10 µL of fusion protein inclusion bodies ($OD_{660}$=100) was added for lysis of the inclusion bodies. There was then added 10.5 µL of water, followed by 5 µL of recombinant *E. coli* outer membrane fraction, and reaction was initiated with a reaction solution volume of 50 µL. The reaction temperature was 25° C. and reaction was performed for 120 minutes.

TABLE 1

Cleavage of fusion proteins PRX with OmpT protease variants OmpT D97X

| Fusion proteins PRX | OmpT protease variants OmpT D97X | | | | | | | | | | | |
|---|---|---|---|---|---|---|---|---|---|---|---|---|
| | D97D | D97A | D97L | D97F | D97M | D97S | D97T | D97C | D97N | D97Q | D97E | D97H |
| PRA | 5.4 | 3.8 | 7.1 | 3.1 | 6.0 | 4.0 | 6.8 | 6.2 | 3.8 | 4.0 | 6.5 | 8.4 |
| PRV | 3.5 | — | — | — | 3.0 | — | — | 3.2 | — | — | 5.0 | 7.8 |
| PRI | — | — | — | — | — | — | — | — | — | — | — | 3.1 |
| PRF | — | — | 4.7 | — | 7.7 | — | 3.7 | 4.6 | — | — | 3.4 | 4.1 |
| PRM | — | — | — | — | — | — | — | — | — | — | — | 4.6 |
| PRS | 3.9 | — | 9.1 | — | 7.1 | — | 7.4 | 5.6 | 4.1 | 4.4 | 7.2 | 8.7 |
| PRT | — | — | — | — | — | — | — | — | — | — | — | 3.0 |
| PRC | 3.1 | — | 3.9 | — | 6.5 | 3.1 | 4.6 | 4.8 | — | 4.1 | 6.9 | 11 |
| PRY | — | — | 3.2 | — | 6.2 | — | — | — | — | — | — | — |
| PRN | — | — | — | — | — | — | — | — | — | — | — | 3.5 |
| PRK | 88 | — | — | — | — | — | — | 3.9 | — | — | 39 | 4.5 |
| PRR | 100 | — | — | — | — | — | — | 4.0 | — | — | 49 | 4.6 |

The cleavage efficiencies are expressed relative to 100% as the cleavage efficiency for reaction between the wild-type OmpT protease (D97D) and the fusion protein PRR. The symbol "—" represents a relative cleavage efficiency of less than 3.0%. The OmpT protease variants D97V, D97I, D97P, D97W, D97G, D97Y, D97K and D97R had relative cleavage efficiencies of less than 3.0% for all of the twenty amino fusion proteins PRX. The fusion proteins PRL, PRP, PRW, PRG, PRQ, PRD, PRE and PRH had relative cleavage efficiencies of less than 3% by all of the OmpT protease variants OmpT D97X.

Figure 6:
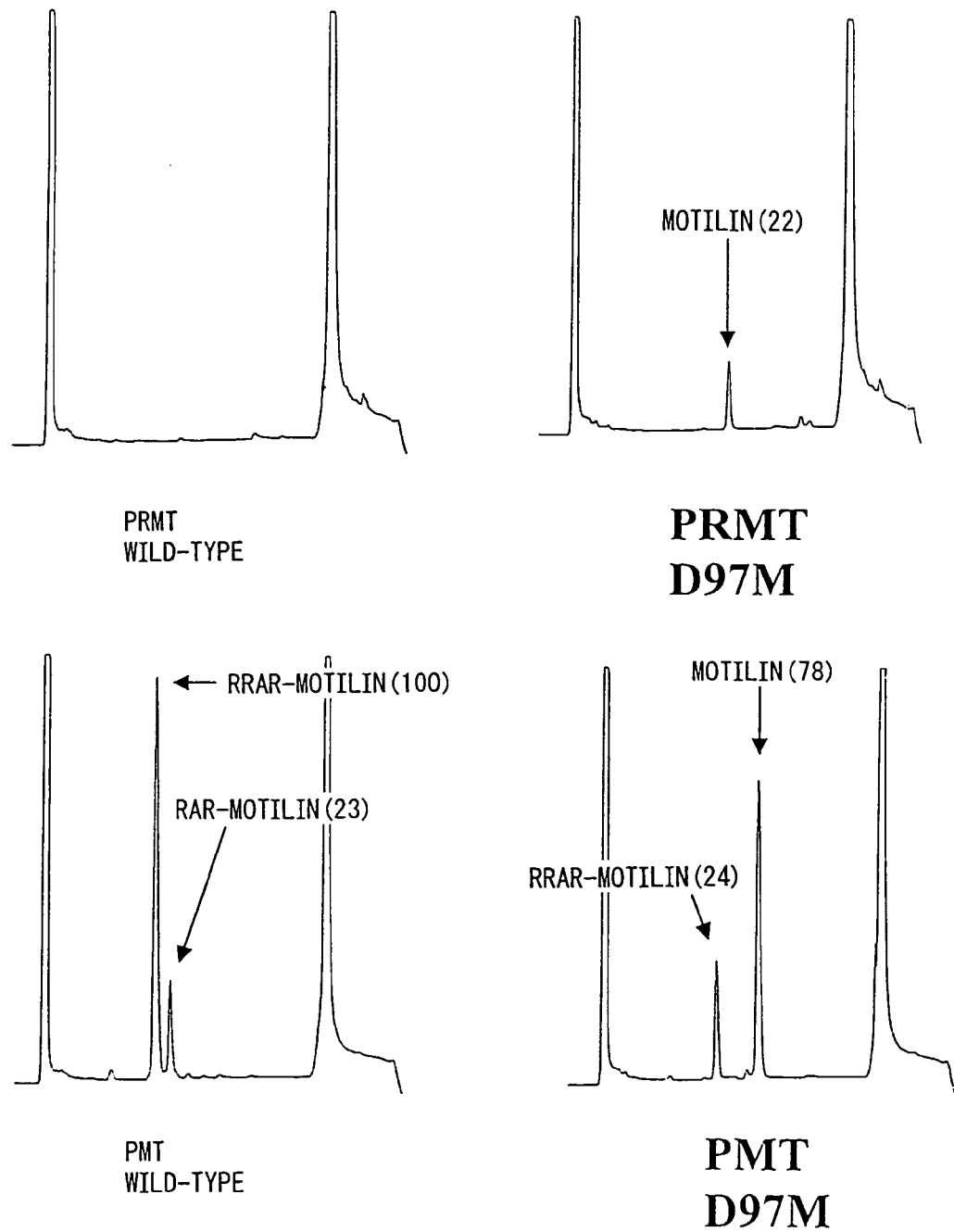
FIG. 6 shows the results of HPLC analysis of reactions 25° C., 120 min) between the fusion proteins PRMT and PMT, and the wild-type OmpT protease and OmpT protease variant D97M. RRAR disclosed as SEQ ID NO: 13.

As a result, it was possible to obtain several variants with relatively high cleavage efficiencies and with different specificities than the wild-type OmpT protease. The highest specificity was exhibited by D97D (wild-type) for fusion The reaction was terminated by addition of 150 µL of 6% acetic acid, 2 M urea to the reaction solution, and upon centrifugation at 10,000×g for 3 minutes, 50 µl of the supernatant was supplied to a YMC PROTEIN RP column. HPLC was carried out at a column temperature of 40° C. and a flow rate of 1 mL/min. Elution was performed with a linear gradient of 20-27.5% acetonitrile containing 0.1% trifluoroacetic acid for 15 minutes, and absorption at 214 nm was monitored. The cleavage site was identified by isolation of the polypeptide fragments and mass analysis. FIG. 6 shows the results of HPLC analysis of cleavage of the human motilin fusion proteins PRMT and PMT by the OmpT protease D97D wild-type as the control and the D97M variant. The cleavage sites and cleavage efficiencies are shown in Table 2.

TABLE 2

Release of motilin from fusion protein PMT by OmpT protease variant OmpT D97M
(RRAR disclosed as SEQ ID NO: 13)

| | D97M | | | D97D (wild-type) | | |
|---|---|---|---|---|---|---|
| Fusion protein | Motilin* | RAR-motilin** | RRAR-motilin*** | Motilin* | RAR-motilin** | RRAR-motilin*** |
| PRMT | 22 | — | — | ND | — | — |
| PMT | 78 | ND | 24 | ND | 23 | 100 |

ND = Not detected.
"—" = Not detectable due to structure of fusion protein.
*Release by cleavage at Arg[140]-Phe[141] from PRMT, Arg[143]-Phe[144] from PMT
**Polypeptide comprising Arg-Ala-Arg-motilin released by cleavage at Arg[140]-Arg[141] from PMT
***Polypeptide comprising Arg-Arg-Ala-Arg-motilin released by cleavage at Arg[139]-Arg[140] from PMT The cleavage efficiencies are expressed as relative cleavage efficiencies to 100 as the cleavage efficiency at Arg[139]-Arg[140] in the case of cleavage of PMT by wild-type D97D. PRMT was not cleaved by D97D wild-type, while cleavage of PMT was primarily cleavage at Arg[139]-Arg[140] and Arg[140]-Arg[141]. When the D97M variant was used, however, PRMT was cleaved and motilin was released. PMT was also cleaved to free motilin, but cleavage was also confirmed at Arg[139]-Arg[140]. However, the amount of motilin released from PMT was 3.5 times higher than from PRMT. This result indicated that the D97M variant is necessary to cut off motilin, and that the motilin cleavage efficiency varies depending on the sequence adjacent to the cleavage site.

Example 15

Polypeptide Production Example Using OmpT Protease Variant and Motilin as the Model Peptide As a polypeptide production example using an OmpT protease variant, W3110 M25 motilin fusion protein PMT-producing cells (see Example 9) and OmpT protease variant OmpT D97M-expressing cells (created by transforming W3110 M25 with pOmpTD97M) were each cultured at high density on a 2 L scale, and the W3110 M25/OmpT D97M-expressing cells were used to release motilin from PMT, and then purified to produce motilin. This was accomplished by the following 3 steps.

Quantitation of motilin was accomplished by analyzing the reaction mixture diluted with 6% acetic acid, 2 M urea under the same conditions as the HPLC analysis described in Example 14, using human motilin purchased from Peptide Research Laboratory as the standard sample. The motilin purity was analyzed by HPLC under the same conditions as for quantitation, except that elution was performed with a linear gradient of 0-50% acetonitrile containing 0.1% trifluoroacetic acid for 50 minutes.

(1) 2 L Scale High-Density Culturing of W3110 M25 Motilin Fusion Protein PMT-Producing Strain and OmpT Protease Variant OmpT D97M-Expressing Strain High-density culturing of W3110 M25 motilin fusion protein PMT-producing cells and OmpT protease variant OmpT D97M-expressing cells was carried out in the following manner, and inclusion bodies and expressing cells were prepared from each. The PMT-producing cells and OmpT D97M-expressing cells were subjected to gyratory culturing overnight in a 500 mL Erlenmeyer flask at 37° C., using 100 mL of LB broth containing 10 mg/L tetracycline. On the following day, it was transferred to a spinner culture vessel containing 2 L of medium comprising 4 g/L $K_2HPO_4$, 4 g/L $KH_2PO_4$, 2.7 g/L $Na_2HPO_4$, 0.2 g/L $NH_4Cl$, 1.2 g/L $(NH_4)_2SO_4$, 4 g/L yeast extract, 2 g/L $MgSO_4.7H_2O$, 40 mg/L $CaCl_2.2H_2O$, 40 mg/L $FeSO_4.7H_2O$, 10 mg/L $MnSO_4.nH_2O$, 10 mg/L $AlCl_3.6H_2O$, 4 mg/L $CoCl_2.6H_2O$, 2 mg/L $ZnSO_4.7H_2O$, 2 mg/L $Na_2MoO_4.2H_2O$, 1 mg/L $CuCl_2.2H_2O$, 0.5 mg/L $H_3BO_4$, 15 g/L glucose and 10 mg/L tetracycline, and culturing was initiated at 32° C.

Figure 7:
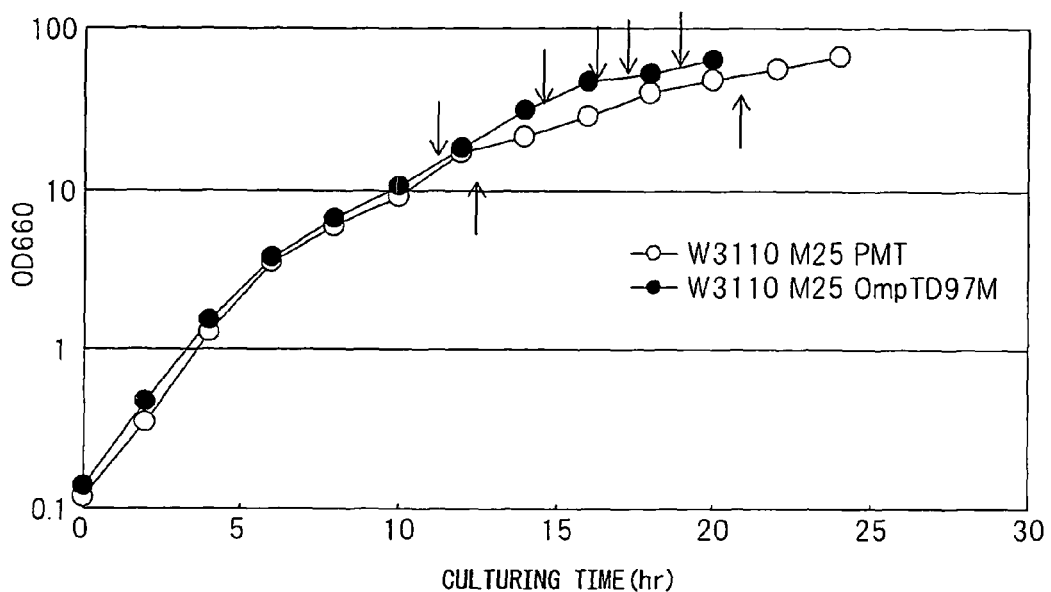
FIG. 7 is a graph showing time-dependent change in the culture solution OD$_{660}$ of 2 L high-density cultures of W3110 M25 PMT and W3110 M25 OmpT D97M-expressing bacteria. The symbol "open circles" represents W3110 M25 MPT, and the symbol "filled circles" represents W3110 M25 OmpT D97M. Culturing was initiated in 1.5% glucose at 32° C. with recombinant E. coli, glycerol was added to 2% upon depletion of the glucose at about 12 hours after the start of culturing, the culturing temperature was adjusted to 37° C., and addition of glycerol was continued to maintain a 2% concentration with each depletion of glycerol (W3110 M25 PMT, ↑; W3110 M25 OmpT D97M, ↓). Culturing of W3110 M25 PMT was terminated after 24 hours, and culturing of W3110 M25 OmpT D97M was terminated after 20 hours.

After glucose depletion, glycerol was added to 2% and the culturing temperature was increased to 37° C. Culturing was thereafter continued while subsequently adding glycerol to 2% as it was depleted. The course of culturing is shown in FIG. 7. The PMT-producing strain completed culturing at 24 hours after starting, and the culture volume was 1700 mL. After disrupting the cells with a Manton-Gaulin cell disruptor, centrifugation was performed at 4° C., 6000×g for 10 minutes to obtain a precipitate. The precipitate was suspended in 2000 mL of deionized water and centrifuged at 4° C., 6000×g for 10 minutes, and the precipitate was recovered. The obtained precipitate was suspended in 2000 mL of 50 mM Tris-HCl (pH 8.0), 5 mM EDTA, 1% Triton-X, and the precipitate from centrifugation at 4° C., 6000×g for 10 minutes was recovered.

The precipitate was suspended in 2000 mL of deionized water and centrifuged at 4° C., 6000×g for 10 minutes, and the precipitate was recovered. The same procedure was repeated to obtain 26 g of precipitate. This was suspended in 26 mL of deionized water and stored at −20° C. until use as an inclusion body suspension ($OD_{660}$-250, 45 mL). The OmpT protease variant W3110 M25/OmpT D97M-expressing cells completed culturing at 20 hours after starting, and the culture volume was 2100 mL. The culture was centrifuged at 4° C., 6000×g for 10 minutes to obtain a precipitate. The precipitate was suspended in 2000 mL of TE (10 mM Tris-HCl (pH 8.0), 1 mM EDTA) and centrifuged at 4° C., 6000×g for 10 minutes, and the precipitate was recovered. This same procedure was repeated and 311 g of precipitate was recovered. The precipitate was suspended in deionized water and stored at −20° C. until use as a cell suspension ($OD_{660}$=320, 390 mL).

(2) Cleavage of Inclusion Body Fusion Protein PMT by OmpT Protease Variant W3110 M25/OmpT D97M-Expressing Cells After adding 1 mL of 1 M sodium phosphate (pH 7.0) and 0.8 mL of 50 mM EDTA to 8 mL of 10 M urea, 4 mL of fusion protein inclusion bodies PMT ($OD_{660}$=250) were added for lysis of the inclusion bodies. Next, 5.2 mL of water was added thereto, 1 mL of the OmpT protease variant W3110 M25/OmpT D97M-expressing cell suspension ($OD_{660}$=320) prepared in (1) above was further added, and reaction was initiated at a reaction mixture volume of 20 mL. The reaction was carried out by shaking for 60 minutes at 25° C., 120 min$^{-1}$. After 60 minutes, 40.5 mL of 20 mM acetic acid (pH 4.0) was added to 13.5 mL of reaction mixture (corresponding to inclusion bodies in 100 mL portion of W3110 M25 motilin fusion protein PMT-producing cell culture), and centrifugation was performed at 4° C., 25,000×g for 10 minutes to obtain a supernatant. This procedure eliminated virtually all of the unreacted fusion protein, protecting peptide and E. coli-derived proteins.

Figure 8:
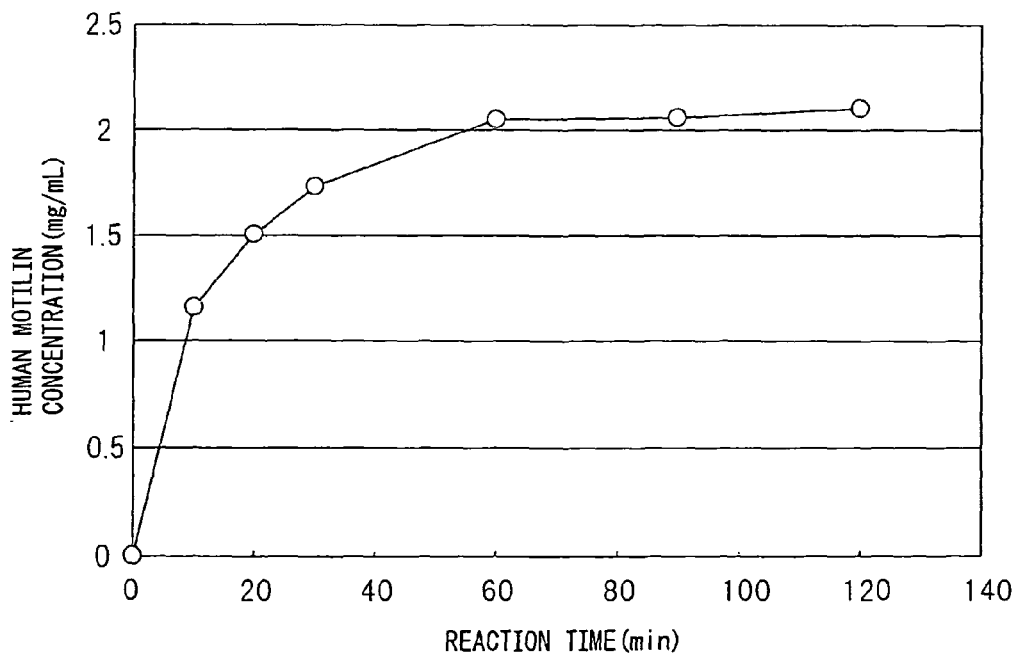
FIG. 8 is a graph showing the time-dependent change in motilin release from the fusion protein PMT by the OmpT protease variant OmpT D97M.
Figure 9:
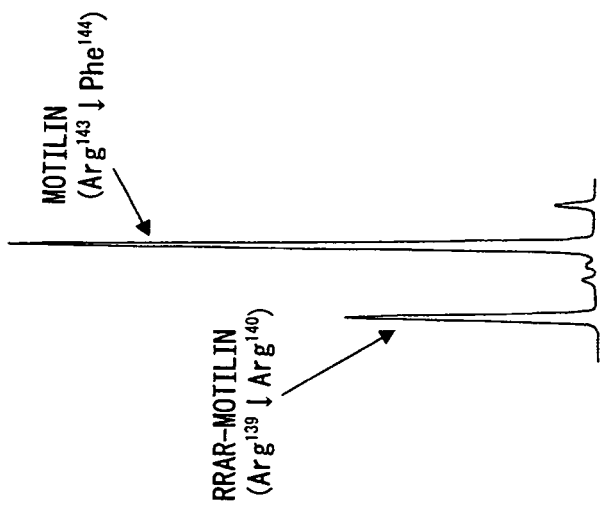
FIG. 9 shows the results of analysis of the reaction solution after 60 minutes by (A) HPLC and (B) SDS-PAGE. Lanes 1: PMT alone; 2: PMT+D97M; 3: motilin sample. Reaction solution composition: 4 M urea, 50 mM sodium phosphate (pH 7.0), 2 mM EDTA, PMT OD$_{660}$=50, OmpT D97M OD$_{660}$=16; Reaction temperature: 25° C.; shaking at 120 min$^{-1}$. RRAR disclosed as SEQ ID NO: 13.

Next, 20 mM acetic acid (pH 4.0) was added to the supernatant to a volume of 200 mL, and the mixture was supplied for the following purification. There was then added 20 mM acetic acid (pH 4.0) to the supernatant to lower the pH, in order to allow adsorption in the cation-exchange chromatography described below. FIG. 8 shows the results of observing the time-dependent change in motilin release up to 120 minutes under the same conditions, to determine the reaction time for release of motilin. The results of HPLC and SDS-PAGE analysis of fusion protein cleavage at 60 minutes after start of the reaction are shown in FIGS. 9A and B. As demonstrated by SDS-PAGE, by 60 minutes after start of the reaction the fusion protein PMT had been almost completely cleaved, hence essentially halting increase in motilin release. The reaction time was therefore established as 60 minutes.

There was detected not only human motilin produced by cleavage at Arg$^{143}$-Pbe$^{144}$, but also a polypeptide (RRAR-motilin) (SEQ ID NO: 13) produced by cleavage at Arg$^{139}$-Arg$^{140}$. In SDS-PAGE, RRAR-motilin (SEQ ID NO: 13) was seen with a more concentrated band than human motilin (FIG. 9B), but the HPLC analysis results contradicted this, indicating a greater area for the peak of human motilin than RRAR-motilin (SEQ ID NO: 13), and thus a larger amount (FIG. 9A). This was assumed to be because RRAR-motilin (SEQ ID NO: 13) is more easily dyeable than human motilin in SDS-PAGE. Thus, it is believed that the band densities are correct as the results of SDS-PAGE and do not reflect the volume ratios.

(3) Purification of Motilin

A 200 mL portion of the supernatant was applied to SP-Sepharose Fast Flow (27 mL, φ26 mm×50 mm) by Amersham Pharmacia previously equilibrated with 20 mM acetic acid (pH 4.0). Next, washing was performed by flowing through 20 mM acetic acid (pH 4.0), 20 mM acetic acid (pH 4.0) and 0.1 M NaCl, at 100 mL each. The elution was performed by flowing through 200 mL of 20 mM acetic acid (pH 4.0) at a linear gradient of 0.1-0.5 M NaCl. The flow rate for cation-exchange chromatography was 5 mL/min in all cases. The elution fractions were dispensed in 5 mL portions and based on HPLC analysis results, fractions were selected and pooled. It was thereby possible to remove the polypeptide produced by cleavage of the fusion protein PMT at Arg$^{139}$-Arg$^{140}$.

The pools were supplied to Vydac 214TPB1520 (24 mL, φ10 mm×300 mm) which had been previously equilibrated with 0.1% trifluoroacetic acid (TFA). Washing was performed by flowing through 100 mL of 0.1% TFA, and elution was carried out by flowing through 200 mL of 0.1% TFA, with a 0-30% acetonitrile linear gradient. The flow rate for reverse-phase chromatography was 1.6 mL/min in all cases. The eluted fractions were dispensed into 4 mL portions and based on HPLC analysis results, fractions were selected and pooled. The results of the purification are shown in Table 3.

TABLE 3

Human motilin purification results

| Purification stage | Volume (mL) | Human motilin (mg/mL) | Human motilin (mg) | Yield (%) | Purity (%) |
|---|---|---|---|---|---|
| Reaction | 13.5 | 2.32 | 31 | 100 | 5.87 |
| Acidic precipitate | 200 | 0.159 | 32 | 100 | 48.8 |
| Cation-exchange | 40.0 | 0.591 | 24 | 77 | 94.2 |
| Reverse-phase | 22.5 | 0.696 | 16 | 52 | >99.0 |

Purification using inclusion bodies corresponding to 0.1 L W3110 M25 PMT culture solution The results of HPLC analysis, mass analysis and N-terminal amino acid analysis of the sample obtained by this purification matched those for human motilin. The purification demonstrated that it is possible to obtain 160 mg of human motilin at ≥99.0% purity at a yield of 52%, per 1 L of W3110 M25 motilin fusion protein PMT-producing cell culture.

Example 16

Figure 11:
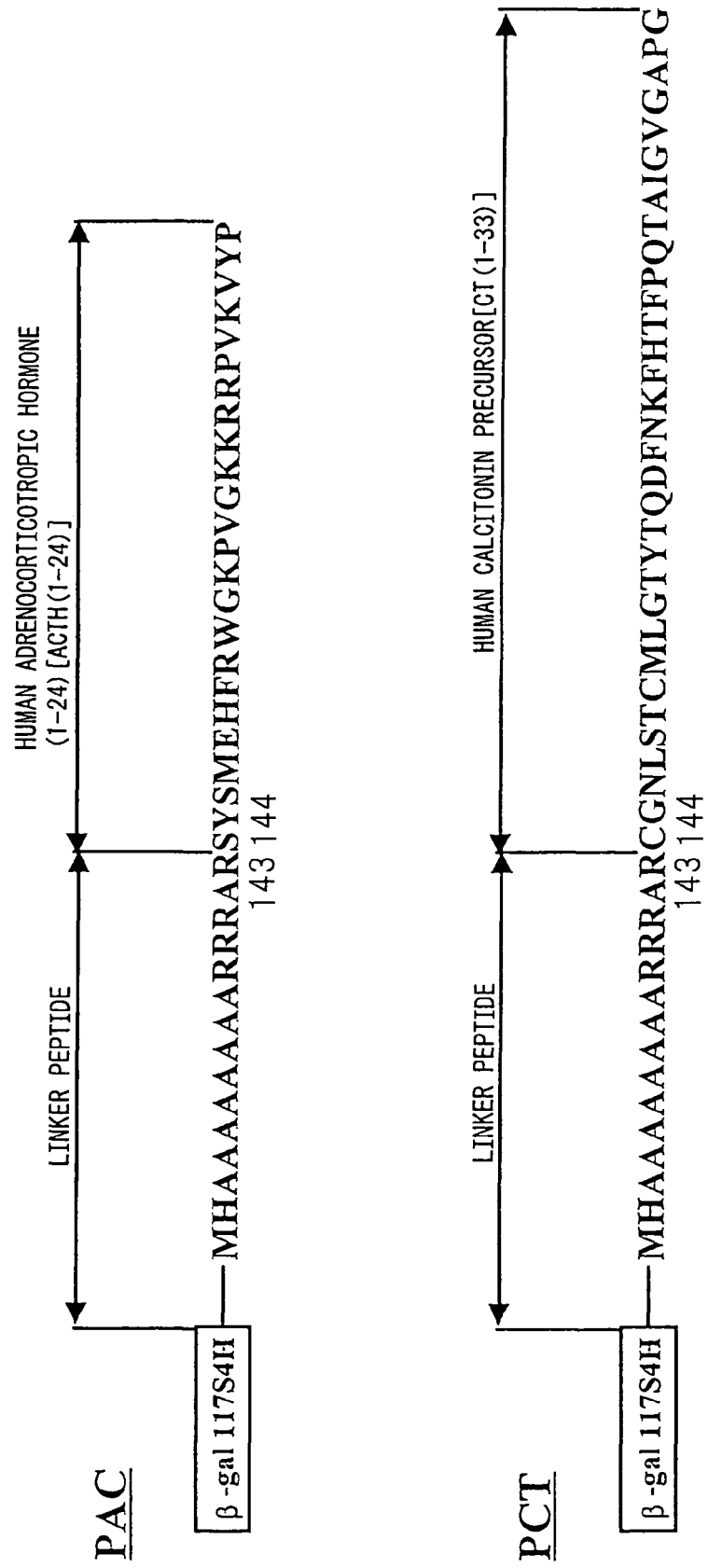
FIG. 11 shows the structures of the fusion proteins PAC (Residues 129-167 of SEQ ID NO: 7) and PCT (Residues 129-176 of SEQ ID NO: 8). The numbers below the amino acids of each fusion protein represent the amino acid sequence numbers from the N-terminus. β-gal117S4H represents the protecting protein deriving from 117 amino acids from the N-terminus of E. coli β-galactosidase, and the linker peptide is the portion from amino acid sequence No. 128 (glutamine) to No. 143 (arginine). The amino acid sequence up to the arginine at position 143 of the fusion protein PMT matches the amino acid sequence up to arginine at position 143 from the N-terminus of the fusion protein PA23' (FIG. 4).
Figure 12:
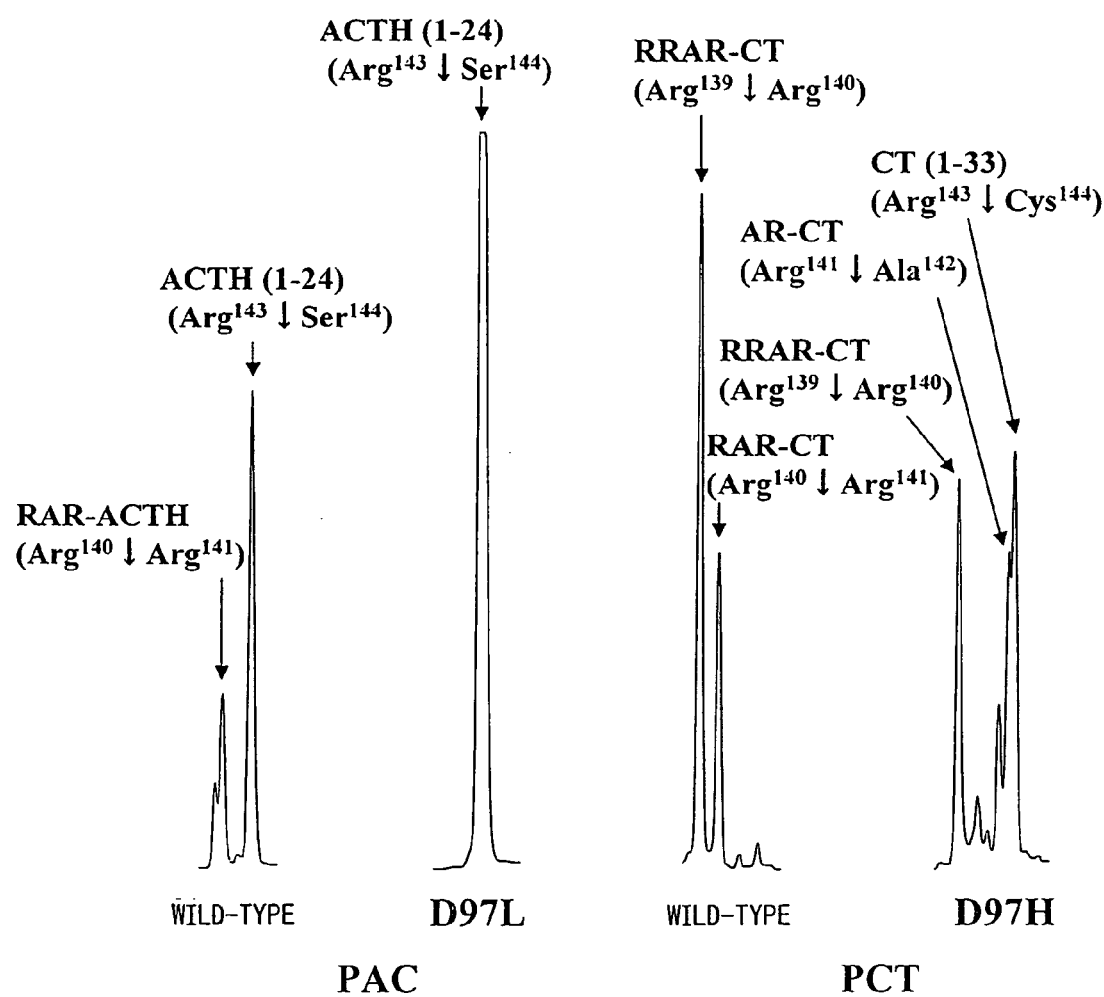
FIG. 12 shows the results of HPLC analysis for reaction between fusion peptides and wild-type OmpT protease and OmpT protease variants. Reaction was performed at 25° C. between PAC and D97L for 10 minutes, and between PCT and D97H for 2 hours. RRAR disclosed as SEQ ID NO: 13.

Physiologically Active Polypeptide Release from Fusion Protein Using OmpT Protease Variant In order to examine whether or not a physiologically active polypeptide other than human motilin can be released from a fusion protein using an OmpT protease variant, a plasmid was constructed to have the structure shown in FIG. 10A, expressing the human adrenocorticotropic hormone(1-24) fusion protein PAC and the human calcitonin precursor fusion protein PCT shown in FIG. 11, and each fusion protein was prepared as inclusion bodies from transformants having each transferred into W3110 M25. They were reacted with OmpT protease variant D97L- or D97H-expressing E. coli W3110 M25 outer membrane for 10 minutes or 2 hours at 25° C. As a control, reaction was carried out for both fusion proteins using wild-type OmpT protease. The HPLC analysis results are shown in FIG. 12.

Cleavage fragments of each fusion protein were isolated by HPLC and subjected to mass analysis. The HPLC was carried out using a YMC PROTEIN RP column at a column temperature of 40° C. and a flow rate of 1 mL/min. Elution was performed with a linear gradient of 10-50% acetonitrile containing 0.1% trifluoroacetic acid for 50 minutes, and absorption at 214 nm was monitored. The fusion protein PAC was cleaved at Arg$^{143}$-Ser$^{144}$ by wild-type OmpT protease to release human adrenocorticotropic hormone(1-24). It was also cleaved at Arg$^{140}$-Arg$^{141}$ to release RAR-ACTH. Though not shown in FIG. 12, there were also produced ACTH(1-15) and ACTH(16-24) by cleavage of Arg$^{143}$-Ser$^{144}$ and Lys$^{158}$-Lys$^{159}$. PAC was further cleaved at Arg$^{143}$-Ser$^{144}$ by D97L, which released human adrenocorticotropic hormone(1-24) at 2.9 times compared to wild-type OmpT protease.

No by-products were released by cleavage at other sites. The fusion protein PCT was cleaved at Arg$^{139}$-Arg$^{140}$ and Arg$^{140}$-Arg$^{141}$ by wild-type OmpT protease, releasing RRAR-CT (SEQ ID NO: 13) and RAR-CT. PCT was cleaved at Arg$^{139}$-Arg$^{140}$, Arg$^{141}$-Ala$^{142}$ and Arg$^{143}$-Cys$^{144}$ by D97H, releasing RRAR-CT (SEQ ID NO: 13), AR-CT and human calcitonin precursor. Release of the target physiologically active polypeptide by wild-type OmpT protease was confirmed from all of the fusion proteins. This demonstrated that physiologically active polypeptide production systems utilizing linker polypeptide sequences and OmpT protease variants indicated in the examples can be applied not only for specific physiologically active polypeptides, and therefore the general utility of this method is thought to be considerable.

Example 17

Co-Expression of Fusion Protein PMT and OmpT Protease Variant D97M

When a fusion protein is expressed as inclusion bodies in *E. coli* and the host *E. coli* cells express OmpT protease, cleavage by OmpT protease occurs simply by dissolving the obtained inclusion bodies in urea. It was therefore investigated whether human motilin can be released by inclusion body lysis when the fusion protein PMT-expressing plasmid pG117S4HompPMT (see Example 9) and a OmpT protease variant D97M-expressing plasmid are co-expressed using OmpT protease-deficient *E. coli* W3110 M25 as the host cells. The OmpT protease variant D97M-expressing plasmid pOmpTD97M is incompatible because it has the same replication origin as pG117S4HompPMT.

An OmpT protease variant D97M-expressing plasmid from pMW218 (FIG. 13) was constructed in the following manner to allow co-expression. With plasmid pOmpTD97M (see Example 11) as the template, the region from the lactose promoter to the trpA terminator of pOmpTD97M was amplified by PCR using primers which included XhoI and HindIII restriction endonuclease sites. After digesting the obtained DNA fragment with XhoI and HindIII, a DNA fragment obtained by digestion of pMW218 with SalI and HindIII was inserted to construct a pMW218-derived OmpT protease variant D97M-expressing plasmid. W3110 M25 motilin fusion protein PMT-producing cells (see Example 9) were transformed with the pMW218-derived OmpT protease variant D97M-expressing plasmid shown in FIG. 13.

The W3110 M25 recombinant *E. coli* was subjected to gyratory culturing at 37° C. overnight in a 2 L Erlenmeyer flask using 400 mL of LB broth containing 10 mg/L tetracycline and 20 mg/L kanamycin. The inclusion bodies were prepared according to ordinary protocol, except that all washing was performed with deionized water. The reaction for release of human motilin from the obtained inclusion bodies was carried out in the following manner. After adding 20 µL of 1 M sodium phosphate (pH 7.0) and 16 µL of 50 mM EDTA to 160 µL of 10 M urea, 80 µL of fusion protein inclusion bodies ($OD_{660}$=100) was added for lysis of the inclusion bodies. Water (124 µL) was then added to start the reaction.

Figure 14:
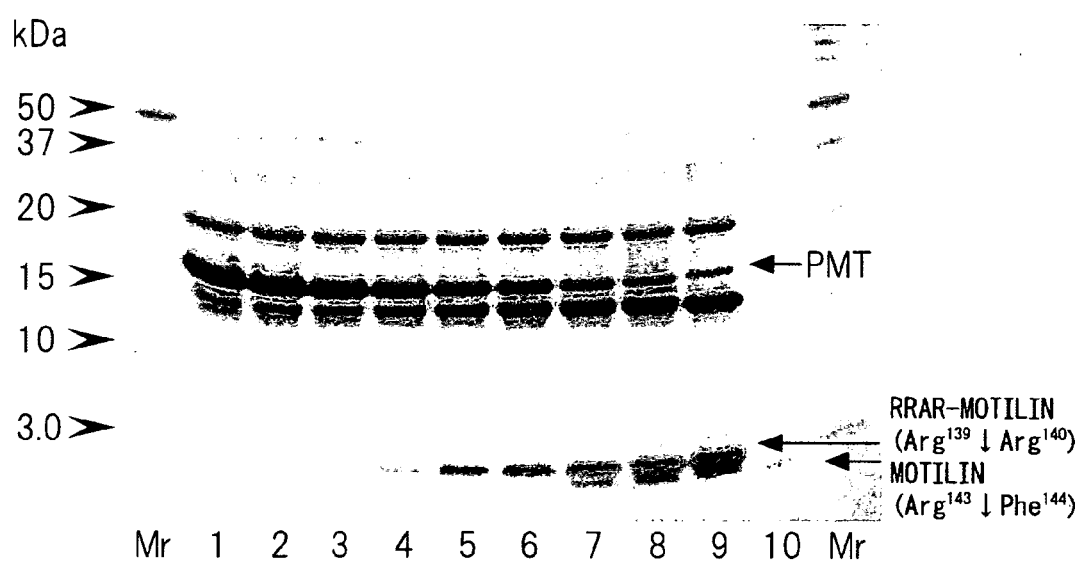
FIG. 14 shows the SDS-PAGE analysis results indicating release of human motilin from the fusion protein PMT using inclusion bodies obtained from W3110 M25-transformed *E. coli* co-expressing the fusion protein PMT and the OmpT protease variant D97M, prepared for Example 17. Mr=protein molecular weight markers; Lanes 1: 20 minutes, 2: 40 minutes, 3: 60 minutes, 4: 120 minutes, 5: 180 minutes, 6: 240 minutes, 7: 300 minutes, 8: 360 minutes, 9: 1440 minutes (24 hrs) after start of reaction, 10: motilin sample. Reaction mixture composition: 4 M urea, 50 mM sodium phosphate (pH 7.0), 2 mM EDTA, inclusion body $OD_{660}$=20, Reaction temperature: 25° C. RRAR disclosed as SEQ ID NO: 13.

The reaction was carried out at 25° C., and sampling was performed at 20, 40, 60, 120, 180, 240, 300, 360 and 1440 minutes after start of the reaction for analysis by SDS-PAGE (FIG. 14). The analysis results showed that reaction of 1440 minutes, i.e. 24 hours, caused virtually complete digestion of the fusion protein PMT. This demonstrated that prolonging the reaction time can achieve complete digestion of the fusion protein PMT even by simple lysis of inclusion bodies obtained from co-expressing cells, thereby allowing release of human motilin, although not as rapidly as when using *E. coli* cells transformed with the OmpT protease variant D97M-expressing plasmid pOmpTD97M as in Example 15.

Example 18

Reaction Between Fusion Proteins PMT, PMT6D and PMT7D, and OmpT Protease Variant D97M While the results of Example 14 demonstrated that motilin is produced from the fusion protein PMT by the OmpT protease variant D97M, cleavage also occurred at $Arg^{139}$-$Arg^{140}$ to yield the by-product RRAR-motilin (SEQ ID NO: 13). On the other hand, the results of Example 8 indicated that situating the acidic amino acid aspartic acid at position P3 or P4 where cleavage is not desired can inhibit cleavage at those sites.

Thus, since $Arg^{139}$-$Arg^{140}$ of the motilin fusion protein PMT is a site where cleavage is not desired, plasmids were constructed having the structures shown in FIG. 10A, expressing the motilin fusion proteins PMT6D and PMT7D shown in FIG. 15, and these were used to transform W3110 M25 *E. coli*. The fusion proteins were recovered as inclusion bodies, and the inclusion bodies were used for reaction for 2 hours at 25° C., with motilin fusion protein at a concentration of 4 mg/mL ($OD_{660}$=approximately 20), 4 M urea, 2 mM EDTA, 50 mM sodium phosphate and 0.52 mg/mL of OmpT protease variant D97M ($OD_{660}$=1). The inclusion body protein concentration was measured by HPLC in the following manner. The inclusion bodies were added at $OD_{660}$=1 to 6% acetic acid, 2 M urea, the mixture was centrifuged at 10,000×g for 3 minutes and 50 µL of the supernatant was supplied to a YMC PROTEIN RP column. The HPLC was carried out with a column temperature of 40° C. and a flow rate of 1 mL/min.

Figure 16:
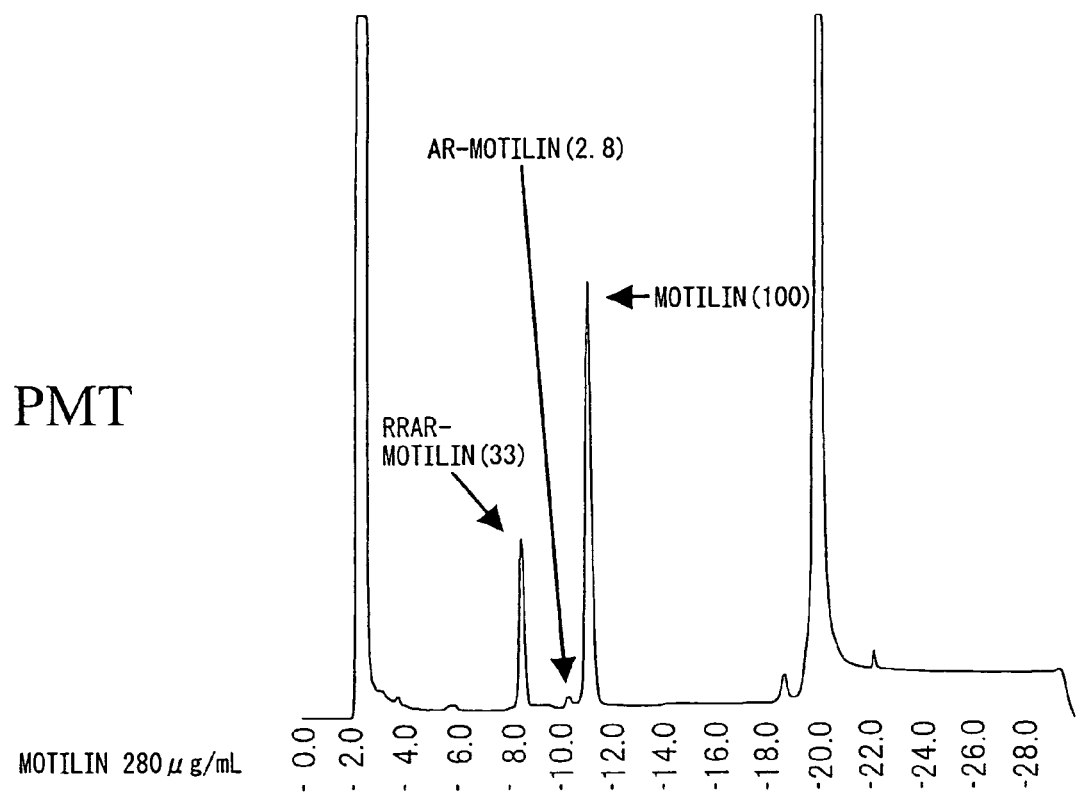
FIG. 16 shows the results of HPLC analysis for reaction (25° C., 120 min) between the fusion protein PMT and the OmpT protease variant D97M. The numbers in parentheses indicate each by-product concentration, where the concentration of motilin produced from the fusion protein is 100. RRAR disclosed as SEC, ID NO: 13.
Figure 17:
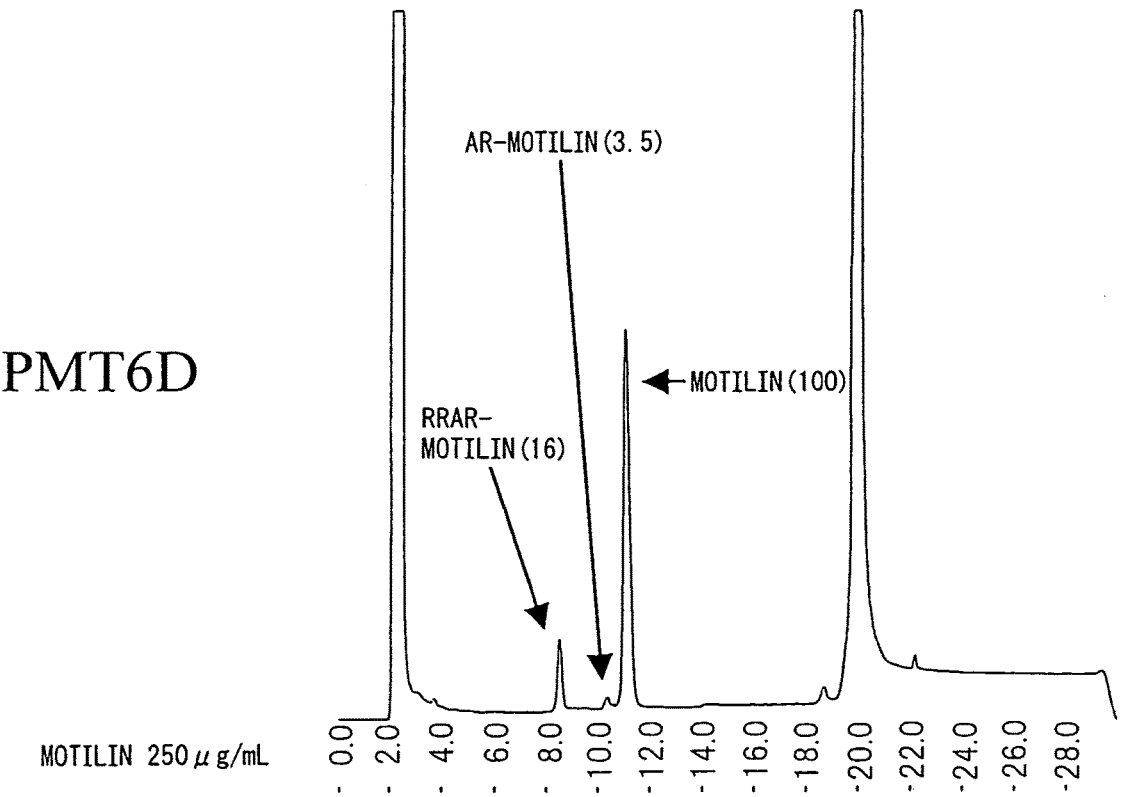
FIG. 17 shows the results of HPLC analysis for reaction (25° C., 120 min) between the fusion protein PMT6D and the OmpT protease variant D97M. The numbers in parentheses indicate each by-product concentration, where the concentration of motilin produced from the fusion protein is 100. RRAR disclosed as SEQ ID NO: 13.
Figure 18:
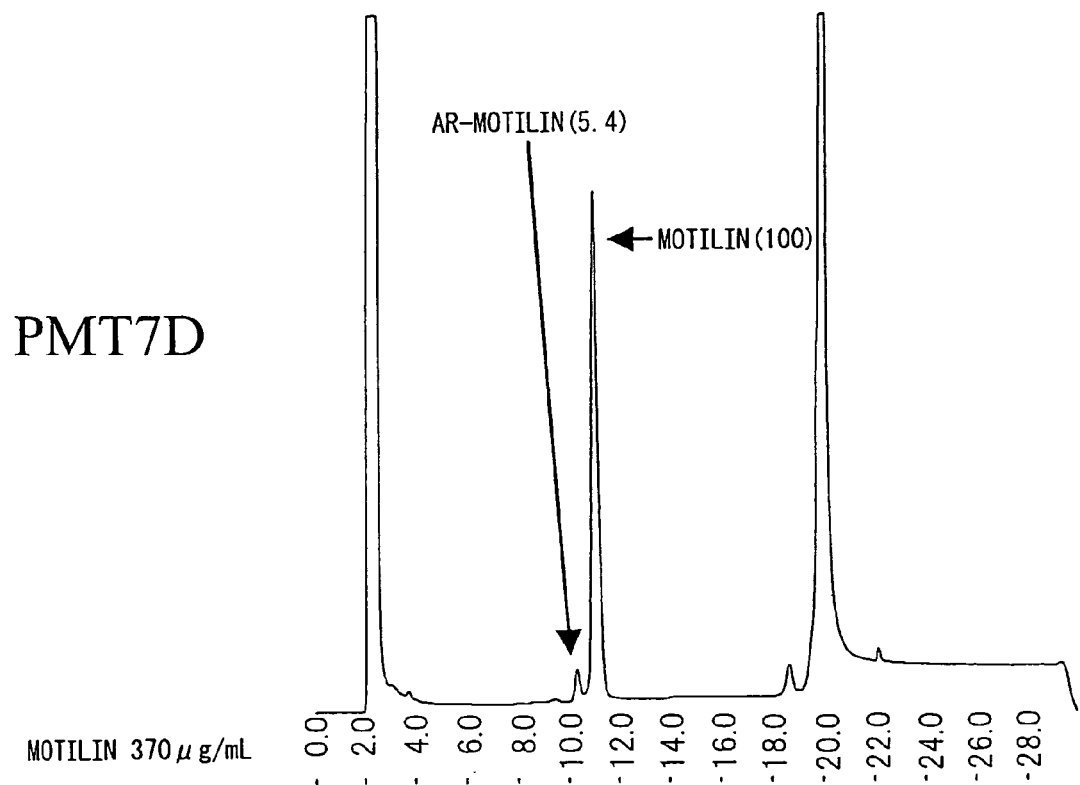
FIG. 18 shows the results of HPLC analysis for reaction (25° C., 120 min) between the fusion protein PMT7D and the OmpT protease variant D97M. The numbers in parentheses indicate each by-product concentration, where the concentration of motilin produced from the fusion protein is 100.

Elution was performed for 40 minutes with a linear gradient of 20-60% acetonitrile containing 0.1% trifluoroacetic acid, and absorption at 220 nm was monitored. The inclusion body protein concentration was detected using bovine serum albumin (BSA) as the standard sample. The OmpT protease variant D97M suspension ($OD_{660}$=0.5) in the *E. coli* outer membrane fraction was supplied to SDS-PAGE, and the variant concentration was measured with a densitometer using purified OmpT as the standard sample. The results of HPLC analysis of each of the reaction solutions are shown in FIGS. 16, 17 and 18. Motilin was released at 280, 250 and 370 µg/mL from the motilin fusion proteins PMT, PMT6D and PMT7D, respectively.

FIGS. 16-18 also show the concentrations of the by-products AR-motilin (produced by cleavage at $Arg^{141}$-$Ala^{142}$) and RRAR-motilin) (SEQ ID NO: 13) produced by cleavage at $Arg^{139}$-$Arg^{140}$), where the concentration of motilin released from each is defined as 100. By-products were yielded at 2.8 and 33% with PMT (FIGS. 16) and at 3.5 and 16% with PMT6D (FIG. 17), and therefore RRAR-motilin (SEQ ID NO: 13) production was particularly inhibited. Also, no peak for RRAR-motilin (SEQ ID NO: 13) was detected with PMT7D (FIG. 18). This matches with the results of Example 8, demonstrating that even when using OmpT variant enzymes, situating the acidic amino acid aspartic acid at the P3 or P4 position, at which cleavage is not desired, can inhibit cleavage at those sites. Motilin was released in the greatest amount from PMT7D (370µg/mL), but this was ascribed to an increased motilin release concentration permitted by the lack of by-product.

The basic full amino acid sequences of each of the fusion proteins according to the invention are listed below.

Fusion Protein PRR (SEQ ID NO: 1; FIG. 1; Examples 1-2, 13)

| Sequence for PRR |
|---|
| Met Thr Met Ile Thr Asp Ser Leu Ala Val Val Leu Gln Arg Lys  15 |
| Asp Trp Glu Asn Pro Gly Val Thr Gln Leu Asn Arg Leu Ala Ala  30 |
| His Pro Pro Phe Ala Ser Trp Arg Asn Ser Asp Asp Ala Arg Thr  45 |
| Asp Arg Pro Ser Gln Gln Leu Arg Ser Leu Asn Gly Glu Trp Arg  60 |
| Phe Ala Trp Phe Pro Ala Pro Glu Ala Val Pro Glu Ser Leu Leu  75 |
| Asp Leu Pro Glu Ala Asp Thr Val Val Val Pro Asp Ser Ser Asn  90 |
| Trp Gln Met His Gly Tyr Asp Ala Pro Ile Tyr Thr Asn Val Thr 105 |
| Tyr Pro Ile Thr Val Asn Pro Pro Phe Val Pro Thr Glu Pro His 120 |
| His His His Pro Gly Gly Arg Gln Met His Gly Tyr Asp Ala Glu 135 |
| Leu Arg Leu Tyr <u>Arg Arg</u> His His Gly Ser Gly Ser Pro Tyr Arg 150 |
| His Pro Arg <u>His Ala Glu Gly Thr Phe Thr Ser Asp Val Ser Ser</u> 165 |
| <u>Tyr Leu Glu Gly Gln Ala Ala Lys Glu Phe Ile Ala Trp Leu Val</u> 180 |
| <u>Lys Gly Arg Gly</u>                                             184 |

In this amino acid sequence, the underlined portion is the amino acid sequence of human glucacon-like peptide-1(7-37) (GLP-1(7-37)), and the double underlined portion is the basic amino acid pair ($Arg^{140}$-$Arg^{141}$) which is the OmpT protease cleavage site. The protecting protein (β-gal117S4H) derived from the 117 N-terminal amino acids of β-galactosidase of *E. coli* consists of the amino acid sequence from methionine at amino acid No. 1 to arginine at amino acid No. 127. The linker peptide consists of the amino acid sequence from glutamine at amino acid No. 128 to arginine at amino acid No. 153.

PA-Derivative Fusion Protein (SEQ. ID No: 2; FIG. 2; Examples 1-2)

| Sequence for PA |
|---|
| Met Thr Met Ile Thr Asp Ser Leu Ala Val Val Leu Gln Arg Lys  15 |
| Asp Trp Glu Asn Pro Gly Val Thr Gln Leu Asn Arg Leu Ala Ala  30 |
| His Pro Pro Phe Ala Ser Trp Arg Asn Ser Asp Asp Ala Arg Thr  45 |
| Asp Arg Pro Ser Gln Gln Leu Arg Ser Leu Asn Gly Glu Trp Arg  60 |
| Phe Ala Trp Phe Pro Ala Pro Glu Ala Val Pro Glu Ser Leu Leu  75 |
| Asp Leu Pro Glu Ala Asp Thr Val Val Val Pro Asp Ser Ser Asn  90 |
| Trp Gln Met His Gly Tyr Asp Ala Pro Ile Tyr Thr Asn Val Thr 105 |
| Tyr Pro Ile Thr Val Asn Pro Pro Phe Val Pro Thr Glu Pro His 120 |
| His His His Pro Gly Gly Arg Gln Met His Ala Ala Ala Ala Ala 135 |
| Ala Ala Ala Ala <u>Arg Arg</u> Ala Ala Ala Ala Gly Ser Pro Tyr Arg 150 |
| His Pro Arg <u>His Ala Glu Gly Thr Phe Thr Ser Asp Val Ser Ser</u> 165 |
| <u>Tyr Leu Glu Gly Gln Ala Ala Lys Glu Phe Ile Ala Trp Leu Val</u> 180 |
| <u>Lys Gly Arg Gly</u>                                             184 |

In this amino acid sequence, the underlined portion is the amino acid sequence of human glucacon-like peptide-1(7-37) (GLP-1(7-37)), and the double underlined portion is the basic amino acid pair ($Arg^{140}$-$Arg^{141}$) which is the OmpT protease cleavage site. The protecting protein (β-gal117S4H) derived from the 117 N-terminal amino acids of β-galactosidase of *E. coli* consists of the amino acid sequence from methionine at amino acid No. 1 to arginine at amino acid No. 127. The linker peptide consists of the amino acid sequence from glutamine at amino acid No. 128 to arginine at amino acid No. 153.

PA3'-Derivative Fusion Protein (SEQ. ID No: 3; FIGS. 2-3; Examples 3-6)

| Sequence for PA3' | | | | | | | | | | | | | | |
|---|---|---|---|---|---|---|---|---|---|---|---|---|---|---|
| Met | Thr | Met | Ile | Thr | Asp | Ser | Leu | Ala | Val | Val | Leu | Gln | Arg | Lys | 15 |
| Asp | Trp | Glu | Asn | Pro | Gly | Val | Thr | Gln | Leu | Asn | Arg | Leu | Ala | Ala | 30 |
| His | Pro | Pro | Phe | Ala | Ser | Trp | Arg | Asn | Ser | Asp | Asp | Ala | Arg | Thr | 45 |
| Asp | Arg | Pro | Ser | Gln | Gln | Leu | Arg | Ser | Leu | Asn | Gly | Glu | Trp | Arg | 60 |
| Phe | Ala | Trp | Phe | Pro | Ala | Pro | Glu | Ala | Val | Pro | Glu | Ser | Leu | Leu | 75 |
| Asp | Leu | Pro | Glu | Ala | Asp | Thr | Val | Val | Val | Pro | Asp | Ser | Ser | Asn | 90 |
| Trp | Gln | Met | His | Gly | Tyr | Asp | Ala | Pro | Ile | Tyr | Thr | Asn | Val | Thr | 105 |
| Tyr | Pro | Ile | Thr | Val | Asn | Pro | Pro | Phe | Val | Pro | Thr | Glu | Pro | His | 120 |
| His | His | His | Pro | Gly | Gly | Arg | Gln | Met | His | Ala | Ala | Ala | Ala | Ala | 135 |
| Ala | Ala | Ala | Ala | <u>Arg Arg</u> | | Ala | <u>Arg Ala</u> | | Ala | Gly | Ser | Pro | Tyr | Arg | 150 |
| His | Pro | Arg | <u>His</u> | <u>Ala</u> | <u>Glu</u> | <u>Gly</u> | <u>Thr</u> | <u>Phe</u> | <u>Thr</u> | <u>Ser</u> | <u>Asp</u> | <u>Val</u> | <u>Ser</u> | <u>Ser</u> | 165 |
| <u>Tyr</u> | <u>Leu</u> | <u>Glu</u> | <u>Gly</u> | <u>Gln</u> | <u>Ala</u> | <u>Ala</u> | <u>Lys</u> | <u>Glu</u> | <u>Phe</u> | <u>Ile</u> | <u>Ala</u> | <u>Trp</u> | <u>Leu</u> | <u>Val</u> | 180 |
| <u>Lys</u> | <u>Gly</u> | <u>Arg</u> | <u>Gly</u> | | | | | | | | | | | | 184 |

In this amino acid sequence, the underlined portion is the amino acid sequence of human glucacon-like peptide-1(7-37) (GLP-1(7-37)), and the double underlined portions are the OmpT protease cleavage sites ($Arg^{140}$-$Arg^{141}$ and $Arg^{143}$-$Ala^{144}$). The protecting protein (β-gal117S4H) derived from the 117 N-terminal amino acids of β-galactosidase of E. coli consists of the amino acid sequence from methionine at amino acid No. 1 to arginine at amino acid No. 127. The linker peptide consists of the amino acid sequence from glutamine at amino acid No. 128 to arginine at amino acid No. 153.

PA23'-Derivative Fusion Protein (SEQ. ID No: 4; FIGS. 3-4; Examples 5-8)

In this amino acid sequence, the underlined portion is the amino acid sequence of human glucacon-like peptide-1(7-37) (GLP-1(7-37)), and the double underlined portions are the OmpT protease cleavage sites ($Arg^{139}$-$Arg^{140}$, $Arg^{140}$-$Arg^{141}$ and $Arg^{143}$-$Ala^{144}$). The protecting protein (β-gal117S4H) derived from the 117 N-terminal amino acids of β-galactosidase of E. coli consists of the amino acid sequence from methionine at amino acid No. 1 to arginine at amino acid No. 127. The linker peptide consists of the amino acid sequence from glutamine at amino acid No. 128 to arginine at amino acid No. 153.

| Sequence for PA23' | | | | | | | | | | | | | | |
|---|---|---|---|---|---|---|---|---|---|---|---|---|---|---|
| Met | Thr | Met | Ile | Thr | Asp | Ser | Leu | Ala | Val | Val | Leu | Gln | Arg | Lys | 15 |
| Asp | Trp | Glu | Asn | Pro | Gly | Val | Thr | Gln | Leu | Asn | Arg | Leu | Ala | Ala | 30 |
| His | Pro | Pro | Phe | Ala | Ser | Trp | Arg | Asn | Ser | Asp | Asp | Ala | Arg | Thr | 45 |
| Asp | Arg | Pro | Ser | Gln | Gln | Leu | Arg | Ser | Leu | Asn | Gly | Glu | Trp | Arg | 60 |
| Phe | Ala | Trp | Phe | Pro | Ala | Pro | Glu | Ala | Val | Pro | Glu | Ser | Leu | Leu | 75 |
| Asp | Leu | Pro | Glu | Ala | Asp | Thr | Val | Val | Val | Pro | Asp | Ser | Ser | Asn | 90 |
| Trp | Gln | Met | His | Gly | Tyr | Asp | Ala | Pro | Ile | Tyr | Thr | Asn | Val | Thr | 105 |
| Tyr | Pro | Ile | Thr | Val | Asn | Pro | Pro | Phe | Val | Pro | Thr | Glu | Pro | His | 120 |
| His | His | His | Pro | Gly | Gly | Arg | Gln | Met | His | Ala | Ala | Ala | Ala | Ala | 135 |
| Ala | Ala | Ala | <u>Arg Arg Arg</u> | | | Ala | <u>Arg Ala</u> | | Ala | Gly | Ser | Pro | Tyr | Arg | 150 |
| His | Pro | Arg | <u>His</u> | <u>Ala</u> | <u>Glu</u> | <u>Gly</u> | <u>Thr</u> | <u>Phe</u> | <u>Thr</u> | <u>Ser</u> | <u>Asp</u> | <u>Val</u> | <u>Ser</u> | <u>Ser</u> | 165 |
| <u>Tyr</u> | <u>Leu</u> | <u>Glu</u> | <u>Gly</u> | <u>Gln</u> | <u>Ala</u> | <u>Ala</u> | <u>Lys</u> | <u>Glu</u> | <u>Phe</u> | <u>Ile</u> | <u>Ala</u> | <u>Trp</u> | <u>Leu</u> | <u>Val</u> | 180 |
| <u>Lys</u> | <u>Gly</u> | <u>Arg</u> | <u>Gly</u> | | | | | | | | | | | | 184 |

Fusion Protein PRMT (SEQ. ID No: 5; FIG. 5; Examples 9-10, 14)

| Sequence for PRMT | |
|---|---|
| Met Thr Met Ile Thr Asp Ser Leu Ala Val Val Leu Gln Arg Lys | 15 |
| Asp Trp Glu Asn Pro Gly Val Thr Gln Leu Asn Arg Leu Ala Ala | 30 |
| His Pro Pro Phe Ala Ser Trp Arg Asn Ser Asp Asp Ala Arg Thr | 45 |
| Asp Arg Pro Ser Gln Gln Leu Arg Ser Leu Asn Gly Glu Trp Arg | 60 |
| Phe Ala Trp Phe Pro Ala Pro Glu Ala Val Pro Glu Ser Leu Leu | 75 |
| Asp Leu Pro Glu Ala Asp Thr Val Val Val Pro Asp Ser Ser Asn | 90 |
| Trp Gln Met His Gly Tyr Asp Ala Pro Ile Tyr Thr Asn Val Thr | 105 |
| Tyr Pro Ile Thr Val Asn Pro Pro Phe Val Pro Thr Glu Pro His | 120 |
| His His His Pro Gly Gly Arg Gln Met His Gly Tyr Asp Ala Glu | 135 |
| Leu Arg Leu Tyr <u>Arg</u> <u>Phe Val Pro Ile Phe Thr Tyr Gly Gly Leu</u> | 150 |
| <u>Gln Arg Met Gln Glu Lys Glu Arg Asn Lys Gly Gln</u> | 162 |

In this amino acid sequence, the underlined portion is the amino acid sequence of human motilin, and the double underlined portion is the arginine (Arg$^{140}$) corresponding to position P1 of the OmpT protease cleavage site of the fusion protein PRR. The protecting protein (β-gal117S4H) derived from the 117 N-terminal amino acids of β-galactosidase of E. coli consists of the amino acid sequence from methionine at amino acid No. 1 to arginine at amino acid No. 127. The linker peptide consists of the amino acid sequence from glutamine at amino acid No. 128 to arginine at amino acid No. 140.

Fusion protein PMT (SEQ. ID No: 6; FIG. 5; Examples 9-10, 14-15, 17-18)

| Sequence for PMT | |
|---|---|
| Met Thr Met Ile Thr Asp Ser Leu Ala Val Val Leu Gln Arg Lys | 15 |
| Asp Trp Glu Asn Pro Gly Val Thr Gln Leu Asn Arg Leu Ala Ala | 30 |
| His Pro Pro Phe Ala Ser Trp Arg Asn Ser Asp Asp Ala Arg Thr | 45 |
| Asp Arg Pro Ser Gln Gln Leu Arg Ser Leu Asn Gly Glu Trp Arg | 60 |
| Phe Ala Trp Phe Pro Ala Pro Glu Ala Val Pro Glu Ser Leu Leu | 75 |
| Asp Leu Pro Glu Ala Asp Thr Val Val Val Pro Asp Ser Ser Asn | 90 |
| Trp Gln Met His Gly Tyr Asp Ala Pro Ile Tyr Thr Asn Val Thr | 105 |
| Tyr Pro Ile Thr Val Asn Pro Pro Phe Val Pro Thr Glu Pro His | 120 |
| His His His Pro Gly Gly Arg Gln Met His Ala Ala Ala Ala Ala | 135 |
| Ala Ala Ala Arg Arg Arg Ala Arg <u>Phe Val Pro Ile Phe Thr Tyr</u> | 150 |
| <u>Gly Glu Leu Gln Arg Met Gln Glu Lys Glu Arg Asn Lys Gly Gln</u> | 165 |

In this amino acid sequence, the underlined portion is the amino acid sequence of human motilin. The protecting protein (β-gal117S4H) derived from the 117 N-terminal amino acids of β-galactosidase of E. coli consists of the amino acid sequence from methionine at amino acid No. 1 to arginine at amino acid No. 127. The linker peptide consists of the amino acid sequence from glutamine at amino acid No. 128 to arginine at amino acid No. 143.

Fusion Protein PAC (SEQ. ID No: 7; FIG. 11; Example 16)

| Sequence for PAC | | | | | | | | | | | | | | |
|---|---|---|---|---|---|---|---|---|---|---|---|---|---|---|
| Met | Thr | Met | Ile | Thr | Asp | Ser | Leu | Ala | Val | Val | Leu | Gln | Arg | Lys | 15 |
| Asp | Trp | Glu | Asn | Pro | Gly | Val | Thr | Gln | Leu | Asn | Arg | Leu | Ala | Ala | 30 |
| His | Pro | Pro | Phe | Ala | Ser | Trp | Arg | Asn | Ser | Asp | Asp | Ala | Arg | Thr | 45 |
| Asp | Arg | Pro | Ser | Gln | Gln | Leu | Arg | Ser | Leu | Asn | Gly | Glu | Trp | Arg | 60 |
| Phe | Ala | Trp | Phe | Pro | Ala | Pro | Glu | Ala | Val | Pro | Glu | Ser | Leu | Leu | 75 |
| Asp | Leu | Pro | Glu | Ala | Asp | Thr | Val | Val | Val | Pro | Asp | Ser | Ser | Asn | 90 |
| Trp | Gln | Met | His | Gly | Tyr | Asp | Ala | Pro | Ile | Tyr | Thr | Asn | Val | Thr | 105 |
| Tyr | Pro | Ile | Thr | Val | Asn | Pro | Pro | Phe | Val | Pro | Thr | Glu | Pro | His | 120 |
| His | His | His | Pro | Gly | Gly | Arg | Gln | Met | His | Ala | Ala | Ala | Ala | Ala | 135 |
| Ala | Ala | Ala | Arg | Arg | Arg | Ala | Arg | <u>Ser</u> | <u>Tyr</u> | <u>Ser</u> | <u>Met</u> | <u>Glu</u> | <u>His</u> | <u>Phe</u> | 150 |
| <u>Arg</u> | <u>Trp</u> | <u>Gly</u> | <u>Lys</u> | <u>Pro</u> | <u>Val</u> | <u>Gly</u> | <u>Lys</u> | <u>Lys</u> | <u>Arg</u> | <u>Arg</u> | <u>Pro</u> | <u>Val</u> | <u>Lys</u> | <u>Val</u> | 165 |
| <u>Tyr</u> | <u>Pro</u> | | | | | | | | | | | | | | 167 |

In this amino acid sequence, the underlined portion is the amino acid sequence of human adrenocorticotropic hormone (1-24). The protecting protein (β-gal117S4H) derived from the 117 N-terminal amino acids of β-galactosidase of *E. coli* consists of the amino acid sequence from methionine at amino acid No. 1 to arginine at amino acid No. 127. The linker peptide consists of the amino acid sequence from glutamine at amino acid No. 128 to arginine at amino acid No. 143.

Fusion Protein PCT (SEQ. ID No: 8; FIG. 11; Example 16)

| Sequence for PCT | | | | | | | | | | | | | | |
|---|---|---|---|---|---|---|---|---|---|---|---|---|---|---|
| Met | Thr | Met | Ile | Thr | Asp | Ser | Leu | Ala | Val | Val | Leu | Gln | Arg | Lys | 15 |
| Asp | Trp | Glu | Asn | Pro | Gly | Val | Thr | Gln | Leu | Asn | Arg | Leu | Ala | Ala | 30 |
| His | Pro | Pro | Phe | Ala | Ser | Trp | Arg | Asn | Ser | Asp | Asp | Ala | Arg | Thr | 45 |
| Asp | Arg | Pro | Ser | Gln | Gln | Leu | Arg | Ser | Leu | Asn | Gly | Glu | Trp | Arg | 60 |
| Phe | Ala | Trp | Phe | Pro | Ala | Pro | Glu | Ala | Val | Pro | Glu | Ser | Leu | Leu | 75 |
| Asp | Leu | Pro | Glu | Ala | Asp | Thr | Val | Val | Val | Pro | Asp | Ser | Ser | Asn | 90 |
| Trp | Gln | Met | His | Gly | Tyr | Asp | Ala | Pro | Ile | Tyr | Thr | Asn | Val | Thr | 105 |
| Tyr | Pro | Ile | Thr | Val | Asn | Pro | Pro | Phe | Val | Pro | Thr | Glu | Pro | His | 120 |
| His | His | His | Pro | Gly | Gly | Arg | Gln | Met | His | Ala | Ala | Ala | Ala | Ala | 135 |
| Ala | Ala | Ala | Arg | Arg | Arg | Ala | Arg | <u>Cys</u> | <u>Gly</u> | <u>Asn</u> | <u>Leu</u> | <u>Ser</u> | <u>Thr</u> | <u>Cys</u> | 150 |
| <u>Met</u> | <u>Leu</u> | <u>Gly</u> | <u>Thr</u> | <u>Tyr</u> | <u>Thr</u> | <u>Gln</u> | <u>Asp</u> | <u>Phe</u> | <u>Asn</u> | <u>Lys</u> | <u>Phe</u> | <u>His</u> | <u>Thr</u> | <u>Phe</u> | 165 |
| <u>Pro</u> | <u>Gln</u> | <u>Thr</u> | <u>Ala</u> | <u>Ile</u> | <u>Gly</u> | <u>Val</u> | <u>Gly</u> | <u>Ala</u> | <u>Pro</u> | <u>Gly</u> | | | | | 176 |

In this amino acid sequence, the underlined portion is the amino acid sequence of human calcitonin precursor. The protecting protein (β-gal117S4H) derived from the 117 N-terminal amino acids of β-galactosidase of *E. coli* consists of the amino acid sequence from methionine at amino acid No. 1 to arginine at amino acid No. 127. The linker peptide consists of the amino acid sequence from glutamine at amino acid No. 128 to arginine at amino acid No. 143.

What is claimed is:

1. A process for cleaving a polypeptide comprising cleaving the polypeptide with an *E. coli* OmpT protease variant consisting of an amino acid substitution at the 97th position of the amino acid sequence of SEQ ID NO: 41,
   wherein the 97th amino acid from the N-terminus of the *E. coli* OmpT protease variant is leucine, methionine, or histidine,
   wherein the polypeptide comprises a cleavage site that is a peptide bond between the P1 position and the P1' position, and
   wherein the P1 position is arginine or lysine and the P1' position is:
   (1) serine or alanine when the 97th amino acid from the N-terminus of the *E. coli* OmpT protease variant is leucine;
   (2) phenylalanine, alanine, serine, cysteine, or tyrosine when the 97th amino acid from the N-terminus of the *E. coli* OmpT protease variant is methionine; or
   (3) alanine, valine, isoleucine, methionine, serine, threonine, cysteine, or asparagine when the 97th amino acid from the N-terminus of the *E. coli* OmpT protease variant is histidine.

2. The process of claim 1, wherein the amino acid sequence from the P10 position to the P3 position comprises only a single basic amino acid or only two or three consecutive basic amino acids.

3. The process of claim 2, wherein the basic amino acids are arginine and/or lysine.

4. The process of claim 3, wherein the basic amino acids are arginine.

5. The process of claim 1,
   wherein the polypeptide is a fusion protein comprising a protecting peptide and a target peptide,
   wherein the C-terminus of the protecting peptide is the P1 position and the N-terminus of the target peptide is the P1' position,
   wherein the fusion protein is produced by expressing a gene encoding the fusion protein in a host cell, and
   wherein cleavage of the fusion protein liberates the target peptide.

6. The process of claim 5, wherein a single basic amino acid or two or three consecutive basic amino acids are situated in the amino acid sequence from the P10 position to the P3 position.

7. The process of claim 5, wherein the *E. coli* OmpT protease variant is produced by expressing a gene encoding the *E. coli* OmpT protease variant in said host cell.

8. The process of claim 1, wherein two or three consecutive basic amino acids are situated between the P10 and P3 positions in the polypeptide.

9. The process of claim 8, wherein three consecutive basic amino acids are situated between the P5 and P3 positions in the polypeptide.

10. A process for cleaving a polypeptide comprising cleaving the polypeptide with an *E. coli* OmpT protease variant consisting of an amino acid substitution at the position of the amino acid sequence of SEQ ID NO: 41,
    wherein the 97th amino acid from the N-terminus of the *E. coli* OmpT protease variant is leucine, methionine, or histidine,
    wherein the polypeptide comprises a cleavage site that is a peptide bond between the P1 position and the P1' position, and
    wherein the P1 position is arginine or lysine and the P1' position is:
    (1) serine or alanine when the 97th amino acid from the N-terminus of the *E. coli* OmpT protease variant is leucine;
    (2) phenylalanine, alanine, serine, cysteine, or tyrosine when the 97th amino acid from the N-terminus of the *E.coli* OmpT protease variant is methionine: or
    (3) alanine, valine, isoleucine, methionine, serine, threonine, cysteine, or asparagine when the 97th amino acid from the N-terminus of the *E. coli* OmpT protease variant is histidine, and
    wherein the amino acid sequence from the P5 to P1 positions in the polypeptide is Arg-Arg-Arg-Ala-Arg (SEQ ID NO: 11).

11. A process for cleaving a polypeptide comprising cleaving the polypeptide with an *E. coli* OmpT protease variant consisting of an amino acid substitution at the 97the position of the amino acid sequence of SEQ ID NO: 41,
    wherein the 97th amino acid from the N-terminus of the *E. coli* OmpT protease variant is leucine, methionine, or histidine,
    wherein the polypeptide comprises a cleavage site that is a peptide bond between the P1 position and the P1' position, and
    wherein the P1' position is:
    (1) serine or alanine when the 97th amino acid from the N-terminus of the *E. coli* OmpT protease variant is leucine;
    (2) phenylalanine, alanine, serine, cysteine, or tyrosine when the 97th amino acid from the N-terminus of the *E. coli* OmpT protease variant is methionine; or
    (3) alanine, valine, isoleucine, methionine, serine threonine, cysteine, or asparagine, when the 97th amino acid from the N-terminus of the *E. coli* OmpT protease variant is histidine, and
    wherein the amino acid sequence from the P7 to P1 positions in the polypeptide is Asp-Ala-Arg-Arg-Arg-Ala-Arg (SEQ ID NO: 12).

12. The process of claim 5, wherein the target peptide consists of between 22 and 45 amino acid residues.

13. The process of claim 12, wherein the target peptide is adrenocorticotropic hormone (1-24), motilin, or calcitonin precursor.

* * * * *

SEQUENCE LISTING

<160> NUMBER OF SEQ ID NOS: 41

<210> SEQ ID NO 1
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Asp Asp Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Leu Leu Asp Leu Pro Glu Ala
65                  70                  75                  80

Asp Thr Val Val Val Pro Asp Ser Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Pro His His His His Pro Gly Gly Arg Gln
        115                 120                 125

Met His Gly Tyr Asp Ala Glu Leu Arg Leu Tyr Arg Arg His His Gly
    130                 135                 140

Ser Gly Ser Pro Tyr Arg His Pro Arg His Ala Glu Gly Thr Phe Thr
145                 150                 155                 160

Ser Asp Val Ser Ser Tyr Leu Glu Gly Gln Ala Ala Lys Glu Phe Ile
                165                 170                 175

Ala Trp Leu Val Lys Gly Arg Gly
            180

<210> SEQ ID NO 2
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Asp Asp Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Leu Leu Asp Leu Pro Glu Ala
65                  70                  75                  80

Asp Thr Val Val Val Pro Asp Ser Ser Asn Trp Gln Met His Gly Tyr
                85                  90                  95

Asp Ala Pro Ile Tyr Thr Asn Val Thr Tyr Pro Ile Thr Val Asn Pro

```
                    100                 105                 110

Pro Phe Val Pro Thr Glu Pro His His His Pro Gly Gly Arg Gln
            115                 120                 125

Met His Ala Ala Ala Ala Ala Ala Ala Arg Arg Ala Arg Ala
        130                 135                 140

Ala Gly Ser Pro Tyr Arg His Pro Arg His Ala Glu Gly Thr Phe Thr
145                 150                 155                 160

Ser Asp Val Ser Ser Tyr Leu Glu Gly Gln Ala Ala Lys Glu Phe Ile
                165                 170                 175

Ala Trp Leu Val Lys Gly Arg Gly
            180

<210> SEQ ID NO 3
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Asp Ala Arg Thr Asp Arg Pro
            35                  40                  45

Ser Gln Gln Leu Arg Ser Leu Asn Gly Glu Trp Arg Phe Ala Trp Phe
50                  55                  60

Pro Ala Pro Glu Ala Val Pro Glu Ser Leu Leu Asp Leu Pro Glu Ala
65                  70                  75                  80

Asp Thr Val Val Val Pro Asp Ser Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Pro His His His Pro Gly Gly Arg Gln
            115                 120                 125

Met His Ala Ala Ala Ala Ala Ala Ala Arg Arg Ala Arg Ala
        130                 135                 140

Ala Gly Ser Pro Tyr Arg His Pro Arg His Ala Glu Gly Thr Phe Thr
145                 150                 155                 160

Ser Asp Val Ser Ser Tyr Leu Glu Gly Gln Ala Ala Lys Glu Phe Ile
                165                 170                 175

Ala Trp Leu Val Lys Gly Arg Gly
            180

<210> SEQ ID NO 4
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
```

```
            20                  25                  30
Pro Phe Ala Ser Trp Arg Asn Ser Asp Asp Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Leu Leu Asp Leu Pro Glu Ala
65                  70                  75                  80

Asp Thr Val Val Pro Asp Ser Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Pro His His His Pro Gly Gly Arg Gln
        115                 120                 125

Met His Ala Ala Ala Ala Ala Ala Ala Arg Arg Arg Ala Arg Ala
    130                 135                 140

Ala Gly Ser Pro Tyr Arg His Pro Arg His Ala Glu Gly Thr Phe Thr
145                 150                 155                 160

Ser Asp Val Ser Ser Tyr Leu Glu Gly Gln Ala Ala Lys Glu Phe Ile
                165                 170                 175

Ala Trp Leu Val Lys Gly Arg Gly
            180
```

```
<210> SEQ ID NO 5
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Asp Asp Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Leu Leu Asp Leu Pro Glu Ala
65                  70                  75                  80

Asp Thr Val Val Pro Asp Ser Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Pro His His His Pro Gly Gly Arg Gln
        115                 120                 125

Met His Gly Tyr Asp Ala Glu Leu Arg Leu Tyr Arg Phe Val Pro Ile
    130                 135                 140

Phe Thr Tyr Gly Glu Leu Gln Arg Met Gln Glu Lys Glu Arg Asn Lys
145                 150                 155                 160

Gly Gln

<210> SEQ ID NO 6
<211> LENGTH: 165
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 6

```
Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Asp Asp Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Leu Leu Asp Leu Pro Glu Ala
65                  70                  75                  80

Asp Thr Val Val Val Pro Asp Ser Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Pro His His His Pro Gly Gly Arg Gln
        115                 120                 125

Met His Ala Ala Ala Ala Ala Ala Ala Arg Arg Arg Ala Arg Phe
    130                 135                 140

Val Pro Ile Phe Thr Tyr Gly Glu Leu Gln Arg Met Gln Glu Lys Glu
145                 150                 155                 160

Arg Asn Lys Gly Gln
            165
```

<210> SEQ ID NO 7
<211> LENGTH: 167
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Asp Asp Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Leu Leu Asp Leu Pro Glu Ala
65                  70                  75                  80

Asp Thr Val Val Val Pro Asp Ser Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Pro His His His Pro Gly Gly Arg Gln
        115                 120                 125

Met His Ala Ala Ala Ala Ala Ala Ala Arg Arg Arg Ala Arg Ser
    130                 135                 140

Tyr Ser Met Glu His Phe Arg Trp Gly Lys Pro Val Gly Lys Lys Arg
```

```
145                 150                 155                 160
Arg Pro Val Lys Val Tyr Pro
                165

<210> SEQ ID NO 8
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
                20                  25                  30

Pro Phe Ala Ser Trp Arg Asn Ser Asp Ala Arg Thr Asp Arg Pro
            35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Leu Leu Asp Leu Pro Glu Ala
65                  70                  75                  80

Asp Thr Val Val Val Pro Asp Ser Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Pro His His His Pro Gly Gly Arg Gln
        115                 120                 125

Met His Ala Ala Ala Ala Ala Ala Ala Arg Arg Arg Ala Arg Cys
    130                 135                 140

Gly Asn Leu Ser Thr Cys Met Leu Gly Thr Tyr Thr Gln Asp Phe Asn
145                 150                 155                 160

Lys Phe His Thr Phe Pro Gln Thr Ala Ile Gly Val Gly Ala Pro Gly
                165                 170                 175

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Tyr Lys Arg His
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Arg Arg Ala
1

<210> SEQ ID NO 11
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Arg Ala Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ala Arg Arg Arg Ala Arg
1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg Ala Arg
1

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Arg Arg Ala Arg Ala Ala
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Arg Ala Arg Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

Asp Ala Arg Arg Arg Ala Arg Ala
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Gly Gly Phe Leu Arg
1               5

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Ala Ala Ala Ala Ala Ala Arg Arg Ala Ala Ala Ala Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Ala Ala Ala Ala Ala Arg Ala Arg Arg Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Ala Ala Ala Ala Arg Ala Ala Arg Arg Ala Ala Ala Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ala Ala Ala Ala Arg Ala Ala Ala Arg Arg Ala Ala Ala Ala
1               5                   10                  15

<210> SEQ ID NO 22
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 22

Ala Ala Ala Ala Arg Ala Ala Ala Arg Arg Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ala Arg Ala Ala Ala Ala Ala Arg Arg Ala Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ala Arg Ala Ala Ala Ala Ala Arg Arg Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Arg Ala Ala Ala Ala Ala Ala Arg Arg Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Ala Ala Ala Ala Ala Ala Arg Arg Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ala Ala Ala Ala Ala Ala Ala Ala Arg Arg Arg Ala Ala Ala
1               5                   10                  15

```
<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ala Ala Ala Ala Ala Ala Ala Ala Arg Arg Ala Ala Arg Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Ala Ala Ala Ala Ala Ala Ala Arg Arg Ala Ala Ala Arg
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Ala Ala Ala Ala Ala Ala Ala Ala Ala Arg Ala Arg Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ala Ala Ala Ala Ala Ala Ala Ala Arg Ala Ala Arg Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Ala Ala Ala Ala Ala Ala Arg Arg Arg Arg Ala Arg Ala Ala
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

Ala Ala Ala Ala Ala Ala Ala Ala Arg Arg Arg Arg Ala Ala
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Ala Ala Ala Ala Ala Ala Asp Arg Arg Arg Ala Arg Ala Ala
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ala Ala Ala Ala Ala Asp Ala Arg Arg Arg Ala Arg Ala Ala
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Ala Ala Ala Ala Asp Ala Ala Arg Arg Arg Ala Arg Ala Ala
1               5                   10                  15

<210> SEQ ID NO 37
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met His Ala Ala Ala Ala Ala Ala Asp Arg Arg Arg Ala Arg Phe
1               5                   10                  15

Val Pro Ile Phe Thr Tyr Gly Glu Leu Gln Arg Met Gln Glu Lys Glu
            20                  25                  30

Arg Asn Lys Gly Gln
        35

<210> SEQ ID NO 38
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met His Ala Ala Ala Ala Ala Ala Asp Ala Arg Arg Arg Ala Arg Phe
1               5                   10                  15

Val Pro Ile Phe Thr Tyr Gly Glu Leu Gln Arg Met Gln Glu Lys Glu
        20                  25                  30

Arg Asn Lys Gly Gln
        35

<210> SEQ ID NO 39
<211> LENGTH: 1759
<212> TYPE: DNA
<213> ORGANISM: Escherichia coli

<400> SEQUENCE: 39

| | | | | | |
|---|---|---|---|---|---|
| gattcgaact | cggcccacga | cttagaagtt | ctagaacgac | attttaagtc | aacaacttac | 60 |
| cgcgccatct | ctgcgctcac | acgtcccact | acctcaaaac | atgtaaagcc | ttgcaagcca | 120 |
| ttgcgaggcc | ttatgtgtct | cagttttgtc | cctctttttt | gtactaaaaa | acatagtaat | 180 |
| tgaggataaa | cctcatgcta | ttttcgctta | tatgcctcta | aaggcatggc | acttaaatag | 240 |
| ataaaagcac | cacaaaagca | taaaaaaacc | acacagtaaa | accgaaatat | gaaacaataa | 300 |
| cagataatta | accaaaaac | agatagcgca | ttgtgataat | cattcaatac | taaacaaaat | 360 |
| ataaacagtg | gagcaatatg | taattgactc | attaagttag | atataaaaaa | tacatattca | 420 |
| atcattaaaa | cgattgaatg | gagaactttt | atgcgggcga | aacttctggg | aatagtcctg | 480 |
| acaaccccta | ttgcgatcag | ctcttttgct | tctaccgaga | ctttatcgtt | tactcctgac | 540 |
| aacataaatg | cggacattag | tcttggaact | ctgagcggaa | aaacaaaaga | gcgtgtttat | 600 |
| ctagccgaag | aaggaggccg | aaaagtcagt | caactcgact | ggaaattcaa | taacgctgca | 660 |
| attattaaag | gtgcaattaa | ttgggatttg | atgccccaga | tatctatcgg | ggctgctggc | 720 |
| tggacaactc | tcggcagccg | aggtggcaat | atggtcgatc | aggactggat | ggattccagt | 780 |
| aaccccggaa | cctggacgga | tgaaagtaga | caccctgata | cacaactcaa | ttatgccaac | 840 |
| gaatttgatc | tgaatatcaa | aggctggctc | tcaacgaac | ccaattaccg | cctgggactc | 900 |
| atggccggat | atcaggaaag | ccgttatagc | tttacagcca | gaggtggttc | ctatatctac | 960 |
| agttctgagg | agggattcag | agatgatatc | ggctccttcc | cgaatggaga | aagagcaatc | 1020 |
| ggctacaaac | aacgttttaa | aatgccctac | attggcttga | ctggaagtta | tcgttatgaa | 1080 |
| gattttgaac | tcggtggcac | atttaaatac | agcggctggg | tggaatcatc | tgataacgat | 1140 |
| gaacactatg | acccgggaaa | aagaatcact | tatcgcagta | aggtcaaaga | ccaaaattac | 1200 |
| tattctgttg | cagtcaatgc | aggttattac | gtcacaccta | acgcaaaagt | ttatgttgaa | 1260 |
| ggcgcatgga | atcgggttac | gaataaaaaa | ggtaatactt | cactttatga | tcacaataat | 1320 |
| aacacttcag | actacagcaa | aaatggagca | ggtatagaaa | actataactt | catcactact | 1380 |
| gctggtctta | agtacacatt | ttaagaacgc | caactaaaat | ttccccgagg | tgaaaatcgc | 1440 |
| cccgggaata | actagccatt | tcaatgtaac | aattaaccct | taaaataaac | ccagaaggtt | 1500 |
| attaactaaa | tcacatagaa | aaccatcaat | tatagtatgt | ataaaatagg | cgacagcaac | 1560 |
| ccaattacaa | attaatggtt | ccagaatatc | acatcaaaaa | aaacgctgta | taatattata | 1620 |
| attaacatgt | agacaacttg | taataaacat | tatcagtcaa | ttgttttgtt | tattccatct | 1680 |
| gtgacgccga | ttatttctc | aaaataatga | gatggcgtga | gaccataata | atctttaaat | 1740 |
| gcacatatga | aatatgaag | | | | | 1759 |

<210> SEQ ID NO 40
<211> LENGTH: 317
<212> TYPE: PRT

<213> ORGANISM: Escherichia coli

<400> SEQUENCE: 40

Met Arg Ala Lys Leu Leu Gly Ile Val Leu Thr Thr Pro Ile Ala Ile
1               5                   10                  15

Ser Ser Phe Ala Ser Thr Glu Thr Leu Ser Phe Thr Pro Asp Asn Ile
            20                  25                  30

Asn Ala Asp Ile Ser Leu Gly Thr Leu Ser Gly Lys Thr Lys Glu Arg
        35                  40                  45

Val Tyr Leu Ala Glu Glu Gly Arg Lys Val Ser Gln Leu Asp Trp
    50                  55                  60

Lys Phe Asn Asn Ala Ala Ile Ile Lys Gly Ala Ile Asn Trp Asp Leu
65                  70                  75                  80

Met Pro Gln Ile Ser Ile Gly Ala Ala Gly Trp Thr Thr Leu Gly Ser
                85                  90                  95

Arg Gly Gly Asn Met Val Asp Gln Asp Trp Met Asp Ser Ser Asn Pro
            100                 105                 110

Gly Thr Trp Thr Asp Glu Ser Arg His Pro Asp Thr Gln Leu Asn Tyr
        115                 120                 125

Ala Asn Glu Phe Asp Leu Asn Ile Lys Gly Trp Leu Leu Asn Glu Pro
    130                 135                 140

Asn Tyr Arg Leu Gly Leu Met Ala Gly Tyr Gln Ser Arg Tyr Ser
145                 150                 155                 160

Phe Thr Ala Arg Gly Gly Ser Tyr Ile Tyr Ser Ser Glu Glu Gly Phe
                165                 170                 175

Arg Asp Asp Ile Gly Ser Phe Pro Asn Gly Glu Arg Ala Ile Gly Tyr
            180                 185                 190

Lys Gln Arg Phe Lys Met Pro Tyr Ile Gly Leu Thr Gly Ser Tyr Arg
        195                 200                 205

Tyr Glu Asp Phe Glu Leu Gly Gly Thr Phe Lys Tyr Ser Gly Trp Val
    210                 215                 220

Glu Ser Ser Asp Asn Asp Glu His Tyr Asp Pro Gly Lys Arg Ile Thr
225                 230                 235                 240

Tyr Arg Ser Lys Val Lys Asp Gln Asn Tyr Tyr Ser Val Ala Val Asn
                245                 250                 255

Ala Gly Tyr Tyr Val Thr Pro Asn Ala Lys Val Tyr Val Glu Gly Ala
            260                 265                 270

Trp Asn Arg Val Thr Asn Lys Lys Gly Asn Thr Ser Leu Tyr Asp His
        275                 280                 285

Asn Asn Asn Thr Ser Asp Tyr Ser Lys Asn Gly Ala Gly Ile Glu Asn
    290                 295                 300

Tyr Asn Phe Ile Thr Thr Ala Gly Leu Lys Tyr Thr Phe
305                 310                 315

<210> SEQ ID NO 41
<211> LENGTH: 297
<212> TYPE: PRT
<213> ORGANISM: Escherichia coli

<400> SEQUENCE: 41

Ser Thr Glu Thr Leu Ser Phe Thr Pro Asp Asn Ile Asn Ala Asp Ile
1               5                   10                  15

Ser Leu Gly Thr Leu Ser Gly Lys Thr Lys Glu Arg Val Tyr Leu Ala
            20                  25                  30

Glu Glu Gly Gly Arg Lys Val Ser Gln Leu Asp Trp Lys Phe Asn Asn

```
                        35                  40                  45
Ala Ala Ile Ile Lys Gly Ala Ile Asn Trp Asp Leu Met Pro Gln Ile
        50                  55                  60

Ser Ile Gly Ala Ala Gly Trp Thr Thr Leu Gly Ser Arg Gly Gly Asn
65                  70                  75                  80

Met Val Asp Gln Asp Trp Met Asp Ser Ser Asn Pro Gly Thr Trp Thr
                85                  90                  95

Asp Glu Ser Arg His Pro Asp Thr Gln Leu Asn Tyr Ala Asn Glu Phe
            100                 105                 110

Asp Leu Asn Ile Lys Gly Trp Leu Leu Asn Glu Pro Asn Tyr Arg Leu
        115                 120                 125

Gly Leu Met Ala Gly Tyr Gln Glu Ser Arg Tyr Ser Phe Thr Ala Arg
        130                 135                 140

Gly Gly Ser Tyr Ile Tyr Ser Ser Glu Glu Gly Phe Arg Asp Asp Ile
145                 150                 155                 160

Gly Ser Phe Pro Asn Gly Glu Arg Ala Ile Gly Tyr Lys Gln Arg Phe
                165                 170                 175

Lys Met Pro Tyr Ile Gly Leu Thr Gly Ser Tyr Arg Tyr Glu Asp Phe
            180                 185                 190

Glu Leu Gly Gly Thr Phe Lys Tyr Ser Gly Trp Val Glu Ser Ser Asp
        195                 200                 205

Asn Asp Glu His Tyr Asp Pro Gly Lys Arg Ile Thr Tyr Arg Ser Lys
        210                 215                 220

Val Lys Asp Gln Asn Tyr Tyr Ser Val Ala Val Asn Ala Gly Tyr Tyr
225                 230                 235                 240

Val Thr Pro Asn Ala Lys Val Tyr Val Glu Gly Ala Trp Asn Arg Val
                245                 250                 255

Thr Asn Lys Lys Gly Asn Thr Ser Leu Tyr Asp His Asn Asn Asn Thr
            260                 265                 270

Ser Asp Tyr Ser Lys Asn Gly Ala Gly Ile Glu Asn Tyr Asn Phe Ile
            275                 280                 285

Thr Thr Ala Gly Leu Lys Tyr Thr Phe
290                 295
```